(12) United States Patent
Ishii et al.

(10) Patent No.: US 11,268,098 B2
(45) Date of Patent: Mar. 8, 2022

(54) NON-AGGREGATING IMMUNOSTIMULATORY OLIGONUCLEOTIDES

(71) Applicants: National Institutes of Biomedical Innovation, Health and Nutrition, Ibaraki (JP); GeneDesign, Inc., Ibaraki (JP)

(72) Inventors: Ken Ishii, Ibaraki (JP); Taiki Aoshi, Ibaraki (JP); Hideaki Sato, Ibaraki (JP)

(73) Assignees: National Institutes of Biomedical Innovation, Health and Nutrition, Ibaraki (JP); GeneDesign, Inc., Ibaraki (JP)

( * ) Notice: Subject to any disclaimer, the term of this patent is extended or adjusted under 35 U.S.C. 154(b) by 31 days.

(21) Appl. No.: 15/539,617

(22) PCT Filed: Dec. 24, 2015

(86) PCT No.: PCT/JP2015/006435
§ 371 (c)(1),
(2) Date: Jun. 23, 2017

(87) PCT Pub. No.: WO2016/103703
PCT Pub. Date: Jun. 30, 2016

(65) Prior Publication Data
US 2017/0362591 A1 Dec. 21, 2017

(30) Foreign Application Priority Data

Dec. 25, 2014 (JP) .............................. JP2014-263017
Jun. 11, 2015 (JP) .............................. JP2015-118731

(51) Int. Cl.
| | | |
|---|---|---|
| *C12N 15/11* | (2006.01) | |
| *C12N 15/117* | (2010.01) | |
| *A61K 9/127* | (2006.01) | |
| *A61K 31/7088* | (2006.01) | |
| *C12N 15/09* | (2006.01) | |

(52) U.S. Cl.
CPC ............ *C12N 15/117* (2013.01); *A61K 9/127* (2013.01); *A61K 31/7088* (2013.01); *C12N 15/09* (2013.01); *C12N 2310/17* (2013.01); *C12N 2310/315* (2013.01)

(58) Field of Classification Search
CPC ................................................... C12N 15/117
See application file for complete search history.

(56) References Cited

U.S. PATENT DOCUMENTS

| | | | | |
|---|---|---|---|---|
| 2008/0045473 A1* | 2/2008 | Uhlmann | ................ | A61P 11/06 514/44 R |
| 2009/0263413 A1 | 10/2009 | Iwamura et al. | | |
| 2015/0166999 A1 | 6/2015 | Gemba | | |

FOREIGN PATENT DOCUMENTS

| | | | | |
|---|---|---|---|---|
| JP | 2009-35530 A | 2/2009 | | |
| WO | 00/61151 A2 | 10/2000 | | |
| WO | 01/51500 A1 | 7/2001 | | |
| WO | WO-0193902 A2 * | 12/2001 | ............. | A61K 39/39 |
| WO | WO-2004058179 A2 * | 7/2004 | ............. | C07H 21/02 |
| WO | WO-2004084940 A1 * | 10/2004 | ......... | A61K 39/0011 |
| WO | WO-2005009355 A2 * | 2/2005 | ......... | A61K 38/2013 |
| WO | 2005/030259 A2 | 4/2005 | | |
| WO | 2007/068747 A1 | 6/2007 | | |
| WO | WO-2007095316 A2 * | 8/2007 | ............. | A61K 39/00 |
| WO | 2007/139190 A1 | 12/2007 | | |
| WO | 2008/142509 A2 | 11/2008 | | |
| WO | 2014/010718 A1 | 1/2014 | | |
| WO | WO-2016098832 A1 * | 6/2016 | ............. | A61K 47/36 |

OTHER PUBLICATIONS

Shimada et al, A Polysaccharide Carrier to Effectively Deliver Native Phosphodiester CpG DNA to Antigen-Presenting Cells, Bioconjugate Chemistry, 2007, 18: 1280-1286 (Year: 2007).*
Minari et al, Enhanced Cytokine Secretion from Primary Macrophages due to Dectin-1 Mediated Uptake of CpG DNA/beta-1,3-Glucan Complex , Bioconjugate Chemistry, 2011, 22: 9-15 (Year: 2011).*
Machine translation of WO2016098832, 2016, pp. 1-10 (Year: 2016).*
Aoshi et al., "Development of Nonaggregating Poly-A Tailed Immunostimulatory A/D Type CpG Oligodeoxynucleotides Applicable for Clinical Use," *Journal of Immunology Research 2015*: 2015, 20 pages.
Ishii et al., "Innate immune recognition of, and regulation by, DNA," *Trends In Immunology* 27(II):525-532, 2006.
Mochizuki et al., "Immunization with antigenic peptides complexed with β-glucan induces potent cytotoxic T-lymphocyte activity in combination with CpG-ODNs," *Journal of Controlled Release* 220:495-502, 2015.
Samulowitz et al., "A Novel Class of Immune-Stimulatory Oligodeoxynucleotides Unifies High Potency in Type I Interferon Induction with Preferred Structural Propertied," *Oligonucleotides* 20(2):93-101, 2010.
Shimada et al., "A Polysaccharide Carrier to Effectively Deliver Native Phosphodiester CpG DNA to Antigen-Presenting Cells," *Bioconjugate Chem.* 18:1280-1286, 2007.

(Continued)

*Primary Examiner* — Ekaterina Poliakova-Georgantas
(74) *Attorney, Agent, or Firm* — Seed IP Law Group LLP

(57) ABSTRACT

Provided are non-aggregating immunostimulatory oligonucleotides. The present invention also provides a delivery agent for an immunostimulatory-oligonucleotide nucleic acid medicine, said delivery agent including a nucleic acid that contains a phosphorothioated nucleotide. According to another aspect, the present invention further provides an oligonucleotide including a bioactive core, and a nucleic acid that contains a phosphorothioated nucleotide. The present invention yet further provides an immunostimulator including the bioactive core of a type A/D, type B/K, or type C immunostimulatory oligonucleotide.

13 Claims, 16 Drawing Sheets

Specification includes a Sequence Listing.

(56) References Cited

OTHER PUBLICATIONS

Bode et al., "CpG DNA as a vaccine adjuvant," *Expert Rev Vaccines* 10(4):499-511, 2011.
Costa et al., "Structural studies of oligonucleotides containing G-quadruplex motifs using AFM," *Biochemical and Biophysical Research Communications* 313:1065-1072, 2004.
Grajkowski et al., "Thermolytic CpG-containing DNA oligonucleotides as potential immunotherapeutic prodrugs," *Nucleic Acids Research* 55(11):3550-3560, 2005.
Kerkmann et al., "Spontaneous Formation of Nucleic Acid-based Nanoparticles Is Responsible for High Interferon-α Induction by CpG-A in Plasmacytoid Dendritic Cells," *Journal of Biological Chemistry* 280(9):8086-8093, 2005.
Klein et al., "Higher order structure of short immunostimulatory oligonucleotides studied by atomic force microscopy," *Ultramicroscopy* 110:689-693, 2010.
Klinman, "Immunotherapeutic Uses of CpG Oligodeoxynucleotides," *Nat Rev Immunol* 4:249-258, 2004.
Puig et al., "Use of thermolytic protective groups to prevent G-tetrad formation in CpG ODN type D: structural studies and immunomodulatory activity in primates," *Nucleic Acids Research* 54(22):6488-6495, 2006.
Samulowitz et al., "A Novel Class of Immune-Stimulatory CpG Oligodeoxynucleotides Unifies High Potency in Type I Interferon Induction with Preferred Structural Properties," *Oligonucleotides* 20(2):93-101, 2010.
Steinhagen et al., "Activation of type I interferon-dependent genes characterizes the "core response" induced by CpG DNA," *Journal of Leukocyte Biology* 92:115-185, 2012.
Tougan et al., "TLR9 adjuvants enhance immunogenicity and protective efficacy of the SE36/AHG malaria vaccine in nonhuman primate models," *Human Vaccines & Immunotherapeutics* 9(2):283-290, 2013.
Verthelyi et al., "CpG Oligodeoxynucleotides Protect Normal and SIV-Infected Macaques from *Leishmania* Infection," *J Immunol* 170:4717-4723, 2003.
Verthelyi et al., "Human Peripheral Blood Cells Differentially Recognize and Respond to Two Distinct CpG Motifs," *J Immunol* 166:2372-2377, 2001.
Vollmer et al., "Immunotherapeutic applications of CpG oligodeoxynucleotide TLR9 agonists," *Advanced Drug Delivery Reviews* 61:195-204, 2009.
Wu et al., "Necessity of Oligonucleotide Aggregation for Toll-like Receptor 9 Activation," *Journal of Biological Chemistry* 279(32):33071-33078, 2004.

\* cited by examiner

SEQUENCE LISTING

```
<160> NUMBER OF SEQ ID NOS: 85

<210> SEQ ID NO 1
<211> LENGTH: 60
<212> TYPE: DNA
<213> ORGANISM: artificial sequence
<220> FEATURE:
<223> OTHER INFORMATION: D35(CG)G-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 1
ggtgcatcga tgcagggggg aaaaaaaaaa aaaaaaaaaa aaaaaaaaaa aaaaaaaaaa      60

<210> SEQ ID NO 2
<211> LENGTH: 60
<212> TYPE: DNA
<213> ORGANISM: artificial sequence
<220> FEATURE:
<223> OTHER INFORMATION: D35(GC)G-dAs40
<220> FEATURE:
<221> NAME/KEY: phosphorothioate linkage
```

```
<222> LOCATION: (1)..(1)
<220> FEATURE:
<221> NAME/KEY: phosphorothioate linkage
<222> LOCATION: (18)..(59)

<400> SEQUENCE: 2
ggtgcatgca tgcagggggg aaaaaaaaaa aaaaaaaaaa aaaaaaaaaa aaaaaaaaaa      60

<210> SEQ ID NO 3
<211> LENGTH: 60
<212> TYPE: DNA
<213> ORGANISM: artificial sequence
<220> FEATURE:
<223> OTHER INFORMATION: D35(TG)G-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 3
ggtgcattga tgcagggggg aaaaaaaaaa aaaaaaaaaa aaaaaaaaaa aaaaaaaaaa      60

<210> SEQ ID NO 4
<211> LENGTH: 60
<212> TYPE: DNA
<213> ORGANISM: artificial sequence
<220> FEATURE:
<223> OTHER INFORMATION: D35(CT)G-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 4
ggtgcatcta tgcagggggg aaaaaaaaaa aaaaaaaaaa aaaaaaaaaa aaaaaaaaaa      60

<210> SEQ ID NO 5
<211> LENGTH: 60
<212> TYPE: DNA
<213> ORGANISM: artificial sequence
<220> FEATURE:
<223> OTHER INFORMATION: D35(CG)A-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 5
ggtgcatcga tgcaaaaaaa aaaaaaaaaa aaaaaaaaaa aaaaaaaaaa aaaaaaaaaa      60

<210> SEQ ID NO 6
<211> LENGTH: 60
<212> TYPE: DNA
<213> ORGANISM: artificial sequence
<220> FEATURE:
<223> OTHER INFORMATION: D35(GC)A-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 6
```
ggtgcatgca tgcaaaaaaa aaaaaaaaaa aaaaaaaaaa aaaaaaaaaa aaaaaaaaaa     60

<210> SEQ ID NO 7
<211> LENGTH: 60
<212> TYPE: DNA
<213> ORGANISM: artificial sequence
<220> FEATURE:
<223> OTHER INFORMATION: D35(TG)A-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 7
ggtgcattga tgcaaaaaaa aaaaaaaaaa aaaaaaaaaa aaaaaaaaaa aaaaaaaaaa     60

<210> SEQ ID NO 8
<211> LENGTH: 60
<212> TYPE: DNA
<213> ORGANISM: artificial sequence
<220> FEATURE:
<223> OTHER INFORMATION: D35(CT)A-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 8
ggtgcatcta tgcaaaaaaa aaaaaaaaaa aaaaaaaaaa aaaaaaaaaa aaaaaaaaaa     60

<210> SEQ ID NO 9
<211> LENGTH: 60
<212> TYPE: DNA
<213> ORGANISM: artificial sequence
<220> FEATURE:
<223> OTHER INFORMATION: D35(CG)T-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 9
ggtgcatcga tgcatttttt aaaaaaaaaa aaaaaaaaaa aaaaaaaaaa aaaaaaaaaa     60

<210> SEQ ID NO 10
<211> LENGTH: 60
<212> TYPE: DNA
<213> ORGANISM: artificial sequence
<220> FEATURE:
<223> OTHER INFORMATION: D35(GC)T-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 10
ggtgcatgca tgcatttttt aaaaaaaaaa aaaaaaaaaa aaaaaaaaaa aaaaaaaaaa     60

<210> SEQ ID NO 11
<211> LENGTH: 60
<212> TYPE: DNA
<213> ORGANISM: artificial sequence

```
<220> FEATURE:
<223> OTHER INFORMATION: D35(TG)T-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 11
ggtgcattga tgcatttttt aaaaaaaaaa aaaaaaaaaa aaaaaaaaaa aaaaaaaaaa      60

<210> SEQ ID NO 12
<211> LENGTH: 60
<212> TYPE: DNA
<213> ORGANISM: artificial sequence
<220> FEATURE:
<223> OTHER INFORMATION: D35(CT)T-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 12
ggtgcatcta tgcatttttt aaaaaaaaaa aaaaaaaaaa aaaaaaaaaa aaaaaaaaaa      60

<210> SEQ ID NO 13
<211> LENGTH: 60
<212> TYPE: DNA
<213> ORGANISM: artificial sequence
<220> FEATURE:
<223> OTHER INFORMATION: D35(CG)C-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 13
ggtgcatcga tgcacccccc aaaaaaaaaa aaaaaaaaaa aaaaaaaaaa aaaaaaaaaa      60

<210> SEQ ID NO 14
<211> LENGTH: 60
<212> TYPE: DNA
<213> ORGANISM: artificial sequence
<220> FEATURE:
<223> OTHER INFORMATION: D35(GC)C-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 14
ggtgcatgca tgcacccccc aaaaaaaaaa aaaaaaaaaa aaaaaaaaaa aaaaaaaaaa      60

<210> SEQ ID NO 15
<211> LENGTH: 60
<212> TYPE: DNA
<213> ORGANISM: artificial sequence
<220> FEATURE:
<223> OTHER INFORMATION: D35(TG)C-dAs40
<220> FEATURE:
<221> NAME/KEY: phosphorothioate linkage
<222> LOCATION: (1)..(1)
<220> FEATURE:
<221> NAME/KEY: phosphorothioate linkage
```

<222> LOCATION: (18)..(59)

<400> SEQUENCE: 15
ggtgcattga tgcacccccc aaaaaaaaaa aaaaaaaaaa aaaaaaaaaa aaaaaaaaaa      60

<210> SEQ ID NO 16
<211> LENGTH: 60
<212> TYPE: DNA
<213> ORGANISM: artificial sequence
<220> FEATURE:
<223> OTHER INFORMATION: D35(CT)C-dAs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 16
ggtgcatcta tgcacccccc aaaaaaaaaa aaaaaaaaaa aaaaaaaaaa aaaaaaaaaa      60

<210> SEQ ID NO 17
<211> LENGTH: 60
<212> TYPE: DNA
<213> ORGANISM: artificial sequence
<220> FEATURE:
<223> OTHER INFORMATION: D35T-dA40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(20)

<400> SEQUENCE: 17
ggtgcatcga tgcatttttt aaaaaaaaaa aaaaaaaaaa aaaaaaaaaa aaaaaaaaaa      60

<210> SEQ ID NO 18
<211> LENGTH: 60
<212> TYPE: DNA
<213> ORGANISM: artificial sequence
<220> FEATURE:
<223> OTHER INFORMATION: D35T-dTs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 18
ggtgcatcga tgcatttttt tttttttttt tttttttttt tttttttttt tttttttttt      60

<210> SEQ ID NO 19
<211> LENGTH: 60
<212> TYPE: DNA
<213> ORGANISM: artificial sequence
<220> FEATURE:
<223> OTHER INFORMATION: D35T-dT40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(20)

<400> SEQUENCE: 19
ggtgcatcga tgcatttttt tttttttttt tttttttttt tttttttttt tttttttttt      60

```
<210> SEQ ID NO 20
<211> LENGTH: 60
<212> TYPE: DNA
<213> ORGANISM: artificial sequence
<220> FEATURE:
<223> OTHER INFORMATION: D35T-dCs40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(59)

<400> SEQUENCE: 20
ggtgcatcga tgcattttt cccccccccc cccccccccc cccccccccc cccccccccc    60

<210> SEQ ID NO 21
<211> LENGTH: 60
<212> TYPE: DNA
<213> ORGANISM: artificial sequence
<220> FEATURE:
<223> OTHER INFORMATION: D35T-dC40
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(20)

<400> SEQUENCE: 21
ggtgcatcga tgcattttt cccccccccc cccccccccc cccccccccc cccccccccc    60

<210> SEQ ID NO 22
<211> LENGTH: 12
<212> TYPE: DNA
<213> ORGANISM: artificial sequence
<220> FEATURE:
<223> OTHER INFORMATION: D35core

<400> SEQUENCE: 22
tgcatcgatg ca                                                       12

<210> SEQ ID NO 23
<211> LENGTH: 52
<212> TYPE: DNA
<213> ORGANISM: artificial sequence
<220> FEATURE:
<223> OTHER INFORMATION: D35core-dAs40
<220> FEATURE:
<221> NAME/KEY: phosphorothioate linkage
<222> LOCATION: (12)..(51)

<400> SEQUENCE: 23
tgcatcgatg caaaaaaaaa aaaaaaaaaa aaaaaaaaaa aaaaaaaaaa aa            52

<210> SEQ ID NO 24
<211> LENGTH: 58
<212> TYPE: DNA
<213> ORGANISM: artificial sequence
<220> FEATURE:
<223> OTHER INFORMATION: D35coreT-dAs40
<220> FEATURE:
<221> NAME/KEY: phosphorothioate linkage
<222> LOCATION: (16)..(57)

<400> SEQUENCE: 24
tgcatcgatg catttttaa aaaaaaaaaa aaaaaaaaaa aaaaaaaaaa aaaaaaaa       58

<210> SEQ ID NO 25
```

```
<211> LENGTH: 22
<212> TYPE: DNA
<213> ORGANISM: artificial sequence
<220> FEATURE:
<223> OTHER INFORMATION: D35core-dAs10
<220> FEATURE:
<221> NAME/KEY: phosphorothioate linkage
<222> LOCATION: (12)..(21)

<400> SEQUENCE: 25
tgcatcgatg caaaaaaaaa aa                                          22

<210> SEQ ID NO 26
<211> LENGTH: 32
<212> TYPE: DNA
<213> ORGANISM: artificial sequence
<220> FEATURE:
<223> OTHER INFORMATION: D35core-dAs20
<220> FEATURE:
<221> NAME/KEY: phosphorothioate linkage
<222> LOCATION: (12)..(31)

<400> SEQUENCE: 26
tgcatcgatg caaaaaaaaa aaaaaaaaaa aa                               32

<210> SEQ ID NO 27
<211> LENGTH: 42
<212> TYPE: DNA
<213> ORGANISM: artificial sequence
<220> FEATURE:
<223> OTHER INFORMATION: D35core-dAs30
<220> FEATURE:
<221> NAME/KEY: phosphorothioate linkage
<222> LOCATION: (12)..(41)

<400> SEQUENCE: 27
tgcatcgatg caaaaaaaaa aaaaaaaaaa aaaaaaaaaa aa                    42

<210> SEQ ID NO 28
<211> LENGTH: 52
<212> TYPE: DNA
<213> ORGANISM: artificial sequence
<220> FEATURE:
<223> OTHER INFORMATION: D35core-dAs40
<220> FEATURE:
<221> NAME/KEY: phosphorothioate linkage
<222> LOCATION: (12)..(51)

<400> SEQUENCE: 28
tgcatcgatg caaaaaaaaa aaaaaaaaaa aaaaaaaaaa aaaaaaaaaa aa         52

<210> SEQ ID NO 29
<211> LENGTH: 40
<212> TYPE: DNA
<213> ORGANISM: artificial sequence
<220> FEATURE:
<223> OTHER INFORMATION: dAs40 tail
<220> FEATURE:
<221> NAME/KEY: phosphorothioate linkage
<222> LOCATION: (1)..(39)

<400> SEQUENCE: 29
aaaaaaaaaa aaaaaaaaaa aaaaaaaaaa aaaaaaaaaa                       40

<210> SEQ ID NO 30
<211> LENGTH: 20
<212> TYPE: DNA
<213> ORGANISM: artificial sequence
<220> FEATURE:
```

```
<223> OTHER INFORMATION: K3

<400> SEQUENCE: 30
atcgactctc gagcgttctc                                          20

<210> SEQ ID NO 31
<211> LENGTH: 20
<212> TYPE: DNA
<213> ORGANISM: artificial sequence
<220> FEATURE:
<223> OTHER INFORMATION: D35
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(19)

<400> SEQUENCE: 31
ggtgcatcga tgcagggggg                                          20

<210> SEQ ID NO 32
<211> LENGTH: 20
<212> TYPE: DNA
<213> ORGANISM: artificial sequence
<220> FEATURE:
<223> OTHER INFORMATION: D35A
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(19)

<400> SEQUENCE: 32
ggtgcatcga tgcaaaaaaa                                          20

<210> SEQ ID NO 33
<211> LENGTH: 20
<212> TYPE: DNA
<213> ORGANISM: artificial sequence
<220> FEATURE:
<223> OTHER INFORMATION: D35T
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(19)

<400> SEQUENCE: 33
ggtgcatcga tgcatttttt                                          20

<210> SEQ ID NO 34
<211> LENGTH: 14
<212> TYPE: DNA
<213> ORGANISM: artificial sequence
<220> FEATURE:
<223> OTHER INFORMATION: D35C
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(19)

<400> SEQUENCE: 34
ggtgcatcga tgca                                                14
```

-continued

```
<210> SEQ ID NO 35
<211> LENGTH: 13
<212> TYPE: DNA
<213> ORGANISM: artificial sequence
<220> FEATURE:
<223> OTHER INFORMATION: D35core-dAs1
<220> FEATURE:
<221> NAME/KEY: phosphorothioate linkage
<222> LOCATION: (12)..(12)

<400> SEQUENCE: 35
tgcatcgatg caa                                                          13

<210> SEQ ID NO 36
<211> LENGTH: 14
<212> TYPE: DNA
<213> ORGANISM: artificial sequence
<220> FEATURE:
<223> OTHER INFORMATION: D35core-dAs2
<220> FEATURE:
<221> NAME/KEY: phosphorothioate linkage
<222> LOCATION: (12)..(13)

<400> SEQUENCE: 36
tgcatcgatg caaa                                                         14

<210> SEQ ID NO 37
<211> LENGTH: 15
<212> TYPE: DNA
<213> ORGANISM: artificial sequence
<220> FEATURE:
<223> OTHER INFORMATION: D35core-dAs3
<220> FEATURE:
<221> NAME/KEY: phosphorothioate linkage
<222> LOCATION: (12)..(14)

<400> SEQUENCE: 37
tgcatcgatg caaaa                                                        15

<210> SEQ ID NO 38
<211> LENGTH: 16
<212> TYPE: DNA
<213> ORGANISM: artificial sequence
<220> FEATURE:
<223> OTHER INFORMATION: D35core-dAs4
<220> FEATURE:
<221> NAME/KEY: phosphorothioate linkage
<222> LOCATION: (12)..(15)

<400> SEQUENCE: 38
tgcatcgatg caaaaa                                                       16

<210> SEQ ID NO 39
<211> LENGTH: 17
<212> TYPE: DNA
<213> ORGANISM: artificial sequence
<220> FEATURE:
<223> OTHER INFORMATION: D35core-dAs5
<220> FEATURE:
<221> NAME/KEY: phosphorothioate linkage
<222> LOCATION: (12)..(16)

<400> SEQUENCE: 39
tgcatcgatg caaaaaa                                                      17

<210> SEQ ID NO 40
<211> LENGTH: 18
<212> TYPE: DNA
<213> ORGANISM: artificial sequence
```

```
<220> FEATURE:
<223> OTHER INFORMATION: D35core-dAs6
<220> FEATURE:
<221> NAME/KEY: phosphorothioate linkage
<222> LOCATION: (12)..(17)

<400> SEQUENCE: 40
tgcatcgatg caaaaaaa                                                 18

<210> SEQ ID NO 41
<211> LENGTH: 19
<212> TYPE: DNA
<213> ORGANISM: artificial sequence
<220> FEATURE:
<223> OTHER INFORMATION: D35core-dAs7
<220> FEATURE:
<221> NAME/KEY: phosphorothioate linkage
<222> LOCATION: (12)..(18)

<400> SEQUENCE: 41
tgcatcgatg caaaaaaaa                                                19

<210> SEQ ID NO 42
<211> LENGTH: 20
<212> TYPE: DNA
<213> ORGANISM: artificial sequence
<220> FEATURE:
<223> OTHER INFORMATION: D35core-dAs8
<220> FEATURE:
<221> NAME/KEY: phosphorothioate linkage
<222> LOCATION: (12)..(19)

<400> SEQUENCE: 42
tgcatcgatg caaaaaaaaa                                               20

<210> SEQ ID NO 43
<211> LENGTH: 21
<212> TYPE: DNA
<213> ORGANISM: artificial sequence
<220> FEATURE:
<223> OTHER INFORMATION: D35core-dAs9
<220> FEATURE:
<221> NAME/KEY: phosphorothioate linkage
<222> LOCATION: (12)..(20)

<400> SEQUENCE: 43
tgcatcgatg caaaaaaaaa a                                             21

<210> SEQ ID NO 44
<211> LENGTH: 22
<212> TYPE: DNA
<213> ORGANISM: artificial sequence
<220> FEATURE:
<223> OTHER INFORMATION: D35core-dAs10
<220> FEATURE:
<221> NAME/KEY: phosphorothioate linkage
<222> LOCATION: (12)..(21)

<400> SEQUENCE: 44
tgcatcgatg caaaaaaaaa aa                                            22

<210> SEQ ID NO 45
<211> LENGTH: 32
<212> TYPE: DNA
<213> ORGANISM: artificial sequence
<220> FEATURE:
<223> OTHER INFORMATION: D35core-dAs20
<220> FEATURE:
<221> NAME/KEY: phosphorothioate linkage
```

```
<222> LOCATION: (12)..(31)

<400> SEQUENCE: 45
tgcatcgatg caaaaaaaaa aaaaaaaaaa aa                              32

<210> SEQ ID NO 46
<211> LENGTH: 72
<212> TYPE: DNA
<213> ORGANISM: artificial sequence
<220> FEATURE:
<223> OTHER INFORMATION: D35core-dAs60
<220> FEATURE:
<221> NAME/KEY: phosphorothioate linkage
<222> LOCATION: (12)..(71)

<400> SEQUENCE: 46
tgcatcgatg caaaaaaaaa aaaaaaaaaa aaaaaaaaaa aaaaaaaaaa aaaaaaaaaa    60
aaaaaaaaaa aa                                                   72

<210> SEQ ID NO 47
<211> LENGTH: 92
<212> TYPE: DNA
<213> ORGANISM: artificial sequence
<220> FEATURE:
<223> OTHER INFORMATION: D35core-dAs80
<220> FEATURE:
<221> NAME/KEY: phosphorothioate linkage
<222> LOCATION: (12)..(91)

<400> SEQUENCE: 47
tgcatcgatg caaaaaaaaa aaaaaaaaaa aaaaaaaaaa aaaaaaaaaa aaaaaaaaaa    60
aaaaaaaaaa aaaaaaaaaa aaaaaaaaaa aa                             92

<210> SEQ ID NO 48
<211> LENGTH: 112
<212> TYPE: DNA
<213> ORGANISM: artificial sequence
<220> FEATURE:
<223> OTHER INFORMATION: D35core-dAs100
<220> FEATURE:
<221> NAME/KEY: phosphorothioate linkage
<222> LOCATION: (12)..(111)

<400> SEQUENCE: 48
tgcatcgatg caaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aa       112

<210> SEQ ID NO 49
<211> LENGTH: 52
<212> TYPE: DNA
<213> ORGANISM: artificial sequence
<220> FEATURE:
<223> OTHER INFORMATION: D35core-dAs40(S100%)
<220> FEATURE:
<221> NAME/KEY: phosphorothioate linkage
<222> LOCATION: (12)..(51)

<400> SEQUENCE: 49
tgcatcgatg caaaaaaaaa aaaaaaaaaa aaaaaaaaaa aaaaaaaaaa aa       52

<210> SEQ ID NO 50
<211> LENGTH: 52
<212> TYPE: DNA
<213> ORGANISM: artificial sequence
<220> FEATURE:
<223> OTHER INFORMATION: D35core-dAs40(S50%)
```

<220> FEATURE:
<221> NAME/KEY: phosphorothioate linkage
<222> LOCATION: (12)..(12)
<220> FEATURE:
<221> NAME/KEY: phosphorothioate linkage
<222> LOCATION: (14)..(14)
<220> FEATURE:
<221> NAME/KEY: phosphorothioate linkage
<222> LOCATION: (16)..(16)
<220> FEATURE:
<221> NAME/KEY: phosphorothioate linkage
<222> LOCATION: (18)..(18)
<220> FEATURE:
<221> NAME/KEY: phosphorothioate linkage
<222> LOCATION: (20)..(20)
<220> FEATURE:
<221> NAME/KEY: phosphorothioate linkage
<222> LOCATION: (22)..(22)
<220> FEATURE:
<221> NAME/KEY: phosphorothioate linkage
<222> LOCATION: (24)..(24)
<220> FEATURE:
<221> NAME/KEY: phosphorothioate linkage
<222> LOCATION: (26)..(26)
<220> FEATURE:
<221> NAME/KEY: phosphorothioate linkage
<222> LOCATION: (28)..(28)
<220> FEATURE:
<221> NAME/KEY: phosphorothioate linkage
<222> LOCATION: (30)..(30)
<220> FEATURE:
<221> NAME/KEY: phosphorothioate linkage
<222> LOCATION: (32)..(32)
<220> FEATURE:
<221> NAME/KEY: phosphorothioate linkage
<222> LOCATION: (34)..(34)
<220> FEATURE:
<221> NAME/KEY: phosphorothioate linkage
<222> LOCATION: (36)..(36)
<220> FEATURE:
<221> NAME/KEY: phosphorothioate linkage
<222> LOCATION: (38)..(38)
<220> FEATURE:
<221> NAME/KEY: phosphorothioate linkage
<222> LOCATION: (40)..(40)
<220> FEATURE:
<221> NAME/KEY: phosphorothioate linkage
<222> LOCATION: (42)..(42)
<220> FEATURE:
<221> NAME/KEY: phosphorothioate linkage
<222> LOCATION: (44)..(44)
<220> FEATURE:
<221> NAME/KEY: phosphorothioate linkage
<222> LOCATION: (46)..(46)
<220> FEATURE:
<221> NAME/KEY: phosphorothioate linkage
<222> LOCATION: (48)..(48)
<220> FEATURE:
<221> NAME/KEY: phosphorothioate linkage
<222> LOCATION: (50)..(50)

<400> SEQUENCE: 50
tgcatcgatg caaaaaaaaa aaaaaaaaaa aaaaaaaaaa aaaaaaaaaa aa        52

<210> SEQ ID NO 51
<211> LENGTH: 52
<212> TYPE: DNA
<213> ORGANISM: artificial sequence
<220> FEATURE:
<223> OTHER INFORMATION: D35core-dAs40(S35%)
<220> FEATURE:
<221> NAME/KEY: phosphorothioate linkage
<222> LOCATION: (12)..(12)
<220> FEATURE:
<221> NAME/KEY: phosphorothioate linkage
<222> LOCATION: (15)..(15)
<220> FEATURE:

```
<221> NAME/KEY: phosphorothioate linkage
<222> LOCATION: (18)..(18)
<220> FEATURE:
<221> NAME/KEY: phosphorothioate linkage
<222> LOCATION: (21)..(21)
<220> FEATURE:
<221> NAME/KEY: phosphorothioate linkage
<222> LOCATION: (24)..(24)
<220> FEATURE:
<221> NAME/KEY: phosphorothioate linkage
<222> LOCATION: (27)..(27)
<220> FEATURE:
<221> NAME/KEY: phosphorothioate linkage
<222> LOCATION: (30)..(30)
<220> FEATURE:
<221> NAME/KEY: phosphorothioate linkage
<222> LOCATION: (33)..(33)
<220> FEATURE:
<221> NAME/KEY: phosphorothioate linkage
<222> LOCATION: (36)..(36)
<220> FEATURE:
<221> NAME/KEY: phosphorothioate linkage
<222> LOCATION: (39)..(39)
<220> FEATURE:
<221> NAME/KEY: phosphorothioate linkage
<222> LOCATION: (42)..(42)
<220> FEATURE:
<221> NAME/KEY: phosphorothioate linkage
<222> LOCATION: (45)..(45)
<220> FEATURE:
<221> NAME/KEY: phosphorothioate linkage
<222> LOCATION: (48)..(48)

<400> SEQUENCE: 51
tgcatcgatg caaaaaaaaa aaaaaaaaaa aaaaaaaaaa aaaaaaaaaa aa      52

<210> SEQ ID NO 52
<211> LENGTH: 52
<212> TYPE: DNA
<213> ORGANISM: artificial sequence
<220> FEATURE:
<223> OTHER INFORMATION: D35core-dAs40(S25%)
<220> FEATURE:
<221> NAME/KEY: phosphorothioate linkage
<222> LOCATION: (12)..(12)
<220> FEATURE:
<221> NAME/KEY: phosphorothioate linkage
<222> LOCATION: (16)..(16)
<220> FEATURE:
<221> NAME/KEY: phosphorothioate linkage
<222> LOCATION: (20)..(20)
<220> FEATURE:
<221> NAME/KEY: phosphorothioate linkage
<222> LOCATION: (24)..(24)
<220> FEATURE:
<221> NAME/KEY: phosphorothioate linkage
<222> LOCATION: (28)..(28)
<220> FEATURE:
<221> NAME/KEY: phosphorothioate linkage
<222> LOCATION: (32)..(32)
<220> FEATURE:
<221> NAME/KEY: phosphorothioate linkage
<222> LOCATION: (36)..(36)
<220> FEATURE:
<221> NAME/KEY: phosphorothioate linkage
<222> LOCATION: (40)..(40)
<220> FEATURE:
<221> NAME/KEY: phosphorothioate linkage
<222> LOCATION: (44)..(44)
<220> FEATURE:
<221> NAME/KEY: phosphorothioate linkage
<222> LOCATION: (48)..(48)

<400> SEQUENCE: 52
tgcatcgatg caaaaaaaaa aaaaaaaaaa aaaaaaaaaa aaaaaaaaaa aa      52
```

```
<210> SEQ ID NO 53
<211> LENGTH: 52
<212> TYPE: DNA
<213> ORGANISM: artificial sequence
<220> FEATURE:
<223> OTHER INFORMATION: D35core-dAs40(S20%)
<220> FEATURE:
<221> NAME/KEY: phosphorothioate linkage
<222> LOCATION: (12)..(12)
<220> FEATURE:
<221> NAME/KEY: phosphorothioate linkage
<222> LOCATION: (17)..(17)
<220> FEATURE:
<221> NAME/KEY: phosphorothioate linkage
<222> LOCATION: (22)..(22)
<220> FEATURE:
<221> NAME/KEY: phosphorothioate linkage
<222> LOCATION: (27)..(27)
<220> FEATURE:
<221> NAME/KEY: phosphorothioate linkage
<222> LOCATION: (32)..(32)
<220> FEATURE:
<221> NAME/KEY: phosphorothioate linkage
<222> LOCATION: (37)..(37)
<220> FEATURE:
<221> NAME/KEY: phosphorothioate linkage
<222> LOCATION: (42)..(42)
<220> FEATURE:
<221> NAME/KEY: phosphorothioate linkage
<222> LOCATION: (47)..(47)

<400> SEQUENCE: 53
tgcatcgatg caaaaaaaaa aaaaaaaaaa aaaaaaaaaa aaaaaaaaaa aa          52

<210> SEQ ID NO 54
<211> LENGTH: 52
<212> TYPE: DNA
<213> ORGANISM: artificial sequence
<220> FEATURE:
<223> OTHER INFORMATION: D35core-dAs40(S15%)
<220> FEATURE:
<221> NAME/KEY: phosphorothioate linkage
<222> LOCATION: (12)..(12)
<220> FEATURE:
<221> NAME/KEY: phosphorothioate linkage
<222> LOCATION: (19)..(19)
<220> FEATURE:
<221> NAME/KEY: phosphorothioate linkage
<222> LOCATION: (26)..(26)
<220> FEATURE:
<221> NAME/KEY: phosphorothioate linkage
<222> LOCATION: (33)..(33)
<220> FEATURE:
<221> NAME/KEY: phosphorothioate linkage
<222> LOCATION: (40)..(40)
<220> FEATURE:
<221> NAME/KEY: phosphorothioate linkage
<222> LOCATION: (47)..(47)

<400> SEQUENCE: 54
tgcatcgatg caaaaaaaaa aaaaaaaaaa aaaaaaaaaa aaaaaaaaaa aa          52

<210> SEQ ID NO 55
<211> LENGTH: 20
<212> TYPE: DNA
<213> ORGANISM: artificial sequence
<220> FEATURE:
<223> OTHER INFORMATION: A2216
<220> FEATURE:
<221> NAME/KEY: phosphorothioate linkage
<222> LOCATION: (1)..(2)
<220> FEATURE:
<221> NAME/KEY: phosphorothioate linkage
<222> LOCATION: (14)..(19)
```

```
<400> SEQUENCE: 55
gggggacgat cgtcggggg                                          20

<210> SEQ ID NO 56
<211> LENGTH: 10
<212> TYPE: DNA
<213> ORGANISM: artificial sequence
<220> FEATURE:
<223> OTHER INFORMATION: A2216core

<400> SEQUENCE: 56
gacgatcgtc                                                    10

<210> SEQ ID NO 57
<211> LENGTH: 21
<212> TYPE: DNA
<213> ORGANISM: artificial sequence
<220> FEATURE:
<223> OTHER INFORMATION: A2336
<220> FEATURE:
<221> NAME/KEY: phosphorothioate linkage
<222> LOCATION: (1)..(3)
<220> FEATURE:
<221> NAME/KEY: phosphorothioate linkage
<222> LOCATION: (15)..(20)

<400> SEQUENCE: 57
ggggacgacg tcgtggggggg g                                      21

<210> SEQ ID NO 58
<211> LENGTH: 10
<212> TYPE: DNA
<213> ORGANISM: artificial sequence
<220> FEATURE:
<223> OTHER INFORMATION: A2336core

<400> SEQUENCE: 58
acgacgtcgt                                                    10

<210> SEQ ID NO 59
<211> LENGTH: 24
<212> TYPE: DNA
<213> ORGANISM: artificial sequence
<220> FEATURE:
<223> OTHER INFORMATION: B2006(PS)
<220> FEATURE:
<221> NAME/KEY: phosphorothioate linkage
<222> LOCATION: (1)..(23)

<400> SEQUENCE: 59
tcgtcgtttt gtcgttttgt cgtt                                    24

<210> SEQ ID NO 60
<211> LENGTH: 24
<212> TYPE: DNA
<213> ORGANISM: artificial sequence
<220> FEATURE:
<223> OTHER INFORMATION: B2006(PO)

<400> SEQUENCE: 60
tcgtcgtttt gtcgttttgt cgtt                                    24

<210> SEQ ID NO 61
<211> LENGTH: 22
<212> TYPE: DNA
<213> ORGANISM: artificial sequence
```

```
<220> FEATURE:
<223> OTHER INFORMATION: C2395(PS)
<220> FEATURE:
<221> NAME/KEY: phosphorothioate linkage
<222> LOCATION: (1)..(21)

<400> SEQUENCE: 61
tcgtcgtttt cggcgcgcgc cg                                              22

<210> SEQ ID NO 62
<211> LENGTH: 22
<212> TYPE: DNA
<213> ORGANISM: artificial sequence
<220> FEATURE:
<223> OTHER INFORMATION: C2395(PO)

<400> SEQUENCE: 62
tcgtcgtttt cggcgcgcgc cg                                              22

<210> SEQ ID NO 63
<211> LENGTH: 23
<212> TYPE: DNA
<213> ORGANISM: artificial sequence
<220> FEATURE:
<223> OTHER INFORMATION: P21889(PS)
<220> FEATURE:
<221> NAME/KEY: phosphorothioate linkage
<222> LOCATION: (1)..(22)

<400> SEQUENCE: 63
tcgtcgacga tcggcgcgcg ccg                                             23

<210> SEQ ID NO 64
<211> LENGTH: 23
<212> TYPE: DNA
<213> ORGANISM: artificial sequence
<220> FEATURE:
<223> OTHER INFORMATION: P21889(PO)

<400> SEQUENCE: 64
tcgtcgacga tcggcgcgcg ccg                                             23

<210> SEQ ID NO 65
<211> LENGTH: 20
<212> TYPE: DNA
<213> ORGANISM: artificial sequence
<220> FEATURE:
<223> OTHER INFORMATION: full length A2216

<400> SEQUENCE: 65
gggggacgat cgtcgggggg                                                 20

<210> SEQ ID NO 66
<211> LENGTH: 21
<212> TYPE: DNA
<213> ORGANISM: artificial sequence
<220> FEATURE:
<223> OTHER INFORMATION: full length A2336

<400> SEQUENCE: 66
ggggacgacg tcgtgggggg g                                               21

<210> SEQ ID NO 67
<211> LENGTH: 24
<212> TYPE: DNA
<213> ORGANISM: artificial sequence
<220> FEATURE:
```

```
<223> OTHER INFORMATION: CPG 7909
<220> FEATURE:
<221> NAME/KEY: phosphorothioate linkage
<222> LOCATION: (1)..(23)

<400> SEQUENCE: 67
tcgtcgtttt gtcgttttgt cgtt                                    24

<210> SEQ ID NO 68
<211> LENGTH: 24
<212> TYPE: DNA
<213> ORGANISM: artificial sequence
<220> FEATURE:
<223> OTHER INFORMATION: PF-3512676
<220> FEATURE:
<221> NAME/KEY: phosphorothioate linkage
<222> LOCATION: (1)..(23)

<400> SEQUENCE: 68
tcgtcgtttt gtcgttttgt cgtt                                    24

<210> SEQ ID NO 69
<211> LENGTH: 30
<212> TYPE: DNA
<213> ORGANISM: artificial sequence
<220> FEATURE:
<223> OTHER INFORMATION: CYT003-QBG10

<400> SEQUENCE: 69
gggggggggg gacgatcgtc gggggggggg                              30

<210> SEQ ID NO 70
<211> LENGTH: 22
<212> TYPE: DNA
<213> ORGANISM: artificial sequence
<220> FEATURE:
<223> OTHER INFORMATION: 1018 ISS
<220> FEATURE:
<221> NAME/KEY: phosphorothioate linkage
<222> LOCATION: (1)..(21)

<400> SEQUENCE: 70
tgactgtgaa cgttcgagat ga                                      22

<210> SEQ ID NO 71
<211> LENGTH: 19
<212> TYPE: DNA
<213> ORGANISM: artificial sequence
<220> FEATURE:
<223> OTHER INFORMATION: Kappaproct (DIMS 0150)
<220> FEATURE:
<221> NAME/KEY: phosphorothioate linkage
<222> LOCATION: (1)..(3)
<220> FEATURE:
<221> NAME/KEY: phosphorothioate linkage
<222> LOCATION: (16)..(18)

<400> SEQUENCE: 71
ggaacagttc gtccatggc                                          19

<210> SEQ ID NO 72
<211> LENGTH: 60
<212> TYPE: DNA
<213> ORGANISM: artificial sequence
<220> FEATURE:
<223> OTHER INFORMATION: D35-dNs40
<220> FEATURE:
<221> NAME/KEY: phosphorothioate linkage
<222> LOCATION: (1)..(2)
```

```
<220> FEATURE:
<221> NAME/KEY: phosphorothioate linkage
<222> LOCATION: (18)..(59)
<220> FEATURE:
<221> NAME/KEY: misc_feature
<222> LOCATION: (21)..(60)
<223> OTHER INFORMATION: n is a, c, g, t or u

<400> SEQUENCE: 72
ggtgcatcga tgcaggggggg nnnnnnnnnn nnnnnnnnnn nnnnnnnnnn nnnnnnnnnn      60

<210> SEQ ID NO 73
<211> LENGTH: 20
<212> TYPE: DNA
<213> ORGANISM: artificial sequence
<220> FEATURE:
<223> OTHER INFORMATION: D35beta
<220> FEATURE:
<221> NAME/KEY: phosphorothioate linkage
<222> LOCATION: (1)..(2)
<220> FEATURE:
<221> NAME/KEY: phosphorothioate linkage
<222> LOCATION: (18)..(19)

<400> SEQUENCE: 73
ggtgcatcga tgcaggggggg                                                  20

<210> SEQ ID NO 74
<211> LENGTH: 60
<212> TYPE: DNA
<213> ORGANISM: artificial sequence
<220> FEATURE:
<223> OTHER INFORMATION: dAs40-D35
<220> FEATURE:
<221> NAME/KEY: phosphorothioate linkage
<222> LOCATION: (1)..(41)
<220> FEATURE:
<221> NAME/KEY: phosphorothioate linkage
<222> LOCATION: (58)..(59)

<400> SEQUENCE: 74
aaaaaaaaaa aaaaaaaaaa aaaaaaaaaa aaaaaaaaaa ggtgcatcga tgcaggggggg      60

<210> SEQ ID NO 75
<211> LENGTH: 80
<212> TYPE: DNA
<213> ORGANISM: artificial sequence
<220> FEATURE:
<223> OTHER INFORMATION: D35-dAs40-D35
<220> FEATURE:
<221> NAME/KEY: phosphorothioate linkage
<222> LOCATION: (1)..(1)
<220> FEATURE:
<221> NAME/KEY: phosphorothioate linkage
<222> LOCATION: (18)..(61)
<220> FEATURE:
<221> NAME/KEY: phosphorothioate linkage
<222> LOCATION: (78)..(79)

<400> SEQUENCE: 75
ggtgcatcga tgcaggggggg aaaaaaaaaa aaaaaaaaaa aaaaaaaaaa aaaaaaaaaa      60
ggtgcatcga tgcaggggggg                                                  80

<210> SEQ ID NO 76
<211> LENGTH: 60
<212> TYPE: DNA
<213> ORGANISM: artificial sequence
<220> FEATURE:
<223> OTHER INFORMATION: A2216-dAs40
<220> FEATURE:
```

```
<221> NAME/KEY: phosphorothioate linkage
<222> LOCATION: (1)..(2)
<220> FEATURE:
<221> NAME/KEY: phosphorothioate linkage
<222> LOCATION: (14)..(19)
<220> FEATURE:
<221> NAME/KEY: phosphorothioate linkage
<222> LOCATION: (21)..(59)

<400> SEQUENCE: 76 ggggacgat cgtcggggg aaaaaaaaaa aaaaaaaaaa aaaaaaaaaa aaaaaaaaaa    60

<210> SEQ ID NO 77
<211> LENGTH: 50
<212> TYPE: DNA
<213> ORGANISM: artificial sequence
<220> FEATURE:
<223> OTHER INFORMATION: A2216core-dAs40
<220> FEATURE:
<221> NAME/KEY: phosphorothioate linkage
<222> LOCATION: (11)..(49)

<400> SEQUENCE: 77
gacgatcgtc aaaaaaaaaa aaaaaaaaaa aaaaaaaaaa aaaaaaaaaa              50

<210> SEQ ID NO 78
<211> LENGTH: 61
<212> TYPE: DNA
<213> ORGANISM: artificial sequence
<220> FEATURE:
<223> OTHER INFORMATION: A2336-dAs40
<220> FEATURE:
<221> NAME/KEY: phosphorothioate linkage
<222> LOCATION: (1)..(3)
<220> FEATURE:
<221> NAME/KEY: phosphorothioate linkage
<222> LOCATION: (15)..(20)
<220> FEATURE:
<221> NAME/KEY: phosphorothioate linkage
<222> LOCATION: (22)..(60)

<400> SEQUENCE: 78
ggggacgacg tcgtgggggg gaaaaaaaaa aaaaaaaaaa aaaaaaaaaa aaaaaaaaaa    60
a                                                                   61

<210> SEQ ID NO 79
<211> LENGTH: 50
<212> TYPE: DNA
<213> ORGANISM: artificial sequence
<220> FEATURE:
<223> OTHER INFORMATION: A2336core-dAs40
<220> FEATURE:
<221> NAME/KEY: phosphorothioate linkage
<222> LOCATION: (21)..(49)

<400> SEQUENCE: 79
acgacgtcgt aaaaaaaaaa aaaaaaaaaa aaaaaaaaaa aaaaaaaaaa              50

<210> SEQ ID NO 80
<211> LENGTH: 64
<212> TYPE: DNA
<213> ORGANISM: artificial sequence
<220> FEATURE:
<223> OTHER INFORMATION: B2006(PS)-dAs40
<220> FEATURE:
<221> NAME/KEY: phosphorothioate linkage
<222> LOCATION: (1)..(23)
<220> FEATURE:
<221> NAME/KEY: phosphorothioate linkage
<222> LOCATION: (25)..(63)
```

-continued

<400> SEQUENCE: 80
tcgtcgtttt gtcgttttgt cgttaaaaaa aaaaaaaaaa aaaaaaaaaa aaaaaaaaaa    60
aaaa    64

<210> SEQ ID NO 81
<211> LENGTH: 64
<212> TYPE: DNA
<213> ORGANISM: artificial sequence
<220> FEATURE:
<223> OTHER INFORMATION: B2006(PO)-dAs40
<220> FEATURE:
<221> NAME/KEY: phosphorothioate linkage
<222> LOCATION: (25)..(63)

<400> SEQUENCE: 81
tcgtcgtttt gtcgttttgt cgttaaaaaa aaaaaaaaaa aaaaaaaaaa aaaaaaaaaa    60
aaaa    64

<210> SEQ ID NO 82
<211> LENGTH: 62
<212> TYPE: DNA
<213> ORGANISM: artificial sequence
<220> FEATURE:
<223> OTHER INFORMATION: C2395(PS)-dAs40
<220> FEATURE:
<221> NAME/KEY: phosphorothioate linkage
<222> LOCATION: (1)..(21)
<220> FEATURE:
<221> NAME/KEY: phosphorothioate linkage
<222> LOCATION: (23)..(61)

<400> SEQUENCE: 82
tcgtcgtttt cggcgcgcgc cgaaaaaaaa aaaaaaaaaa aaaaaaaaaa aaaaaaaaaa    60
aa    62

<210> SEQ ID NO 83
<211> LENGTH: 62
<212> TYPE: DNA
<213> ORGANISM: artificial sequence
<220> FEATURE:
<223> OTHER INFORMATION: C2395(PO)-dAs40
<220> FEATURE:
<221> NAME/KEY: phosphorothioate linkage
<222> LOCATION: (23)..(61)

<400> SEQUENCE: 83
tcgtcgtttt cggcgcgcgc cgaaaaaaaa aaaaaaaaaa aaaaaaaaaa aaaaaaaaaa    60
aa    62

<210> SEQ ID NO 84
<211> LENGTH: 63
<212> TYPE: DNA
<213> ORGANISM: artificial sequence
<220> FEATURE:
<223> OTHER INFORMATION: P21889(PS)-dAs40
<220> FEATURE:
<221> NAME/KEY: phosphorothioate linkage
<222> LOCATION: (1)..(22)
<220> FEATURE:
<221> NAME/KEY: phosphorothioate linkage
<222> LOCATION: (24)..(62)

<400> SEQUENCE: 84
tcgtcgacga tcggcgcgcg ccgaaaaaaa aaaaaaaaaa aaaaaaaaaa aaaaaaaaaa    60

```
aaa                                                                  63

<210> SEQ ID NO 85
<211> LENGTH: 63
<212> TYPE: DNA
<213> ORGANISM: artificial sequence
<220> FEATURE:
<223> OTHER INFORMATION: P21889(PO)-dAs40
<220> FEATURE:
<221> NAME/KEY: phosphorothioate linkage
<222> LOCATION: (24)..(62)

<400> SEQUENCE: 85
tcgtcgacga tcggcgcgcg ccgaaaaaaa aaaaaaaaaa aaaaaaaaaa aaaaaaaaaa    60
aaa                                                                  63
```

NON-AGGREGATING IMMUNOSTIMULATORY OLIGONUCLEOTIDES

TECHNICAL FIELD

Statement Regarding Sequence Listing

The Sequence Listing associated with this application is provided in text format in lieu of a paper copy, and is hereby incorporated by reference into the specification. The name of the text file containing the Sequence Listing is 690188_406USPC_SEQUENCE_LISTING.txt. The text file is 26.6 KB, was created on Jun. 22, 2017, and is being submitted electronically via EFS-Web.

The present invention relates to a non-aggregated immunostimulatory oligonucleotide, and more specifically to an agent for delivery of a non-aggregated CpG immunostimulatory oligonucleotide.

BACKGROUND ART

Immunostimulatory oligonucleotides have expectations as vaccine adjuvants that elicit an innate immune response in a Toll-like receptor (TLR) 9 dependent manner and enhance the immunological effect of a vaccine by co-administration thereof with a vaccine antigen, or as a immunoregulatory agent using self-elicited innate immune responses. Immunostimulatory oligonucleotides are roughly categorized into two types, of which the K type is known to be soluble in saline and to mainly induce interleukin (IL)-6 production. Adaption thereof into clinical use is already ongoing as a promising nucleic acid medicament. The other type, i.e., D type, is known to be insoluble in saline and to mainly induce IFN-α production, thus having biological activity that differs from that of K type. However, adaption thereof into clinical use has not advanced due to it being insoluble in saline.

The present invention has developed a D type immunostimulatory oligonucleotide that is soluble in saline. This is expected to promote clinical application of D type immunostimulatory oligonucleotides.

Immunostimulatory CpG oligonucleotides (ODN) has been developed and utilized as TLR9 dependent innate immune-activating agents and vaccine adjuvants for over 10 years [Non Patent Literature 1]. Immunostimulatory ODNs can be classified into four different types (or classes) based on the backbone and sequence characteristics thereof: A/D. B/K, C, and P type ODNs [Non Patent Literature 2; Non Patent Literature 3]. A/D type ODNs (mostly phosphodiester backbone with a poly-G tail at the 3' end) mainly stimulate the production of interferon (IFN)-α from plasmacytoid dendritic cells (pDC). B/K type ODNs (all phosphorothioate backbone) activates IL-6 and B cell production. Although C type ODNs can stimulate the production of both IFN-α and IL-6, IFN-α is induced by C type ODN at a lower extent than by A/D type ODN. Another ODN, i.e., P type ODN, has been discovered recently [Non Patent Literature 4]. P type ODNs (all phosphorothioate backbone) comprise two palindromic sequences with a cytokine profile that is similar to C type ODNs, but induce higher IFN-α production than C type ODNs [Non Patent Literature 4].

While many different immunostimulatory ODNs have been developed, the most characteristic difference among such ODNs is the INF-α induction profile thereof. In terms of the above, A/D type (high IFN-α profile) and B/K type (low IFN-α high IL-6 profile) ODNs are considered as two distinct typical prototypes of immunostimulatory ODNs [Non Patent Literature 5]. Recent microarray studies have also confirmed overlapping but different gene signatures between A/D type ODNs and B/K type ODNs [Non Patent Literature 6]. A/D type ODNs were primarily characterized by sustained induction of type I IFN, while B/K type ODNs induced many genes that were significantly associated with resistance to bacterial infections such as IL-1β and IL-6 [Non Patent Literature 6]. Such differences in vitro profiles may reflect the differences observed in vivo when these ODNs are used as a vaccine adjuvant or as a single agent immunotherapeutic agent. For malaria vaccines, K3 (B/K type ODN) exhibited better adjuvanticity than D35 (A/D type ODN) with respect to antibody production when added to SE36/AHG immunization of a cynomolgus monkey [Non Patent Literature 7]. However, A/D type ODNs induced a better protective immune response than B/K type ODNs, with a heat-sterilized Leishmania/AHG vaccine in rhesus monkey [Non Patent Literature 8]. Similarly, A/D type ODNs also exhibited a better potential than B/K type ODNs in both healthy rhesus monkey and SIV-infected rhesus monkey models as a single therapeutic agent for leishmaniasis [Non Patent Literature 9]. Interestingly, administration of B/K type ODNs exacerbated the pathological condition of skin leishmaniasis in this model [Non Patent Literature 9].

Potent INF-α induction by A/D type ODNs is closely related to the higher order structure of this type of ODNs. A poly-G tail of A/D type ODNs form a G-quadruplex DNA structure in a salt solution, resulting in nanoparticles/aggregate formation [Non Patent literature 10; Non Patent literature 11; Non Patent literature 12; and Non Patent literature 13]. Similarly, INF-α inducing P type ODNs formed a dimeric structure or an aggregate [Non Patent Literature 14]. Aggregate formation has been reported frequently as essential for high INF-α production by A/D type ODNs [Non Patent literature 12; and Non Patent literature 13]. This is because voluntary ODN multimerization leads to uncontrolled aggregation and precipitation, resulting in large product-by-product differences or difficulty in administration. To overcome such a problem, an attempt has been made to introduce a thermolytic protecting group to A/D type ODNs [Non Patent literature 15 and Non Patent literature 16]. Although aggregate formation in saline prior to administration is prevented by such a modification, temperature dependent cleavage of a protecting group allows G-quadruplex formation after in vivo administration [Non Patent Literatures 15 and 16]. Such thermolytic pro-D type ODN strategy is a promising method for clinically applicable A/D type ODNs, but it is necessary to evaluate the feasibility of the clinical application thereof. Currently, a clinical trial in humans has not been reported.

CITATION LIST

Non Patent Literature

[NPL 1] Bode C et al., (2011) Expert Review of Vaccines 10: 499-511.
[NPL 2] Vollmer J, Krieg A M (2009) Adv Drug Deliv Rev 61: 195-204.
[NPL 3] Klinman D M (2004) Nat Rev Immunol 4: 249-258.
[NPL 4] Samulowitz U et al., (2010) Oligonucleotides 20: 93-101.
[NPL 5] Verthelyi D et al., (2001) J Immunol 166: 2372-2377.

[NPL 6] Steinhagen F et al., (2012) Journal of Leukocyte Biology 92:775-785.]
[NPL 7] Steinhagen F et al., (2012) Journal of Leukocyte Biology 92:775-785.
[NPL 8] Tougan T et al., (2013) Human Vaccines & Immunotherapeutics 9:283-290.
[NPL 9] Verthelyi D et al., (2003) J Immunol 170: 4717-4723.
[NPL 10] Costa L T et al., (2004) Biochemical and Biophysical Research Communications 313:1065-1072.
[NPL 11] Klein D C et al., (2010) Ultramicroscopy 110: 689-693.
[NPL 12] Kerkmann M et al., (2005) J Biol Chem 280: 8086-8093.
[NPL 13] Wu C C et al., (2004) J Biol Chem 279: 33071-33078.
[NPL 14] Samulowitz U et al., (2010) Oligonucleotides 20: 93-101.]
[NPL 15] Puig M et al., (2006) Nucleic Acids Res 34: 6488-6495.
[NPL 16] Grajkowski A et al., (2005) Nucleic Acids Res 33: 3550-3560.

SUMMARY OF INVENTION

Solution to Problem

The inventors have completed the present invention based on the findings from developing a non-aggregated A/D type ODN by modifying an exemplary immunostimulatory oligonucleotide D35, and by examining the physical and biological properties thereof. The present invention was also completed by the inventors based on the finding that a simple modification to D35, such as the addition of a phosphorothioate polydeoxynucleotide to the 3' end, strongly prevents aggregate formation in saline, but maintains the property of inducing IFN-α at a high level.

A detailed example is provided. The inventors used immunostimulatory oligonucleotides such as D35, which were selected as a typical example of D type CpG-ODNs with the strongest activity, as a starting material. D35 exhibits preferential induction of IFN-α, but quickly aggregates to form a semi-transparent gel when dissolved in a salt solution such as saline. For this reason, D35 was found to be unsuitable, requiring improvement for actual medical applications of the present invention. The inventors thus examined D35 further and found that the region of consecutive dGs on the 3' end side has a strong effect on gelation in view of the structure of D35. In light of this information, the inventors conceived an idea to replace dG with another nucleic acid and to examine the activity of variants. Replacement of the region with consecutive dG with another nucleic acid resulted in successful prevention of gelation, but independent introduction thereof into cells was no longer possible. In view of the above, the inventors concluded that D type nucleic acid adjuvants can be separated into a unit with IFN-α production inducing activity and a unit exhibiting cell introduction capability and started screening by modifying the gelation factor, the unit with cell introducing capability, to complete the present invention. Thus, the present invention provides the following.

(1) An agent for delivery of an immunostimulatory oligonucleotide nucleic acid medicament, comprising a nucleic acid comprising a phosphorothioated nucleotide.
(2) The agent for delivery of any of the preceding items, wherein the nucleic acid prevents the formation of a high order aggregate due to guanine.
(3) The agent for delivery of any of the preceding items, wherein the phosphorothioated nucleotide content in the nucleic acid is about 25% or greater.
(4) The agent for delivery of any of the preceding items, wherein the phosphorothioated nucleotide content in the nucleic acid is about 33% or greater.
(5) The agent for delivery of any of the preceding items, wherein the phosphorothioated nucleotide content in the nucleic acid is about 50% or greater.
(6) The agent for delivery of any of the preceding items, wherein the phosphorothioated nucleotide content in the nucleic acid is greater than about 50%.
(7) The agent for delivery of any of the preceding items, wherein the nucleic acid has a length of about 5 bases or greater.
(8) The agent for delivery of any of the preceding items, wherein the nucleic acid has a length of about 100 bases or less.
(9) The agent for delivery of any of the preceding items, wherein the nucleic acid has a length of about 9 bases to about 100 bases.
(10) The agent for delivery of any of the preceding items, wherein the agent for delivery is bound to a moiety with biological activity.
(11) The agent for delivery of any of the preceding items, wherein the moiety with biological activity comprises a core moiety with biological activity of an A/D type immunostimulatory oligonucleotide or a full length of a B/K type, C type, or P type immunostimulatory oligonucleotide.
(12) The agent for delivery of any of the preceding items, wherein the moiety with biological activity has a core moiety with biological activity of an A/D type immunostimulatory oligonucleotide.
(13) The agent for delivery of any of the preceding items, wherein the moiety with biological activity comprises a core moiety (TGCATCGATGCA) of a D35 oligonucleotide (SEQ ID NO: 22), a core moiety (GACGATCGTC (SEQ ID NO: 56)) of A2216, or a core moiety (ACGACGTCGT (SEQ ID NO: 58)) of A2336.
(14) An agent for immunostimulation comprising a core moiety with biological activity of an A/D type immunostimulatory oligonucleotide.
(15) The agent for immunostimulation of any of the preceding items, wherein the agent for immunostimulation does not comprise a sequence that is not derived from the core moiety in the A/D type immunostimulatory oligonucleotide.
(16) The agent for immunostimulation of any of the preceding items, wherein the biological activity is interferon (IFN)-α production inducing activity and/or interleukin-6 (IL-6) production inducing activity.
(17) The agent for immunostimulation of any of the preceding items, wherein the core moiety is a full length sequence of A/D type from which consecutive Gs are removed.
(18) The agent for immunostimulation of any of the preceding items, wherein the core moiety comprises a core moiety (TGCATCGATGCA (SEQ ID NO: 22)) of a D35 oligonucleotide, a core moiety (GACGATCGTC (SEQ ID NO: 56)) of A2216, or a core moiety (ACGACGTCGT (SEQ ID NO: 58)) of A2336.
(19) The agent for immunostimulation of any of the preceding items, wherein the core moiety is comprised by a vehicle for cell introduction.

(20) The agent for immunostimulation of any of the preceding items, wherein the vehicle is a liposome or the agent for delivery of any one of items 1 to 13.
(21) An oligonucleotide comprising a full length or a core moiety with biological activity of an immunostimulatory oligonucleotide and a nucleic acid comprising a phosphorothioated nucleotide.
(22) The oligonucleotide of any of the preceding items, wherein the nucleic acid prevents the formation of a multimer due to guanine.
(23) The oligonucleotide of any of the preceding items, wherein the phosphorothioated nucleotide content in the nucleic acid is about 25% or greater.
(24) The oligonucleotide of any of the preceding items, wherein the phosphorothioated nucleotide content in the nucleic acid is about 33% or greater.
(25) The oligonucleotide of any of the preceding items, wherein the phosphorothioated nucleotide content in the nucleic acid is about 50% or greater.
(26) The oligonucleotide of any of the preceding items, wherein the phosphorothioated nucleotide content in the nucleic acid is greater than about 50%.
(27) The oligonucleotide of any of the preceding items, wherein the nucleic acid has a length of about 5 bases or greater.
(28) The oligonucleotide of any of the preceding items, wherein the nucleic acid has a length of about 100 bases or less.
(29) The oligonucleotide of any of the preceding items, wherein the nucleic acid has a length of about 9 bases to about 100 bases.
(30) The oligonucleotide of any of the preceding items, wherein the moiety with biological activity comprises a core moiety with biological activity of an A/D type immunostimulatory oligonucleotide or a full length of a B/K type, C type, or P type immunostimulatory oligonucleotide.
(31) The oligonucleotide of any of the preceding items, wherein the immunostimulatory oligonucleotide is of A/D type, and the biological activity is interferon (IFN)-α production inducing activity and/or interleukin-6 (IL-6) production inducing activity.
(32) The oligonucleotide of any of the preceding items, wherein the core moiety is A/D type from which consecutive Gs are removed.
(33) The oligonucleotide of any of the preceding items, wherein the core moiety comprises a core moiety (TGCATCGATGCA (SEQ ID NO: 22)) of a D35 oligonucleotide, a core moiety (GACGATCGTC (SEQ ID NO: 56)) of A2216, or a core moiety (ACGACGTCGT (SEQ ID NO: 58)) of A2336.
(34) An agent for immunostimulation comprising the oligonucleotide of any one of the preceding items.
(35) The agent for immunostimulation of any of the preceding items, wherein the agent for immunostimulation is for inducing the production of interferon (IFN)-α and/or interleukin-6 (IL-6).
(36) A nucleic acid comprising a phosphorothioated nucleotide for use in the delivery of an immunostimulatory oligonucleotide nucleic acid medicament.
(37) The nucleic acid of item 36, further comprising the feature of one or more of any of items 2 to 13.
(38) A method of delivering an immunostimulatory oligonucleotide nucleic acid medicament, wherein the method comprises binding the immunostimulatory oligonucleotide nucleic acid medicament with a nucleic acid comprising a phosphorothioated nucleotide or the agent for delivery of any one of items 1-13 directly or, for example, via a spacer or the like, for administration to a subject.
(39) The method of item 38, wherein the nucleic acid comprising the phosphorothioated nucleotide further comprises the feature of any one or more of items 1 to 13.
(40) A method of stimulating immunity of a subject, the method comprising administering to the subject an effective amount of the agent for immunostimulation of any one of items 14 to 20, 34, and 35.
(41) Use of the oligonucleotide of any one of items 21 to 33 in the manufacture of an immunostimulatory oligonucleotide nucleic acid medicament.

In the present invention, one or more of the features described above are intended to be provided not only as the explicitly described combinations, but also as other combinations thereof. The additional embodiments and advantages of the present invention are recognized by those skilled in the art by reading the following detailed description, as needed.

Advantageous Effects of Invention

As explained herein, it is understood from the results provided in the present invention that the present invention represented by D35-dAs40, D35core-dAs40, and the like are prototypes of promising non-aggregated A/D type ODNs with an advantage of facilitating drug preparation for clinical applications. It was also discovered that aggregation of immunostimulatory oligonucleotides, such as D35, is suppressed by addition to the 5' end, such that there is expectation for application thereof as medicaments. IL-6 production is also unexpectedly enhanced. This aspect is also expected to be applied to medicaments.

DESCRIPTION OF EMBODIMENTS

Figure 1:
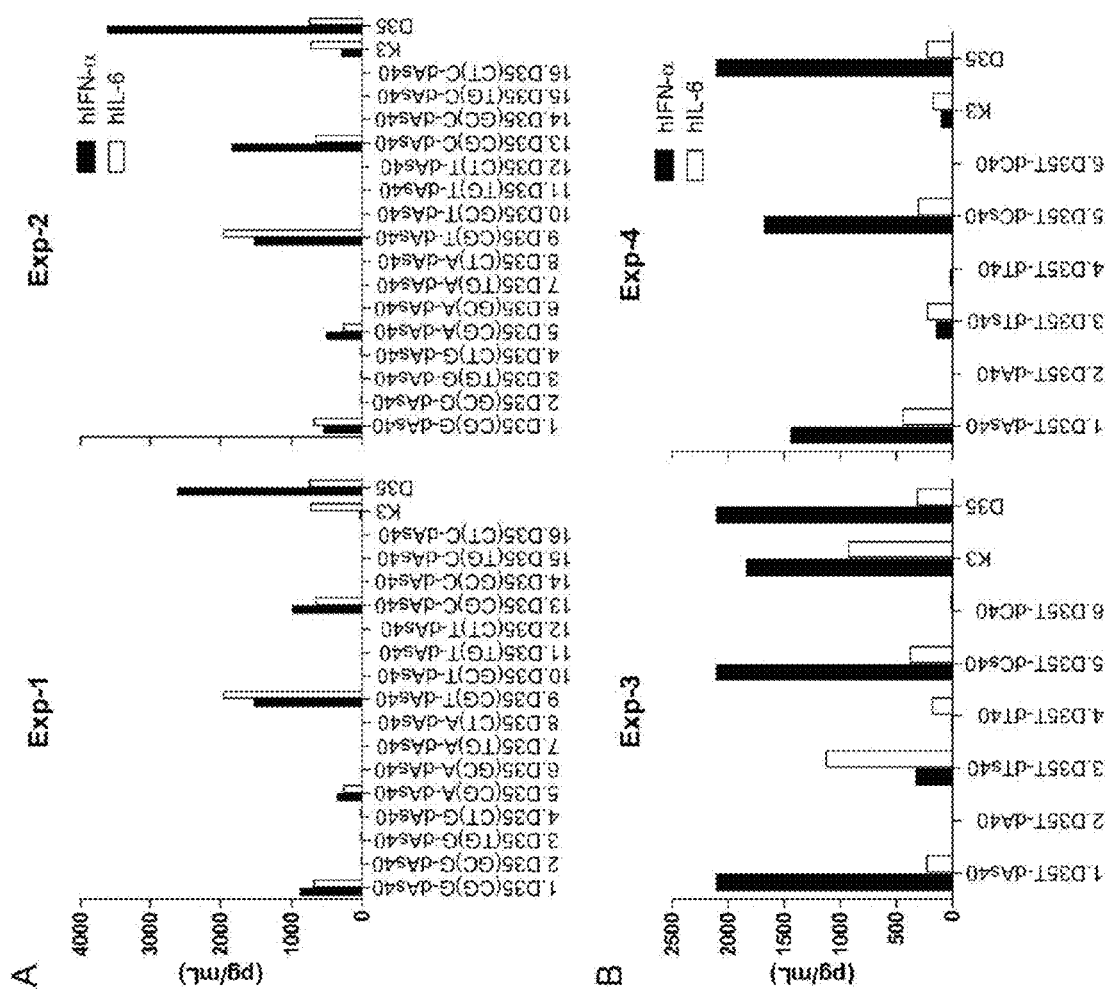
FIG. 1 shows results of screening of human PBMCs using several different polynucleotide tailed A/D type ODNs. Human PBMCs were stimulated for 24 hours with the shown synthetic ODNs (1 µM) (Table 1), and IFN-α and IL-6 production in the supernatant was measured by ELISA. (A) is a graph showing the need for a CpG motif and a guanine hexamer with respect to cytokine secretion from human PBMCs. Both IFN-α and IL-6 were secreted in a CpG motif dependent and guanine hexamer sequence non-dependent manner. (B) is a graph showing the comparison of tail backbones (phosphorothioate or phosphodiester). Cytokine secretion was phosphorothioate 40-mer tail (1, 3, and 5) dependent. ODNs with a phosphodiester 40-mer tail barely exhibited biological activity (2, 4, and 6). The bar graphs show the concentration from a single well for each stimulation. The results are representative examples of three different experiments from two different donors (Exp-1 and Exp-2, Exp-3 and Exp-4).

The present invention is explained hereinafter while disclosing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form unless specifically noted otherwise. Further, the terms used herein should be understood as used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The present invention provides an agent for delivery of an immunostimulatory oligonucleotide nucleic acid medicament, comprising a nucleic acid comprising a phosphorothioated nucleotide, an agent for immunostimulation comprising a core moiety with biological activity of an immunostimulatory oligonucleotide, and an oligonucleotide comprising a core moiety with biological activity and a nucleic acid comprising a phosphorothioated nucleotide. In summary, a nucleic acid enhances the function as an agent for delivery by preventing the formation of a multimer due to guanine in the present invention. It has been further discovered that substances known as an immunostimulatory oligonucleotide have a core moiety (Core) that is important for the exertion of activity, and an agent for immunostimulation comprising the same can be manufactured. Thus, such an agent for immunostimulation is provided herein. The present invention also provides an oligonucleotide combining such an agent for immunostimulation comprising a core sequence and the agent for delivery of the invention.

The definition of the terms and/or general techniques particularly used herein is explained hereinafter as appropriate.

As used herein, "immunostimulatory oligonucleotide" refers to oligonucleotides with immunostimulatory capability. Typical examples of immunostimulatory oligonucleotides include CpG oligonucleotides. As used herein, "CpG oligonucleotide (residue)" is interchangeably used with "CpG oligodeoxynucleotide (residue)", "CpG ODN (residue)", and simply "CpG (residue)" and refers to a polynucleotide, preferably an oligonucleotide, comprising at least one non-methylated CG dinucleotide sequence. The terms are synonymous regardless of the presence/absence of the term "residue" at the end. An oligonucleotide comprising at least one CpG motif can comprise multiple CpG motifs. As used herein, the term "CpG motif" refers to a non-methylated dinucleotide moiety of an oligonucleotide, comprising a cytosine nucleotide and the subsequent guanosine nucleotide. 5-methylcytosine may also be used instead of cytosine. Furthermore, polydeoxyadenylic acid is synonymous with polydeoxyadenosinic acid (residue). While the term "residue" refers to a partial structure of a compound with a larger molecular weight, as used herein, those skilled in the art can readily understand from the context as to whether "CpG oligodeoxynucleotide (CpG ODN)" refers to an independent molecule or a partial structure of a compound with a larger molecular weight. The same applies to terms related to other partial structures included by the oligodeoxynucleotide of the invention such as "polydeoxyadenylic acid".

CpG oligonucleotides (CpG ODN) are short (about 20 base pairs) single-stranded synthetic DNA fragments comprising an immunostimulatory CpG motif. A CpG oligonucleotide is a potent agonist of Toll-like receptor 9 (TLR9), which activates dendritic cells (DCs) and B cells to produce type I interferons (IFNs) and inflammatory cytokines (Hemmi, H., et al. Nature 408, 740-745 (2000); Krieg, A. M. Nature reviews. Drug discovery 5, 471-484 (2006).), and acts as an adjuvant of Th1 humoral and cellular immune responses including cytotoxic T lymphocyte (CTL) react ions (Brazolot Millan, C. L., Weeratna, R., Krieg, A. M., Siegrist, C. A. & Davis, H. L. Proceedings of the National Academy of Sciences of the United States of America 95, 15553-15558 (1998); Chu, R. S., Targoni, O. S., Krieg, A. M., Lehmann, P. V. & Harding, C. V. The Journal of experimental medicine 186, 1623-1631 (1997)). In this regard, CpG ODNs were considered to be a potential immunotherapeutic agent against infections, cancer, asthma, and hay fever (Krieg, A. M. Nature reviews. Drug discovery 5, 471-484 (2006); Klinman, D. M. Nature reviews. Immunology 4, 249-258 (2004)).

A CpG oligodeoxynucleotide (CpG ODN) is a single stranded DNA comprising an immunostimulatory non-methylated CpG motif, and is an agonist of TLR9. There are four types of CpG ODNs, i.e., K type (also called B type), D type (also called A type), C type, and P type, each with different backbone sequences and immunostimulatory properties (Advanced drug delivery reviews 61, 195-204 (2009)). In a preferred embodiment, the oligodeoxynucleotide of the invention includes D type (also called A type, thus also called A/D type) CpG ODNs thereamong.

Immunostimulatory CpG oligonucleotides (ODN) have been developed and utilized as Toll-like receptor (TLR) 9 dependent innate immune activators and vaccine adjuvants for more than 10 years. Four different types of immunostimulatory CpG ODNs (A/D, B/K, C, and P type) have been reported. A/D type ODNs are characterized by high interferon (IFN)-α production from plasmacytoid dendritic cells (pDC). B/K type ODNs mainly induce an inflammatory cytokine such as interleukin (IL)-6 or IL-12, but have low IFN-α production. B/K type ODNs are readily formulated with saline, some of which are in clinical trials. In contrast, A/D type ODNs endogenously form aggregates that are closely related to a high IFN-α profile, thus obstructing the preparation or clinical application of a product meeting the Good Manufacturing Practice (GMP). In the present application, the inventors have developed several D35 derived ODNs (generally used as A/D type ODN) which are modified by the addition of a phosphorothioate polynucleotide tail (e.g., dAs40) to examine their physical properties, solubility in saline, immunostimulatory activity on human peripheral blood mononuclear cells (PBMC), and potential as a vaccine adjuvant in monkeys. The inventors also examined the complex formation thereof with schizophyllan. The inventors have discovered that two modified ODNs including D35-dAs40 and D35core-dAs40 are similarly immunostimulatory as the original D35 in human PBMCs and induce high IFN-α secretion in a dose-dependent manner. Furthermore, analysis of physical properties using dynamic light scattering revealed that both D35-dAs40 and D35core-dAs40 do not form aggregates in saline. Such a property is currently not exhibited by the original D35.

Typically, K type CpG ODNs have structural and functional properties characterized by containing multiple CpG motifs with a non-palindromic structure and by producing IL-6 by activating B cells, but hardly inducing IFN-α production of plasmacytoid dendritic cells (pDCs). A non-methylated CpG motif refers to a short nucleotide sequence comprising at least one cytosine (C)-guanine (G) sequence whose cytosine is not methylated at position 5. In the following explanation, CpG refers to non-methylated CpG, unless specifically noted otherwise. Thus, inclusion of a K type CpG ODN results in immunostimulatory activity unique to K type CpG ODNs (e.g., activity to activate B cells (preferably human B cells) to induce IL-6 production). Many humanized K type CpG ODNs are known in the art (Journal of immunology 166, 2372-2377 (2001); Journal of immunology 164, 944-953 (2000); U.S. Pat. No. 8,030,285 B2).

D/A type is suggested as mainly inducing the production of type I interferon from plasmacytoid dendritic cells (also called "plasmacytoid DC" or "pDC"), and K/B type is suggested as inducing the growth of B cells and the production of IgM, IL-6, or the like. D/A type CpG-DNA strongly induces IFN-α production, but has low activity for inducing pDC maturation and exerts no direct immunostimulatory activity on B cells. K/B type exerts immunostimulatory activity on B cells, strongly promotes pDC maturation, and has high IL-12 induction capability, while having low IFN-α inducing capability. A C type sequence with TCG repeat sequences that are all thiolated induces IFN-α production by pDCs and polyclonal B cell activation.

D/A type CpG ODNs (also called A type, D type, or the like and denoted as CpG-A ODN) are oligonucleotides characterized by a poly-G motif with a centrally-located palindromic (palindromic structure) CpG-containing sequence of phosphodiester (PO) and a phosphorothioate (PS) bond at the 5' and 3' ends. Cell uptake is facilitated due to the presence of phosphorothioate (PS) at the 5' and 3' ends. D/A type CpG produces a large quantity of interferon-α (IFN-α) in pDCs (different feature from K/B type CpG). A potent activation and interferon gamma production are induced thereby in NK cells and γδ T cells. However, B cells are not activated and pDCs are not matured (Krug, A., et al. European journal of immunology 31, 2154-2163

(2001); and Verthelyi, D., Ishii, K. J., Gursel, M., Takeshita, F. & Klinman, D. M. Journal of immunology 166, 2372-2377 (2001)).

The other three types of ODNs consist of a PS backbone.

K/B type CpG ODNs are also called CpG-type B or CpG-type K. All K/B type CpG ODNs with one or more CpG motifs without a poly-G motif have a phosphorothioate (PS) backbone. Typically, a K/B type CpG ODN contains multiple CpG motifs with a non-palindromic structure. K/B type CpG has weak IFN-α inducing activity (produces nearly none), but is a very potent Th1 adjuvant and a potent B cell response stimulating agent that induces IL-6 production and pDC maturation by activating pDSs (Verthelyi, D., Ishii, K. J., Gursel, M., Takeshita, F. & Klinman, D. M. Journal of immunology 166, 2372-2377 (2001); and Hartmann, G. & Krieg, A. M. Journal of immunology 164, 944-953 (2000)). K/B type CpG ODNs have a function of promoting the survival, activating, and maturing both monocyte derived dendritic cells and pDCs.

Recently developed C and P type CpG ODNs comprise one and two palindromic structure CpG sequences, respectively. Both can activate B cells, like K type CpG ODNs, and activate pDCs, like D type CpG ODNs. Meanwhile, C type CpG ODNs more weakly induce IFN-α production relative to P type CpG ODNs (Hartmann, G., et al. European journal of immunology 33, 1633-1641 (2003); Marshall, J. D., et al. Journal of leukocyte biology 73, 781-792 (2003); and Samulowitz, U., et al. Oligonucleotides 20, 93-101 (2010)).

D/K type and P type CpG ODNs are shown to form a high-order structure i.e., Hoogsteen base pair forming a four parallel strand structure called G-tetrads and Watson-Crick base pair between a cis palindromic structure site and a trans palindromic structure site, respectively, which are required for potent IFN-α production by pDCs (Samulowitz, U., et al. Oligonucleotides 20, 93-101 (2010); Kerkmann, M., et al. The Journal of biological chemistry 280, 8086-8093 (2005); and Klein, D. C., Latz, E., Espevik, T. & Stokke, B. T. Ultramicroscopy 110, 689-693 (2010)). Due to the high-order structure, only K and C type CpG ODNs are generally considered usable as immunotherapeutic agents and vaccine adjuvants for humans (Puig, M., et al. Nucleic acids research 34, 6488-6495 (2006); Bode, C., Zhao, G., Steinhagen, F., Kinjo, T. & Klinman, D. M. Expert review of vaccines 10, 499-511 (2011); and McHutchison, J. G., et al. Hepatology 46, 1341-1349 (2007)).

In contrast to A type CpG ODNs, C type CpG has a complete phosphorothioate (PS) backbone without a poly-G motif, but comprises the CpG A type palindromic sequence in combination with a stimulatory CpG motif. It is reported from an in vivo study that a C type CpG ODN is a very potent Th1 adjuvant.

The D35 oligonucleotide used herein comprises TGCATCGATGCA (SEQ ID NO: 22) at the core moiety.

Examples of other oligonucleotides used herein include oligonucleotides with a core moiety (GACGATCGTC (SEQ ID NO: 56)) of A2216, oligonucleotides with a core moiety (ACGACGTCGT (SEQ ID NO: 58)) of A2336, oligonucleotides with the full length of B2006 (SEQ ID NO: 60), oligonucleotides with the full length (SEQ ID NO: 62) of C2395; and oligonucleotides with the full length (SEQ ID NO: 64) of P21889.

A CpG ODN and a nucleic acid used as an agent for delivery may be linked directly by a covalent bond or via a spacer sequence. A spacer sequence refers to a nucleotide sequence comprising one or more nucleotides inserted between two adjacent constituent elements. The length of a spacer sequence is not particularly limited in the present invention, as long as it has immunostimulatory activity (preferably activity to activate B cells to induce IL-6 production and/or activity to activate dendritic cells to induce IFN-α production), but the length is generally 1-10 nucleotides long, preferably 1-5 nucleotides long, and 1-3 nucleotides long in certain embodiments. Examples of spacers include C3, C6, C12, S9, S18, dSpacer, and the like, which can be incorporated by nucleic acid synthesis. In this regard, C indicates any carbon chain, S indicates an ethylene glycol chain, dSpacer indicates a backbone with only ribose without bases, and each number indicates the degree of polymerization of hydrocarbon or ethylene glycol. In yet another embodiment, examples include at least one or more nucleotides, ethylene glycols, or hydrocarbons. In another embodiment, a CpG ODN and an agent for delivery are directly linked by a covalent bond.

As used herein, "subject" refers to a target subjected to the diagnosis, detection, therapy, or the like of the present invention (e.g., organisms such as humans, or cells, blood, serum, or the like extracted from an organism).

As used herein, "agent" broadly may be any substance or another element (e.g., light, radiation, heat, electricity, and other forms of energy) as long as the intended objective can be achieved. Examples of such substances include, but are not limited to, proteins, polypeptides, oligopeptides, peptides, polynucleotides, oligonucleotides, nucleotides, nucleic acids (including for example DNAs such as cDNAs and genomic DNAs, and RNAs such as mRNAs), polysaccharides, oligosaccharides, lipids, organic small molecules (e.g., hormones, ligands, information transmitting substances, organic small molecules, molecules synthesized by combinatorial chemistry, small molecules that can be used as a medicament (e.g., small molecule ligands and the like) and composite molecules thereof.

As used herein, "therapy" refers to the prevention of exacerbation, preferably maintaining the current condition, more preferably alleviation, and still more preferably elimination of a disease or disorder (e.g., cancer or allergy) in case of such a condition, including being capable of exerting a prophylactic effect or an effect of improving a patient's diseaseor one or more symptoms accompanying the disease. Preliminary diagnosis conducted for suitable therapy may be referred to as a "companion therapy", and a diagnostic agent therefor may be referred to as "companion diagnostic agent".

As used herein, "therapeutic agent" broadly refers to all agents that are capable of treating the condition of interest (e.g., diseases such as cancer or allergies). In one embodiment of the present invention, "therapeutic agent" may be a pharmaceutical composition comprising an effective ingredient and one or more pharmacologically acceptable carriers. A pharmaceutical composition can be manufactured, for example, by mixing an effective ingredient and the above-described carriers by any method that is known in the technical field of pharmaceuticals. Further, usage form of a therapeutic agent is not limited, as long as it is used for therapy. A therapeutic agent may consist solely of an effective ingredient or may be a mixture of an effective ingredient and any ingredient. Further, the shape of the above-described carriers is not particularly limited. For example, the carrier may be a solid or liquid (e.g., buffer). Therapeutic agents for cancer, allergies, or the like include drugs (prophylactic agents) used for the prevention of cancer, allergies, or the like, and suppressants of cancer, allergies, or the like.

As used herein, "prevention" refers to the act of taking a measure against a disease or disorder (e.g., diseases such as cancer or allergy) from being in a condition, prior to the onset of such a condition. For example, it is possible to use the agent of the invention to perform diagnosis, and use the agent of the invention, as needed, to prevent or take measures to prevent allergies or the like.

As used herein, "prophylactic agent" broadly refers to all agents that are capable of preventing the condition of interest (e.g., disease such as cancer or allergies).

As used herein, "kit" refers to a unit providing portions to be provided (e.g., testing agent, diagnostic agent, therapeutic agent, antibody, label, manual, and the like), generally in two or more separate sections. This form of a kit is preferred when intending to provide a composition that should not be provided in a mixed state is preferably mixed immediately before use for safety reasons or the like. Such a kit advantageously comprises instructions or a manual preferably describing how the provided portions (e.g., testing agent, diagnostic agent, or therapeutic agent) should be used or how a reagent should be handled. When the kit is used herein as a reagent kit, the kit generally comprises an instruction describing how to use a testing agent, diagnostic agent, therapeutic agent, antibody, and the like.

As used herein, "instruction" is a document with an explanation of the method of use of the present invention for a physician or for other users. The instruction describes a detection method of the present invention, how to use a diagnostic agent, or a description instructing administration of a medicament or the like. Further, an instruction may have a description instructing oral administration, or administration to the esophagus (e.g., by injection or the like) as the site of administration. The instruction is prepared in accordance with a format defined by a regulatory authority of the country in which the present invention is practiced (e.g., Ministry of Health, Labour and Welfare in Japan, Food and Drug Administration (FDA) in the U.S., or the like), with an explicit description showing approval by the regulatory authority. The instruction is a so-called "package insert", and is generally provided in, but not limited to, paper media. The instructions may also be provided in a form such as electronic media (e.g., web sites provided on the Internet or emails).

(Medicament, Dosage Form, etc.)

The present invention is provided as a medicament (therapeutic agent or prophylactic agent) in various forms described above.

The route of administration of a therapeutic agent that is effective upon therapy is preferably used, such as intravenous, subcutaneous, intramuscular, intraperitoneal, oral administration, or the like. Examples of dosage forms include injection, capsules, tablets, granules, and the like. The components of the present invention are effectively used upon administration as an injection. Aqueous solutions for injection may be stored, for example, in a vial or a stainless steel container. Aqueous solutions for injections may also be blended with, for example, saline, sugar (e.g., trehalose), NaCl, NaOH, or the like. Therapeutic agents may also be blended, for example, with a buffer (e.g., phosphate buffer), stabilizer, or the like.

In general, the composition, medicament, therapeutic agent, prophylactic agent, or the like of the present invention comprises a therapeutically effective amount of a therapeutic agent or effective ingredient, and a pharmaceutically acceptable carrier or excipient. As used herein, "pharmaceutically acceptable" means that a substance is approved by a government regulatory agency or listed in the pharmacopoeia or other commonly recognized pharmacopoeia for use in animals, more specifically in humans. As used herein "carrier" refers to a diluent, adjuvant, excipient or vehicle that is administered with a therapeutic agent. Such a carrier can be an aseptic liquid such as water or oil, including, but not limited to, those derived from petroleum, animal, plant, or synthesis, as well as peanut oil, soybean oil, mineral oil, sesame oil, and the like. When a medicament is orally administered, water is a preferred carrier. For intravenous administration of a pharmaceutical composition, saline and aqueous dextrose are preferred carriers. Preferably, an aqueous saline solution and aqueous dextrose and glycerol solution are used as a liquid carrier of an injectable solution. Suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, medium-chain fatty acid triglyceride, polyoxyethylene hydrogenated castor oil 60, saccharose, carboxymethylcellulose, corn starch, inorganic salt, and the like. When desirable, the composition can also contain a small amount of wetting agent, emulsifier, or pH buffer. These compositions can be in a form of a solution, suspension, emulsion, tablet, pill, capsule, powder, sustained release preparation, or the like. It is also possible to use traditional binding agents and carriers, such as triglyceride, to prepare a composition as a suppository. Oral preparation can also comprise a standard carrier such as medicine grade mannitol, lactose, starch, magnesium stearate, sodium saccharin, cellulose, or magnesium carbonate. Examples of a suitable carrier are described in E. W. Martin, Remington's Pharmaceutical Sciences (Mark Publishing Company, Easton, U.S.A.). Such a composition contains a therapeutically effective amount of therapy agent, preferably in a purified form, together with a suitable amount of carrier, such that the composition is provided in a form that is suitable for administration to a patient. A preparation must be suitable for the administration form. In addition, the composition may comprise, for example, a surfactant, excipient, coloring agent, flavoring agent, preservative, stabilizer, buffer, suspension, isotonizing agent, binding agent, disintegrant, lubricant, fluidity improving agent, corrigent, or the like.

Examples of "salt", in one embodiment of the present invention, include anionic salts formed with any acidic (e.g., carboxyl) group and cationic salts formed with any basic (e.g., amino) group. Salts include inorganic salts and organic salts, as well as salts described in, for example, Berge et al., J. Pharm. Sci., 1977, 66, 1-19. Examples thereof further include metal salts, ammonium salts, salts with organic base, salts with inorganic acid, salts with organic acid, and the like. "Solvate" in one embodiment of the present invention is a compound formed with a solute or solvent. For example, J. Honig et al., The Van Nostrand Chemist's Dictionary P650 (1953) can be referred to for solvates. When the solvent is water, a solvate formed thereof is a hydrate. It is preferable that the solvent does not obstruct the biological activity of the solute. Examples of such a preferred solvent include, but not particularly limited to, water and various buffers. Examples of "chemical modification" in one embodiment of the present invention include modifications with PEG or a derivative thereof, fluorescein modification, biotin modification, and the like.

When the present invention is administered as a medicament, various delivery systems are known, which can be used to administer the therapeutic agent of the invention to a suitable site (e.g., esophagus). Examples of such a system include use of a recombinant cell that can express encapsulated therapeutic agent (e.g., polypeptide) in liposomes, microparticles, and microcapsules; use of endocytosis mediated by a receptor; construction of a therapy nucleic acid as a part of a retrovirus vector or another vector; and the like. Examples of the method of introduction include, but are not limited to, intradermal, intramuscular, intraperitoneal, intravenous, subcutaneous, intranasal, epidural, and oral routes. A medicament can be administered by any suitable route, such as by injection, by bolus injection, or by absorption through epithelia or mucocutaneous lining (e.g., oral cavity, rectum, intestinal mucosa, or the like). In addition, an inhaler or mistifier using an aerosolizing agent can be used as needed. Moreover, other biological activating agents can also be administered concomitantly. Administration can be systemic or local. When the present invention is used for cancer, the present invention can be administered by any suitable route such as a direct injection into cancer (lesion).

In a preferred embodiment, a composition can be prepared as a pharmaceutical composition adapted to administration to humans in accordance with a known method. Such a composition can be administered by an injection. A composition for injection is typically a solution in an aseptic isotonic aqueous buffer. A composition can also comprise a local anesthetic such as lidocaine, which alleviates the pain at the site of injection, and a solubilizing agent as needed. Generally, ingredients can be supplied individually or by mixing the ingredients together in a unit dosage form; and supplied, for example, in a sealed container such as an ampoule or sachet showing the amount of active agent, or as a lyophilized powder or water-free concentrate. When a composition is to be administered by injection, the composition can be distributed using an injection bottle containing aseptic agent-grade water or saline. When a composition is to be administered by injection, an aseptic water or saline ampoule for injection can also be provided such that the ingredients can be mixed prior to administration.

The composition, medicament, therapeutic agent, and prophylactic agent of the invention can be prepared with a neutral or base form or other prodrugs (e.g., ester or the like). Pharmaceutically acceptable salts include salts formed with a free carboxyl group, derived from hydrochloric acid, phosphoric acid, acetic acid, oxalic acid, tartaric acid, or the like, salts formed with a free amine group, derived from isopropylamine, triethylamine, 2-ethylaminoethanol, histidine, procaine, or the like; and salts derived from sodium, potassium, ammonium, calcium, ferric hydroxide or the like.

The amount of therapeutic agent of the invention that is effective in therapy of a specific disorder or condition may vary depending on the properties of the disorder or condition. However, such an amount can be determined by those skilled in the art with a standard clinical technique based on the descriptions herein. Furthermore, an in vitro assay can be used in some cases to assist the identification of the optimal dosing range. The precise dose to be used for a preparation may also vary depending on the route of administration or the severity of the disease or disorder. Thus, the dose should be determined in accordance with the judgment of the attending physician or the condition of each patient. The dosage is not particularly limited, but may be, for example, 0.001, 1, 5, 10, 15, 100, or 1000 mg/kg body weight per dose or within a range between any two values described above. The dosing interval is not particularly limited, but may be, for example, 1 or 2 doses every 1, 7, 14, 21, or 28 days, or 1 or 2 doses in a range of period between any two values described above. The dosage, dosing interval, and dosing method may be appropriately selected depending on the age, weight, symptom, target organ, or the like of the patient. Further, it is preferable that a therapeutic agent contains a therapeutically effective amount of effective ingredients, or an amount of effective ingredients effective for exerting a desired effect. When a malignant tumor marker significantly decreases after administration, presence of a therapeutic effect may be acknowledged. The effective dose can be estimated from a dose-response curve obtained from in vitro or animal model testing systems.

"Patient" or "subject" in one embodiment of the present invention includes humans and mammals excluding humans (e.g., one or more of mice, guinea pigs, hamsters, rats, rabbits, pigs, sheep, goats, cows, horses, cats, dogs, marmosets, monkeys, and the like).

The pharmaceutical composition, therapeutic agent, or prophylactic agent of the invention can be provided as a kit.

In a specific embodiment, the present invention provides an agent pack or kit comprising one or more containers filled with one or more ingredients of the composition or medicament of the invention. Optionally, information indicating approval for manufacture, use, or sale for administration to a human by a government agency regulating the manufacture, use, or sale of medicaments or biological products can be appended to such a container in a stipulated form.

In a specific embodiment, the pharmaceutical composition comprising an ingredient of the present invention can be administered via liposomes, microparticles, or microcapsules. In various embodiments of the present invention, it may be useful to use such a composition to achieve sustained release of the ingredient of the present invention.

The formulation procedure for the therapeutic agent, prophylactic agent, or the like of the invention as a medicament or the like is known in the art. The procedure is described, for example, in the Japanese Pharmacopoeia, the United States Pharmacopeia, pharmacopeia of other countries, or the like. Thus, those skilled in the art can determine the embodiment such as the amount to be used without undue experimentation from the descriptions herein.

Preferred Embodiments

The preferred embodiments of the present invention are explained hereinafter. It is understood that the embodiments provided hereinafter are provided to better facilitate the understanding of the present invention, so that the scope of the present invention should not be limited by the following description. Thus, it is apparent that those skilled in the art can refer to the descriptions herein to appropriately make modifications within the scope of the present invention. It is also understood that the following embodiments of the present invention can be used individually or as a combination.

<Agent for Delivery (Deliver Agent) of Immunostimulatory Oligonucleotide Nucleic Acid Medicine>

The present invention provides an agent for delivery of an immunostimulatory oligonucleotide nucleic acid medicine, comprising a nucleic acid comprising a phosphorothioated nucleotide (herein, also called a "agent for delivery of the invention", including each of the embodiments thereof). Thus, the present invention also provides a method of delivering an immunostimulatory oligonucleotide nucleic acid medicament, wherein the method comprises binding the immunostimulatory oligonucleotide nucleic acid medicament with a nucleic acid comprising a phosphorothioated nucleotide or an agent for delivery comprising a nucleic acid comprising a phosphorothioated nucleotide directly or, for example, via a spacer or the like, for administration to a subject. This aspect focuses only on the tail unit. Such a nucleic acid is also called a "tail nucleic acid" herein. In one embodiment, the nucleic acid prevents the formation of a multimer due to guanine. However, it would be impossible to introduce the typical CpG, D35, into cells with a nucleic acid alone when guanine is changed to another base (A, T, C, or the like), i.e., when G is changed to A, T. or C. Thus, D35 was demonstrated to have limited utility as a medicament. In this regard, the core sequence, when extracted, was shown to have IFN-α production inducing activity only by the core sequence. Thus, this would be a useful medicament if this can be efficiently introduced into cells. While conventional techniques utilized liposome formation, this was a complex technique. Thus, development of a simple technique has been in demand. Further, a phenomenon was observed where delivery could not be successfully executed when using a core sequence. In view of the above, delivery had a problem of not being sufficiently carried out with only a core sequence so that drug efficacy could not be exerted. In this regard, the present invention provides a nucleic acid comprising a phosphorothioated nucleotide to provide a tail unit that prevents the phenomenon of preventing delivery and exhibits self-introducing capability, enabling delivery or introduction into cells such that a CpG ODN unit that provides effective IFN-α activity can be provided. In this regard, it was found that phosphorothioation of a tail moiety is advantageous for introduction into cells with a single agent and for attaining INF-α producing capability. In this manner, the concept of separating a A/D type nucleic acid adjuvant into two units for activity and cell introduction had not been known up to this point. The concept is recognized as one of the features of the present invention. The prevent invention also conducts a structure activity correlation test. Thus, it is understood which parameter affects which activity, such that optimization is possible.

The present invention provides an IFN-α production inducing nucleic acid adjuvant that is bound to a straight chain nucleic acid. It was found that a certain length, regardless of the type, is advantageous for a tail nucleic acid to prevent a phenomenon of preventing delivery or gelation. Thus, the nucleic acid of the present invention reduces or eliminates the phenomenon of preventing delivery or gelation. Hence, although not wishing to be bound by any theory, the nucleic acid of the invention imparts an injectable property because it does not form a gel in a salt solution. Thus, although not wishing to be bound by any theory, the nucleic acid can be used as a novel adjuvant or enhancer of an infection vaccine. The nucleic acid can also be used as a replacement or an enhancer of IFN-α supplementing therapy. Since it may be possible to provide the nucleic acid as an immunomodulator or an enhancer as a single agent, the nucleic acid can also be applied as a therapeutic agent such as Leishmania.

One of the requirements for materializing or enhancing such delivery includes materialization of prevention of high order aggregate formation due to guanine. Although not wishing to be bound by any theory, delivery is facilitated by the agent for delivery of the invention by preventing high order aggregate formation, e.g., not inhibiting multimer formation but inhibiting high order aggregate formation due to random occurrence thereof.

Examples of agents for materializing or enhancing delivery in the present invention include phosphorothioated nucleotide content. In a preferred embodiment, the phosphorothioated nucleotide content in the nucleic acid in the agent for delivery of the invention can be advantageously about 25% or greater or greater than about 25%, preferably about 35% or greater or greater than about 35%, and more preferably about 50% or greater or greater than about 50%. The location where a phosphorothioated nucleotide is contained is also considered in addition to content. Although not wishing to be bound by any theory, it may be advantageous to dispose phosphorothioated nucleotides on the terminal side. Although not wishing to be bound by any theory, it is understood that the content required may be lower when disposed on the terminal side. Since the effect on interferon-α and interleukin 6 slightly varies depending on each content, those skilled in the art can determine the optimal range thereof while considering the effect of interest.

In one embodiment, a phosphorothioate in a form of being bound to the 5' end may be preferred, but the present invention is not necessarily limited thereto. The number of phosphorothioates at the 5' end is not limited in such a form bound to the 5' end. For instance, it is demonstrated in the Examples that the number may be one or two.

In another embodiment, it may be advantageous that the nucleic acid has a certain length. Generally, a length of 5 bases or greater may be advantageous. Examples of the lower limit for the base length of the nucleic acid used in the present invention include lengths of about 5 base or greater, about 6 bases or greater, about 7 bases or greater, about 8 bases or greater, about 9 bases or greater, about 10 bases or greater, about 15 bases or greater, about 20 bases or greater, about 25 bases or greater, about 30 bases or greater, about 35 bases or greater, about 40 bases or greater, about 45 bases or greater, about 50 bases or greater, about 55 bases or greater, or about 60 bases or greater. Since activity is observed even with 100 bases, the upper limit of base length of the nucleic acids used in the present invention is not particularly limited. However, a slight decrease in activity is observed at about 100 bases. Thus, in a preferred embodiment, the length may be about 150 bases or less, about 140 bases or less, about 130 bases or less, about 120 bases or less, about 110 bases or less, about 100 bases or less, about 95 bases or less, about 90 bases or less, about 85 bases or less, or about 80 bases or less. Any of these upper and lower limits may be combined. Preferred examples thereof include, but are not limited to, lengths of about 5-100 bases, about 6-100 bases, about 7-100 bases, about 8-100 bases, about 9-100 bases, about 10-100 bases, about 20-80 bases, about 40-80 bases, about 20-60 bases, and the like.

As one requirement, it is preferable to materialize the prevention of high order aggregate formation due to guanine. Conditions for the materialization thereof include content, no or few consecutive guanines, and the like. For example, the guanine content of the nucleic acid in one embodiment in the agent for delivery of the invention may be less than 60%, but it is preferably, but is not limited to, 60% or greater, 70% or greater, or 80% or greater. In another embodiment, the nucleic acid of the invention does not have a portion with three or more consecutive guanines. These features may be combined. Since the effect of these features on interferon-α and interleukin 6 may slightly vary depending on each form, those skilled in the art can determine the optimal range of these features while considering the effect of interest.

In one embodiment, the agent for delivery of the invention is bound to a moiety with biological activity. The agent for delivery can be used as a single agent by being bound.

The moiety with biological activity may be any moiety with biological activity such as activity as a medicament. Typically, this may be a moiety comprising a nucleic acid such as an oligonucleotide. This is because the agent for delivery of the invention is constituted based on a nucleic acid, so that this is consistent (has integrity) with being provided as a single agent.

In one representative embodiment, the moiety with biological activity bound to the agent for delivery of the invention has a full length or a core moiety with biological activity of an A/D type immunostimulatory oligonucleotide or the full length of a B/K type, C type, or D type immunostimulatory oligonucleotide.

In one specific embodiment, the moiety with biological activity bound to the agent for delivery of the invention has a core moiety with biological activity of an A/D type immunostimulatory oligonucleotide. Although not wishing to be bound by any theory, an A/D type immunostimulatory oligonucleotide is a type of CpG that tends to aggregate and is considered to improve its drug efficacy by aggregation. Thus, efforts were not particularly made to prevent aggregation. Thus, the ingenuity of the present invention should be assessed as an effort in the opposite direction.

In another specific embodiment, the moieties with biological activity that can be used in the present invention include, but are not limited to, a core moiety (TGCATCGATGCA (SEQ ID NO: 22)) of a D35 oligonucleotide, a core moiety (GACGATCGTC (SEQ ID NO: 56)) of A2216, a full length moiety (ggggGACGA: TCGTCgggggg (SEQ ID NO: 65); capital letters indicate the core moiety) of A2216, a core moiety (ACGACGTCGT (SEQ ID NO: 58)) of A2336, a full length moiety (ggggACGAC: GTCGTggggggg (SEQ ID NO: 66); capital letters indicate the core moiety) of A2336, a full length (TCGTCGTTTTGTCGTTTTGTCGTT (SEQ XD NO: 60)) of B2006, a full length (TCGTCGTTTTCGGCGCGCGCCG (SEQ ID NO: 62)) of C2395, a full length (TCGTCGACGATCGGCGCGCGCCG (SEQ ID NO: 64)) of P21889, CPG 7909: TsCsGsTsCsGsTsTsTsTsGsTsCsGsTsTsTsTsGsTsCsGsTsT (SEQ ID NO: 67; B/K type), PF-3512676: TsCsGsTsCsGsTsTsTsTsGsTsCsGsTsTsTsTsGsTsCsGsTsT (SEQ ID NO: 68; B/K type), CYT003-QBG10: GGGGGGGGGGGACGATCGTCGGGGGGGGGG (SEQ ID NO: 69; A/D type), 1018 ISS: TsGsAsCsTsGsTsGsAsAsCsGsTsTsCsGsAsGsAsTsGsA (SEQ ID NO: 70; B/K type), and Kappaproct (DIMS 0150): GsGsAsACAGTTCGTCCATsGsGsC (SEQ ID NO: 71; A/D type) (s indicates a phosphorothioate bond).

In another embodiment, the oligonucleotide of the invention may be present in a solution comprising sodium salt (e.g., saline, phosphate buffered saline (PBS), or the like). Although not wishing to be bound by any theory, this is because the phenomenon of not being deliverable observed for A/D type core sequences is particularly observed prominently when dissolved in an aqueous solution of sodium salt, while the problem with saline or the like that is commonly used can be solved by such an oligonucleotide.

<"Biological Activator" Focused on Core Sequence>

In one embodiment, the present invention provides an agent for immunostimulation comprising a core moiety with biological activity of an A/D type, B/K type, C type, or P type immunostimulatory oligonucleotide (herein, also referred to as the "agent for immunostimulation of the invention", including each of the embodiments thereof). Although not wishing to be bound by any theory, the core moiety itself was found to have immunostimulatory capability and IFN-α production inducing activity and/or interleukin 6 production inducing activity. Thus, the present invention can provide an agent for immunostimulation with a wide range of designs. Hence, the present invention also provides a method of stimulating immunity of a subject, the method comprising administering to the subject an effective amount of the agent for immunostimulation comprising a core moiety with biological activity of a A/D type, B/K type, C type, or D type immunostimulatory oligonucleotide.

As used herein, "core moiety" refers to a sequence that is 6 bp or greater with a palindrome configuration comprising a CpG sequence.

In one embodiment, the immunostimulatory oligonucleotide used in the agent for immunostimulation of the invention is of A/D type, and the biological activity is interferon (IFN)-α production inducing activity and/or interleukine-6 production inducing activity.

In a more preferred embodiment, the core moiety of the immunostimulatory oligonucleotide used in the agent for immunostimulation of the invention is a moiety of A/D type from which consecutive Gs are removed, preferably all Gs at the ends may be removed or one G may remain.

In yet another embodiment, the core moiety of the immunostimulatory oligonucleotide used in the agent for immunostimulation of the invention comprises a core moiety (TGCATCGATGCA (SEQ ID NO: 22)) of a D35 oligonucleotide, a core moiety (GACGATCGTC (SEQ ID NO: 56)) of A2216, a core moiety (ACGACGTCGT (SEQ ID NO: 58)) of A2336, or the like.

In one embodiment, the core moiety used in the present invention is comprised by a vehicle for cell introduction. Any vehicle may be used as the vehicle for cell introduction, but the vehicle may be, for example, a liposome or the agent for delivery of the invention.

<"Improved Nucleic Acid Medicine" Focused on the Entire Immunostimulatory Oligonucleotide>

In another aspect, the present invention provides an oligonucleotide comprising a full length or a core moiety with biological activity of an immunostimulatory oligonucleotide and a nucleic acid comprising a phosphorothioated nucleotide (herein, also referred to as the "oligonucleotide of the invention").

It is understood that the nucleic acid comprising a phosphorothioated nucleotide used in this aspect can be used in any embodiment explained in <Agent for delivery (delivery agent) of immunostimulatory oligonucleotide nucleic acid medicine>.

In one embodiment, the oligonucleotide of the invention prevents the formation of a high order aggregate due to guanine.

In a preferred embodiment, examples of factors for materializing or enhancing delivery of the oligonucleotide of the invention include phosphorothioated nucleotide content. In a preferred embodiment, the phosphorothioated nucleotide content in the nucleic acid in the agent for delivery of the invention is advantageously about 25% or greater or greater than about 25%, preferably about 35% or greater or greater than about 35%, and more preferably about 50% or greater or greater than about 50%. The location where a phosphorothioated nucleotide is contained is also considered in addition to content. Although not wishing to be bound by any theory, it may be advantageous to dispose phosphorothioated nucleotides on the terminal side. Although not wishing to be bound by any theory, it is understood that the content required may be lower when disposed on the terminal side. Since the effect on interferon-α and interleukin-6 slightly varies depending on each content, those skilled in the art can determined the optimal range thereof while considering the effect of interest.

In another embodiment, it may be advantageous that the nucleic acid has a certain length in the oligonucleotide of the invention. Generally, a length of 5 bases or more may be advantageous. Examples of the lower limit for the base length of nucleic acid used in the present invention include lengths of about 5 base or greater, about 6 bases or greater, about 7 bases or greater, about 8 bases or greater, about 9 bases or greater, about 10 bases or greater, about 15 bases or greater, about 20 bases or greater, about 25 bases or greater, about 30 bases or greater, about 35 bases or greater, about 40 bases or greater, about 45 bases or greater, about 50 bases or greater, about 55 bases or greater, or about 60 bases or greater. Since activity is observed even with 100 bases, the upper limit of base length of the nucleic acids used in the present invention is not particularly limited. However, a slight decrease in activity is observed at about 100 bases. Thus, in a preferred embodiment, the length may be about 150 bases or less, about 140 bases or less, about 130 bases or less, about 120 bases or less, about 110 bases or less, about 100 bases or less, about 95 bases or less, about 90 bases or less, about 85 bases or less, or about 80 bases or less. Any of these upper and lower limits may be combined. Preferred examples thereof include, but are not limited to, lengths of about 5-100 bases, about 6-100 bases, about 7-100 bases, about 8-100 bases, about 9-100 bases, about 10-100 bases, about 20-80 bases, about 40-80 bases, about 20-60 bases, and the like. Since, the effect of interferon-α and interleukin-6 may slightly vary depending on each length, those skilled in the art can determine the optimal range while considering the effect of interest.

In yet another embodiment, it is preferable to materialize the prevention of high order aggregate formation due to guanine. Conditions for the materialization thereof include content, no or few consecutive guanines, and the like. For example, the guanine content of the nucleic acid in one embodiment in the agent for delivery of the invention may be less than 60%, but is preferably, but not limited to, 60% or greater, 70% or greater, or 80% or greater. In another embodiment, the nucleic acid of the invention does not have a portion with three or more consecutive guanines. These features may be combined. Since the effect of the features on interferon-α and interleukin-6 may slightly vary depending on each form, those skilled in the art can determine the optimal range while considering the effect of interest.

In another embodiment, the core moiety with biological activity in the oligonucleotide of the invention is from a A/D type, B/K type, or C type immunostimulatory oligonucleotide.

In another embodiment, the immunostimulatory oligonucleotide in the oligonucleotide of the invention is of A/D type, and the biological activity is interferon (IFN)-α inducing or enhancing activity and/or interleukine-6 inducing or enhancing activity.

In another embodiment, the core moiety in the oligonucleotide of the invention is the core moiety is a full length sequence of A/D type from which consecutive Gs are removed, preferably all Gs at the end are removed or one G may remain.

In another embodiment, the core moiety in the oligonucleotide of the invention can be selected from a core moiety (TGCATCGATGCA (SEQ ID NO: 22)) of a D35 oligonucleotide, a core moiety (GACGATCGTC (SEQ ID NO: 56)) of A2216, a full length moiety (ggggGACGA: TCGTCgggggg (SEQ ID NO: 65); capital letters indicate the core moiety) of A2216, a core moiety (ACGACGTCGT (SEQ ID NO: 58)) of A2336, a full length moiety (ggggACGAC: GTCGTgggggg (SEQ ID NO: 66) of A2336; capital letters indicate the core moiety) of A2336, a full length (TCGTCGTTTTGTCGTTTTGTCGTT (SEQ ID NO: 60)) of B2006, a full length TCGTCGTTTTCGGCGCGCGCCG (SEQ ID NO: 62)) of C2395, a full length (TCGTCGAC-GATCGGCGCGCGCCG (SEQ ID NO: 64)) of P21889, CPG 7909: TsCsGsTsCsGsTsTsTsTsGsTsCsGsTsTsTsT-sGsTsCsGsTsT (SEQ ID NO: 67), PF-3512676: TsCsGsT-sCsGsTsTsTsTsGsTsCsGsTsTsTsTsGsTsCsGsTsT (SEQ ID NO: 68), CYT003-QBG10: GGGGGGGGGGGAC-GATCGTCGGGGGGGGG (SEQ ID NO: 69), 1018 ISS: TsGsAsCsTsGsTsGsAsAsCsGsTsTsCsGsAsGsAsTsGsA (SEQ ID NO: 70), and Kappaproct (DIMS 0150): GsGsAsACAGTTCGTCCATsGsGsC (SEQ ID NO: 71) (s indicates a phosphorothioate bond).

In another aspect, the present invention provides an agent for immunostimulation comprising the oligonucleotide of the invention.

In one embodiment, the agent for immunostimulation is for inducing or enhancing interferon (IFN)-α production and/or inducing or enhancing interleukine-6 production.

(Use)

In another aspect, use of the oligonucleotide of the invention in the manufacture of an immunostimulatory oligonucleotide nucleic acid medicament is provided. It is understood that the oligonucleotide used in this aspect can be used in any form described herein.

(General Techniques)

Molecular biological approaches, biochemical approaches, and microbiological approaches used herein are well known and conventional approaches in the art that are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997, and the like. The relevant portions (which can be the entire document) of the above documents are incorporated herein by reference.

DNA synthesis techniques and nucleic acid chemistry for making an artificially synthesized gene are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, and the like, the relevant portions of which are incorporated herein by reference.

For example, as used herein, the oligonucleotide of the invention can also be synthesized by a standard method known in the art, such as using an automated DNA synthesizer (a synthesizer commercially available from Biosearch, Applied Biosystems, or the like). For example, a phosphorothioated oligonucleotide can also be synthesized by the method of Stein et al. (Stein et al., 1988, Nucl. Acids Res. 16: 3209), and a methyl phosphonate-oligonucleotide can also be prepared using a control pore glass polymer support (Sarin et al., 1988, Proc. Natl. Acad. Sci. USA 85: 7448-7451).

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

The Examples are described hereinafter. When necessary, animals used in the following Examples were handled in compliance with the institutional guidelines of the National Institute of Biomedical Innovation, based on the Declaration of Helsinki. For reagents, the specific products described in the Examples were used. However, the reagents can be substituted with an equivalent product from another manufacturer (Sigma-Aldrich, Wako Pure Chemical, Nacalai Tesque, R & D Systems, USCN Life Science INC, or the like).

Example 1

Experiments with D35

Hereinafter, this Example uses a typical agent for immunostimulation D35 (SEQ ID NO: 31) to demonstrate that a poly-dAs40 tailed A/D type ODN has an immunostimulatory potential that is similar to that of the original D35.

(Preparation of Human PBMCs)

PBMCs were prepared from healthy Japanese adult volunteers from whom informed consent was obtained. All experiments using human PBMCs were approved by the Institutional Review Board of the National Institute of Biomedical Innovation (Permit number: 44). After preparing PBMCs using Ficoll-Paque PLUS (GE Healthcare) and LeucoSep (Greiner), the PBMCs were plated, at a concentration of $2 \times 10^7$ cells/mL (96-well flat bottomed plate, total volume of 100 µL/well) in an RPMI 1640 medium supplemented with 10% fetal bovine serum, 100 units/mL of penicillin, and 100 µg/mL of streptomycin (all from Nacalai Tesque Inc. (Kyoto)).

(CpG ODN Simulation with or without N-[1-(2,3-dioleoyloxy)propyl)]-N,N,N-trimethylammonium Methyl Sulfate (DOTAP))

ODNs listed in the following Table 1 were synthesized by GeneDesign, Inc. (Osaka, Japan).

TABLE 1

Modified D35 ODNs developed in the present invention (SEQ ID NOs: 1-28)

| | | | | |
|---|---|---|---|---|
| D35(CG)G-dAs40* | GsGTGCATCGATGCAGGGGsGsGs-As40 | FIG. 1A | 1 | SEQ ID NO: 1 |
| D35(GC)G-dAs40 | GsGTGCATGCATGCAGGGGsGsGs-As40 | | 2 | SEQ ID NO: 2 |
| D35(TG)G-dAs40 | GsGTGCATTGATGCAGGGGsGsGs-As40 | | 3 | SEQ ID NO: 3 |
| D35(CT)G-dAs40 | GsGTGCATCTATGCAGGGGsGsGs-As40 | | 4 | SEQ ID NO: 4 |
| D35(CG)A-dAs40 | GsGTGCATCGATGCAAAAAsAsAs-As40 | | 5 | SEQ ID NO: 5 |
| D35(GC)A-dAs40 | GsGTGCATGCATGCAAAAAsAsAs-As40 | | 6 | SEQ ID NO: 6 |
| D35(TG)A-dAs40 | GsGTGCATTGATGCAAAAAsAsAs-As40 | | 7 | SEQ ID NO: 7 |
| D35(CT)A-dAs40 | GsGTGCATCTATGCAAAAAsAsAs-As40 | | 8 | SEQ ID NO: 8 |
| D35(CG)T-dAs40** | GsGTGCATCGATGCATTTTsTsTs-As40 | | 9 | SEQ ID NO: 9 |
| D35(GC)T-dAs40 | GsGTGCATGCATGCATTTTsTsTs-As40 | | 10 | SEQ ID NO: 10 |
| D35(TG)T-dAs40 | GsGTGCATTGATGCATTTTsTsTs-As40 | | 11 | SEQ ID NO: 11 |
| D35(CT)T-dAs40 | GsGTGCATCTATGCATTTTsTsTs-As40 | | 12 | SEQ ID NO: 12 |
| D35(CG)C-dAs40 | GsGTGCATCGATGCACCCCsCsCs-As40 | | 13 | SEQ ID NO: 13 |
| D35(GC)C-dAs40 | GsGTGCATGCATGCACCCCsCsCs-As40 | | 14 | SEQ ID NO: 14 |
| D35(TG)C-dAs40 | GsGTGCATTGATGCACCCCsCsCs-As40 | | 15 | SEQ ID NO: 15 |
| D35(CT)C-dAs40 | GsGTGCATCTATGCACCCCsCsCs-As40 | | 16 | SEQ ID NO: 16 |
| | | | | |
| D35T-dAs40** | GsTGCATCGATGCATTTTsTsTS-AS40 | FIG. 1B | 1 | SEQ ID NO: 9 |
| D35T-dA40 | GsTGCATCGATGCATTTTsTsTs-A40 | | 2 | SEQ ID NO: 17 |
| D35T-dTs40 | GsTGCATCGATGCATTTTsTsTs-TS40 | | 3 | SEQ ID NO: 18 |
| D35T-dT40 | GsTGCATCGATGCATTTTsTsTs-T40 | | 4 | SEQ ID NO: 19 |
| D35T-dCs40 | GsTGCATCGATGCATTTTsTsTs-Cs40 | | 5 | SEQ ID NO: 20 |
| D35T-dC40 | GsTGCATCGATGCATTTTsTsTs-C40 | | 6 | SEQ ID NO: 21 |
| | | | | |
| D35-dAs40* | GsGTGCATCGATGCAGGGGsGsGs-As40 | FIG. 4A | | SEQ ID NO: 1 |
| D35T-dAs40** | GsGTGCATCGATGCATTTTsTsTs-As40 | FIG. 4B | | SEQ ID NO: 9 |
| D35core | TGCATCGATGCA | | | SEQ ID NO: 22 |
| D35core-dAs40 | TGCATCGATGCA-As40 | | | SEQ ID NO: 23 |
| D35coreT-dAs40 | TGCATCGATGCATTTTsTsTs-As40 | | | SEQ ID NO: 24 |

TABLE 1 -continued

Modified D35 ODNs developed in the present
invention (SEQ ID NOs: 1-28)

| | | | |
|---|---|---|---|
| D35core-dAs10 | TGCATCGATGCA-As10 | FIG. 4C | SEQ ID NO: 75 |
| D35core-dAs20 | TGCATCGATGCA-As20 | FIG. 4D | SEQ ID NO: 26 |
| D35core-dAs30 | TGCATCGATGCA-As30 | | SEQ ID NO: 27 |
| D35c0re-dAs40 | TGCATCGATGCA-As40 | | SEQ ID NO: 28 |

"s" indicates a phosphorothioate backbone.
*D35(CG)G-dAs40 and D35-dAs40 have the same sequence.
**D35(CG)T-dAs40 and D35T-As40 have the same sequence.

Poly-dAs40 tail (SEQ ID NO: 29) was tested as an exemplary agent for delivery in FIG. 1A.

PBMCs were stimulated for 24 hours with K3, D35, D35-dAs40, and other ODNs (Table 1) at the shown concentrations. Stimulation with an ODN and DOTAP (Roche) was carried out according to the manufacturer's instruction. Briefly stated, an ODN solution in a serum-free medium (Opti-MEM; Gibco) and a DOTAP solution in Opti-MEM were prepared separately, maintained for 15 minutes at room temperature, and then thoroughly mixed by pipetting the ODN solution and the DOTAP solution. The resulting ODN/DOTAP mixture was maintained for 15 minutes at room temperature. The ODN/DOTAP mixture (100 µL) was added to the human PBMCs (2×10$^6$ cells/100 µL/well). After 24 hours, the supernatant was assayed for the presence of cytokines.

(Measurement of Cytokines by Enzyme-Linked Immunosorbent Assay (ELISA))

A generic IFN-α ELISA kit (Mabtech or PBL) and human IL-6 ELISA kit (DuoSet; R&D Systems) were used according to the instruction manual of the manufacturer to measure cytokines in the supernatant. ELISA used 3,3',5,5'-tetramethylbenzidine (TMB) (KPL) for coloring. In some of the experiments, Milliplex assay (MPXHCYTO60KPMX26; Millipore) was also carried out according to the manufacturer's instruction.

(Dynamic Light Scattering (DLS))

Wyatt DynaPro PlateReader II (Wyatt Technology, USA) was used to measure DLS. Samples (stored for over 18 hours at 1 mg/mL in PBS) were measured (obtained 20 times at 25° C.) in a 384 well plate (20 µL/well). Polydispersity, hydrodynamic radius, and molecular weight were analyzed with Dynamics software v7.1.7.16 (Wyatt Technology, USA).

(Transmission Electron Microscopy (TEM))

D35 (1 mg/mL in PBS) was dripped into a Formvar-carbon coated grid (10 µL) and incubated for 2 hours for adhesion to the grid. For negative staining, the sample was washed three times with distilled water, and then one droplet of 2% (wt/vol) uranyl acetate (pH 4.0) was placed on the grid and was air-dried. The grid was studied at a 10,000× magnification with an electronic microscope (Hitachi H-7650).

(Complexation of CpG ODN and Schizophyllan (SPG))

A solution (15 mg/mL in 0.25 N NaOH) of alkaline denatured SPG (molecular weight 150,000) was added to an ODN solution (100 µM in NaH$_2$PO$_4$) and thoroughly mixed. The mixture was left standing overnight at 4° C. to complete the complexation. The mole ratio (SPG:DNA) was fixed at 0.27. The complexation efficiency between ODN and SPG was estimated from residual free ODNs in the mixture solution by using a MultiNA Microchip Electrophoresis System (Shimadzu Corp., Kyoto).

(Cynomolgus Monkey Immunization)

Cynomolgus monkeys (*Macaca fascicularis*) were obtained and kept by the Tsukuba Primate Research Center of the National Institutes of Biomedical Innovation, Health and Nutrition (NIBIO). All experiments were conducted under the protocol approved by the Committee on the Ethics of Animal Experiments of NIBIO (Permit Number: DS22-4R1). Various efforts were made to minimize the slaughtering. On day 0 and day 14, cynomolgus monkeys were subcutaneously (s.c.) injected with influenza split vaccine (SV) (5 µg) (A/New Caledonia/20/99, BIKEN), with or without K3 (4.7 nmol), D35 (4.7 nmol), D35-dAs40 (4.7 nmol), D35core-dAs40 (4.7 nmol), or D35-SPG (4.7 nmol as the amount of D35-dAs40). Serum was collected at 4 and 8 weeks after priming. Anti-SV total IgG in the serum was measured by ELISA. Each serum sample was serially diluted to calculate the antibody titer as a reciprocal number of the dilution ath 0D450=0.2.

(Statistical Analysis)

Graphpad Prism 5 software was used to calculate a statistically significant difference. Cytokine analysis used a paired t-test, and antibody titer analysis used a two-sided nonparametric Mann-Whitney U test.

(Details of Experiment)

(Poly dAs40 Tailed A/D-Type ODNs have Similar Immunostimulatory Potential to Original D35)

The inventors developed K3-SPG, a second generation B/K type CpG adjuvant, which is a particulate soluble complex of a K3 CpG-ODN and schizophyllan (SPG) [Kobiyama K et al., (2014) Proceedings of the National Academy of Sciences, vol. 111 no. 83086-3091, doi: 10.1073/pnas. 1319268111; Koyama S et al., (2010) Science Translational Medicine 2:25ra24]. In order to form a complex of a K3 ODN and SPG, the 3' end must be modified by adding a phosphorothioate 40-mer of deoxyadenylic acids (dAs40 tail). At the 3' end, SPG and the dAs40 tail form a triple helix complex [Kobiyama K et al., (2014), supra]. Concurrently with these experiments, the inventors also synthesized D35 ODNs added with a similar tail to study the immunostimulatory activity thereof (IFN-α and IL-6 induction) on human PBMCs. Cytokine ELISA revealed that D35 with a dAs40 tail added to the 3' end (A/D type CpG-ODN) has the same activity as the original D35 (1 in FIG. 1A and D35 are compared; each ODN sequence used in the experiment is shown in Table 1). Subsequent experiments further revealed that some D35 derived ODNs with a dAs40 tail also have biological activity even when a guanine hexamer at the 3' is replaced with an adenine, thymine, and cytosine hexamer (see 5, 9, and 13 of FIG. 1A). This result was rather unexpected because guanine hexamers form a quadruplex structure by Hoogsteen base pair formation, resulting in self-aggregation [Costa L T et al., (2004) Biochemical and Biophysical Research Communications 313: 1065-1072; Klein D C et al., (2010) Ultramicroscopy 110: 689-693.], where aggregation via a guanine hexamer was considered an unavoidable element for biological activity of A/D type CpG ODNs [Verthelyi D et al., (2001) J Immunol 166:2372-2377; Kerkmann M et al., (2005) J Biol Chem 280: 8086-8093; Wu C C et al., (2004) J Biol Chem 279: 33071-33078; Puig M et al., (2006) Nucleic Acids Res 34: 6488-6495.] Meanwhile, the immunostimulatory activity of ODNs derived from D35 on human PBMCs was completely dependent on the presence of a CpG sequence. This was in agreement with the non-methylated CpG motif theory [Krieg A M (2002) Annual Review of Immunology 20: 709-760.] (comparison of 9 and 10-12 in FIG. 1A). These results indicate that the presence of a guanine hexamer sequence is not an essential requirement for the immunostimulatory activity of A/D type ODNs, while the activity of ODNs derived from D35 is strongly dependent on the presence of a CpG motif sequence.

(Phosphorothioate Polynucleotide Tail is Required for Immunostimulatory Activity of ODNs Derived from D35)

Addition of a guanine hexamer to a phosphodiester CpG ODN is known to improve the cellular uptake thereof [Bartz H et al., (2004) Vaccine 23: 148-155; Dalpke A H et al., (2002) Immunology 106: 102-112.] In line with this fact, phosphorothioate ODNs were shown to non-specifically bind to proteins [Brown D A et al, (1994) Journal of Biological Chemistry 269: 26801-26805.] Furthermore, phosphorothioate CpG ODNs were shown to be more effectively uptaken by cells than phosphodiester CpG ODNs. These findings suggest that an addition of a dAs40 tail is likely to have improved cell uptake of ODNs by a non-specific bond via the phosphorothioate backbone. Based on these reports, the inventors have compared immunostimulatory activity of D35T-dAs40 and D35T-dA40 (the original guanine hexamer is replaced with thymine hexamer, and the tail is comprised of either phosphorothioate or phosphodiester poly-A40) on human PBMCs to examine the chemical backbone structure requirement (comparison of 1 and 2 in FIG. 1B). The biological activity of ODNs was dependent on the presence of a phosphorothioate tail, while cytokine reactions were hardly observed with an addition of a phosphodiester tail ODNs (comparison of 1 and 2 in FIG. 1B). The inventors also examined other polynucleotide 40-mer tails such as poly-T(s)40 and poly-C(s)40 instead of poly-A(s)40. It was found that a relatively stronger cytokine reaction was observed when adding a dAs40 tail or a dCs40 tail than a dTs40 tail (see 1, 3, and 5 of FIG. 1B), while cytokine reactions were unrelated to the base of a polynucleotide tail, but were dependent on the presence of a phosphorothioate backbone (see 3-6 in FIG. 1B).

(DOTAP Compensates for the Absence of a G-Hexamer Sequence)

Figure 2:
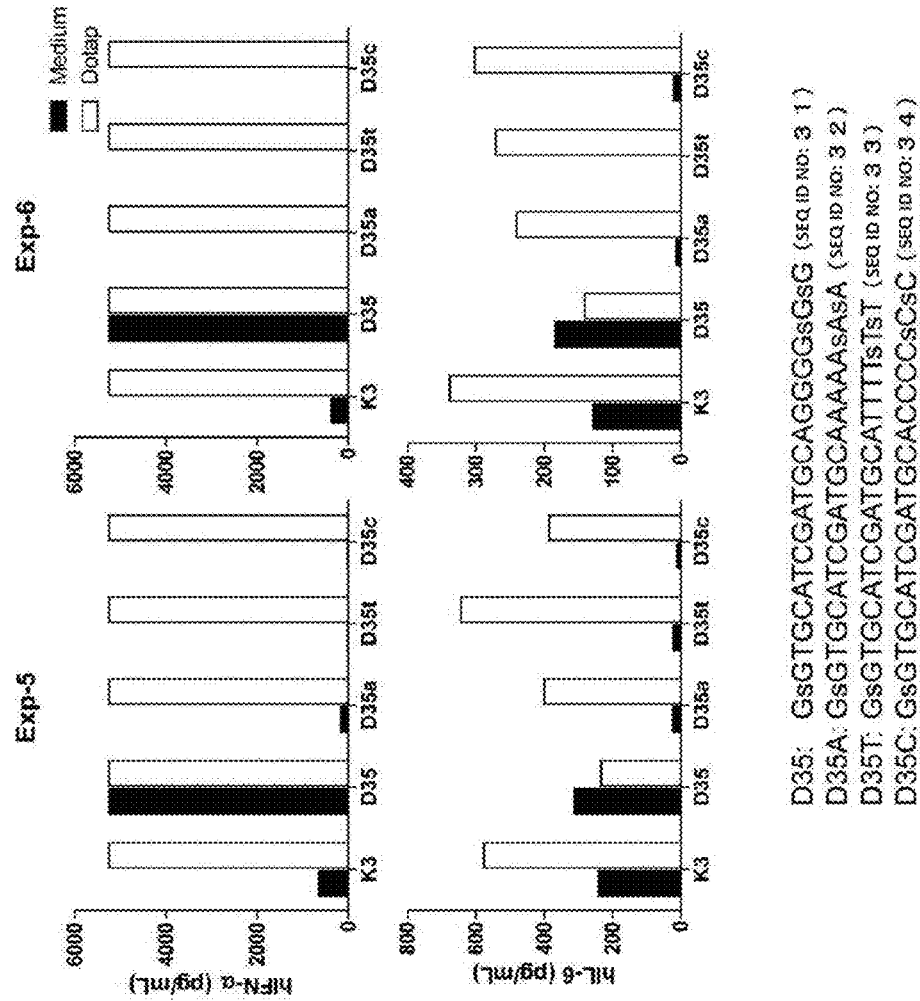
FIG. 2 shows that guanine hexamer-free D35 ODNs require DOTAP for immunostimulatory activity. Human PBMCs were stimulated for 24 hours with the shown synthetic ODNs (1 µM) with or without DOTAP, and IFN-α and IL-6 production in the supernatant was measured by ELISA. DOTAP rescued the immunostimulatory activity of guanine hexamer-free A/D type ODNs, D35A, D35T, and D35C. These ODNs did not exhibit immunostimulatory activity without DOTAP. The bar graphs show the cytokine concentration from a single well for each stimulation.

The inventors tested immunostimulatory activity on human PBMCs of D35 comprising adenine, thymine, and cytosine hexamers without a phosphorothioate polynucleotide tail (FIG. 1C). The immunostimulatory activity of the original D35 was dependent on the presence of a guanine hexamer, which was consistent with previous reports [Verthelyi D et al., (2001) J Immunol 166: 2372-2377; Yamamoto T et al., (1994) Microbiol Immunol 38: 831-836; Lee S W et al., (2000) The Journal of Immunology 165: 3631-3639] (FIG. 2). D35 comprising adenine, thymine, and cytosine hexamers (D35A, D35T, and D35C) did not have an effect on human PBMCs (FIG. 2; black bars). In this regard, when DOTAP was added thereto, the same ODNs had relative high activity (FIG. 2, white bars). DOTAP is a cationic lipid (N-[1-(2,3-dioleyloxy)propyl]-N,N,N-trimethylammonium methyl sulfate), which is used for targeting CpG-ODN to a specific endosomal compartment for initiating TLR9-mediated signaling [Yasuda K et al., (2005) Journal of immunology (Baltimore. Md: 1950) 174: 6129-6136; Honda K et al., (2005) Nature 434: 1035-1040.] The result demonstrated that biological activity of A/D type ODNs does not require a sequence of a guanine hexamer for targeting ODNs to a suitable endosomal compartment and cellular uptake by DOTAP.

In summary, these results suggest that immunostimulatory activity of A/D type CpG-ODNs can be regulated by two separate processes. The first process is efficient cell uptake by either aggregation of guanine hexamers or nonspecific bond via a phosphorothioate polynucleotide tail. The second process is due to the presence of a CpG motif that induces TLR dependent signaling. DOTAP can convert non-active guanine hexamer-free D35 such as D35A, D35T, and D35C into an immunostimulatory compound. Thus, it is suggested that the presence of a guanine hexamer sequence itself is not essential for CpG motif/TLR9 molecular interaction.

(dAs40 Tailed D35 ODNs do not Form Large Aggregates)

Figure 3:
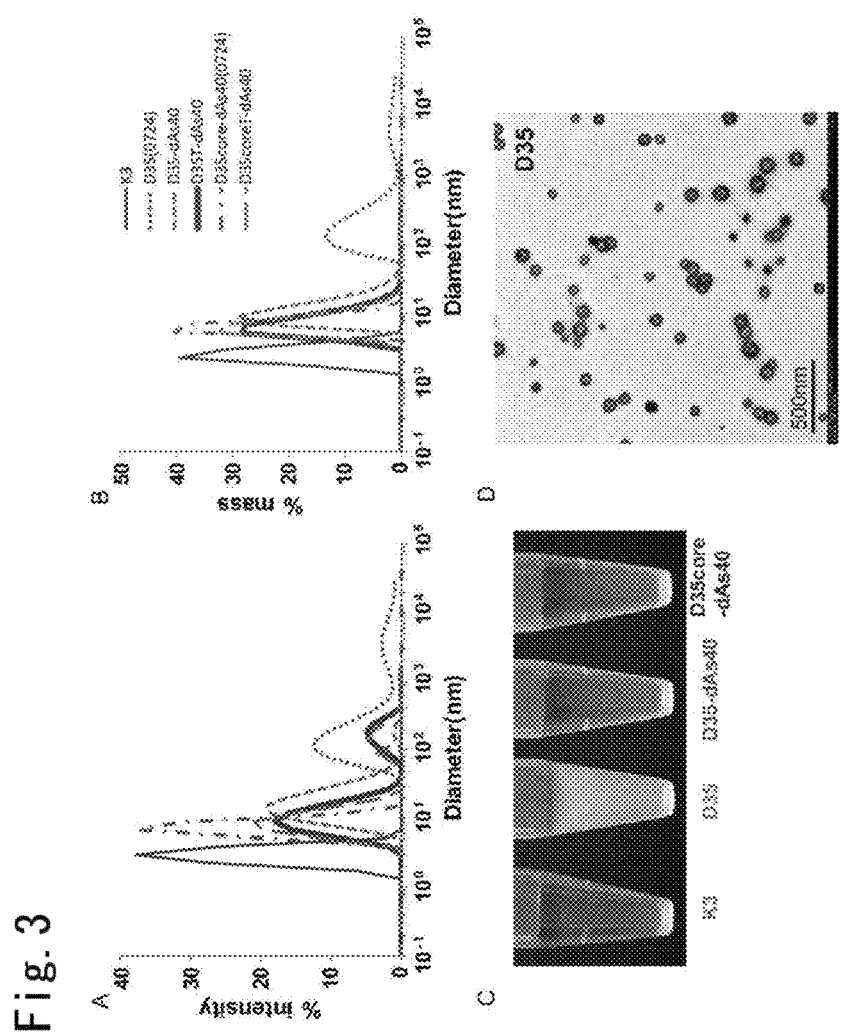
FIG. 3 shows physical properties of polynucleotide tailed A/D type ODNs in a PBS solution. Results of DLS analysis for the shown ODN solutions (1.0 mg/mL each in PBS) are shown by (A) % intensity plots and (B) % mass plots. Please refer to Table 2 for each measurement result. (C) shows the turbidity of the shown ODN solutions. The shown ODNs were first dissolved into distilled water at a concentration of 10 mg/mL (all ODNs completely dissolved into water, and the solutions were transparent), and were then diluted with PBS to a final concentration of 1.0 mg/mL. The solutions were stored for at least 18 hours at 4° C., and then pictures were taken. D35 resulted in cloudiness that was visible to the eyes during the incubation period. In contrast, other ODNS remained transparent. (D) shows a TEM image of D35 that aggregated in PBS which was prepared in the same manner as in (C).
Figure 5:
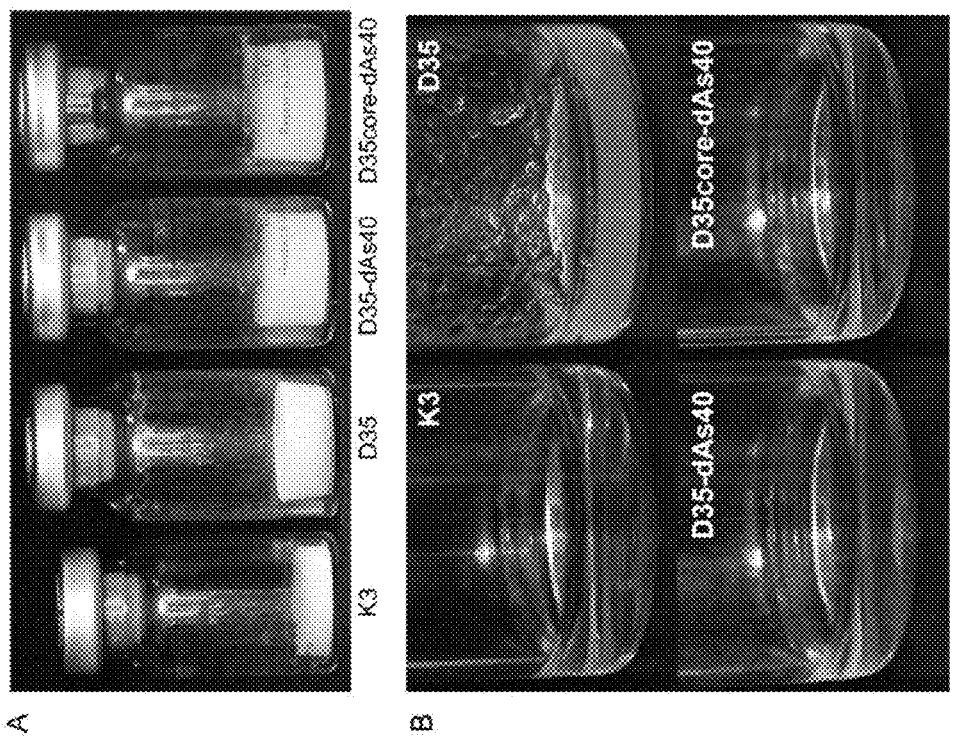
FIG. 5 shows that D35-dAs40 and D35core-dAs40 directly dissolve into saline, but that the original D35 does not. (A) shows a picture of GMP grade lyophilized ODN vials for K3, D35, D35-dAs40, and D35core-dAs40 (10 mg/vial). The white substances are lyophilized synthetic ODNs. (B) Saline (1 mL) was added directly to each vial. K3, D35-dAs40, and D35core-dAs40 completely dissolved into saline in 5 minutes or less. D35 did not completely dissolve into saline. Many visible gelatinous aggregates were formed. This insoluble state did not changed for at least one month.

The inventors have also studied the physical properties of several ODNs related to dAs40 tailed D35 by using dynamic light scattering (DLS) (FIG. 3). Synthesis of a clinically applicable A/D type ODN at a quality meeting the Good Manufacturing Practice (GMP) is obstructed by G tail dependent multimerization, which leads to uncontrollable polymorphism, aggregation and precipitation of ODN products [Puig M et al., (2006) Nucleic Acids Res 34: 6488-6495.] (FIGS. 3 and 5). The original D35 (1 mg/mL) exhibited formation of various visible heterogeneous aggregates in PBS and resulted in visible turbidity within 24 hours (FIG. 3C). In particular, turbidity was not observed for D35 in water. DLS analysis revealed that turbidity consisted of widely dispersed aggregates (mean diameter size in the range of about 50 nm to greater than 1 μm) (FIGS. 3A-3B). In contrast, D35-dAs40 and D35core-dAs40 at the same concentration in PBS did not form visible precipitation (FIG. 3C), while the size of ODNs was less than 20 nm and had a sharp peak according to DLS (FIGS. 3A-3B and Table 2).

TABLE 2

Results of DLS measurement for each ODN in FIG. 3

| | Diameter (nm) | % Pd | Mw-R (kDa) | % intensity | % mass | SEQ ID NO. |
|---|---|---|---|---|---|---|
| K3 | 2.7 | 26.0 | 7 | 100.0 | 100.0 | 30 |
| D35 | 213.2 | 74.2 | 187014 | 77.1 | 79.7 | 31 |
| D35-dAs40 | 11.8 | 48.7 | 212 | 97.2 | 99.9 | 1 |
| D35T-dAs40 | 7.6 | 43.3 | 76 | 80.6 | 99.6 | 9 |
| D35core-dAs40 | 6.9 | 23.5 | 61 | 96.6 | 100.0 | 23 |
| D35coreT-dAs40 | 7.3 | 35.4 | 70 | 79.4 | 99.6 | 24 |

The value of the primary peak is shown for measurement values of each ODN.
Pd means polydispersity Transmission electron microscope (TEM) analysis confirmed the results from DLS and showed that many spherical particles with a size of about 50-200 nm were individually dispersed or formed a cluster of several linked particles (FIG. 3D), which was consistent with previous reports [Costa L T et al., (2004) Biochemical and Biophysical Research Communications 313: 1065-1072; Klein D C et al., (2010) Ultramicroscopy 110: 689-693.] These data show that an addition of a dAs40 tail significantly improves physical homogeneity of A/D type ODNs in PBS. Such ODNs comprising a guanine hexamer sequence such as D35-dAs40 substantially did not exhibit aggregation by adding a dAs40 tail. A significant structure was observed by TEM for K3, D35-dAs40, D35T-dAs40, D35core-dAs40, and D35coreT-dAs40.

(dAs40 Tailed D35 Related ODNs Induce INF-α in a Dose Proportional Manner)

The inventors further evaluated immunostimulatory activity of these ODNs by volumetric titration (FIG. 4A). All ODNs including D35, D35-dAs40 (comprising a guanine hexamer sequence), and D35core-dAs40 (not comprising a guanine hexamer sequence) induced dose dependent increase in INF-α and IL-6 reactions from human PBMCs (FIG. 4A). In contrast, the recently reported P type ODN, 21889 (which is comprised of a phosphorothioate backbone comprising two palindromic sequences for promoting the aggregate formation of a dimeric structure in series) [Samulowitz U et al., (2010) Oligonucleotides 20: 93-101.] exhibited a decrease in IFN-α and IL-6 reactions when used at a higher concentration (FIG. 4A).

(D35core+dAs40 Tail is Sufficient for IFN-α Production)

The inventors also studied the effect of adjacent sequences from a D35core 12-mer such as 5' GG sequence and 3' thymine hexamer on IFN-α production (FIG. 4B). A cytokine reaction was not induced only with a core sequence of D35 (12-mer) (FIG. 4B), but an addition of a dAs40 tail to this 12-mer was sufficient to induce INF-α at a comparable amount. What is important is that this was a result in the absence of DOTAP. The presence of a thymine hexamer appeared to reduce biological activity. These results suggested that core adjacent sequences such as 5' GG sequence and 3' thymine hexamer were not essential for immunostimulatory activity of this type of ODN (FIG. 4B).

(Longer Phosphorothioated-A-Tailed ODNs have Increased Immunostimulatory Activity)

The inventors also studied the effect of the length of phosphorothioate A polymer tail on immunostimulatory activity. When human PBMCs were stimulated with the same amount of the shown ODN (1 µM), IFN-α and IL-6 production had a positive correlation with the length of a dAs tail (FIG. 4C). When the effect of the concentration of each ODN was studied, it was suggested that increasing concentration of each ODN (maximum concentration examined was 9 µM) induced the same level of IFN-α and IL-6 production (FIG. 4D), and ODNs with a longer tail were uptaken more efficiently. However, it is likely that ODNs with a long tail and ODNs with a short tail use the same uptake mechanism, thus reaching a plateau-like cytokine reaction (FIG. 4D). In summary, the data shows that an addition of a phosphorothioate polynucleotide tail to a short ODN comprising a CpG motif is sufficient for producing an immunostimulatory A/D type ODN, so that this would be a useful strategy for producing A/D type ODNs which have controlled physical properties and comply with GMP.

(More Detailed Requirements and Characterization of Phosphorothioate Polynucleotide Tail)

Figure 4:
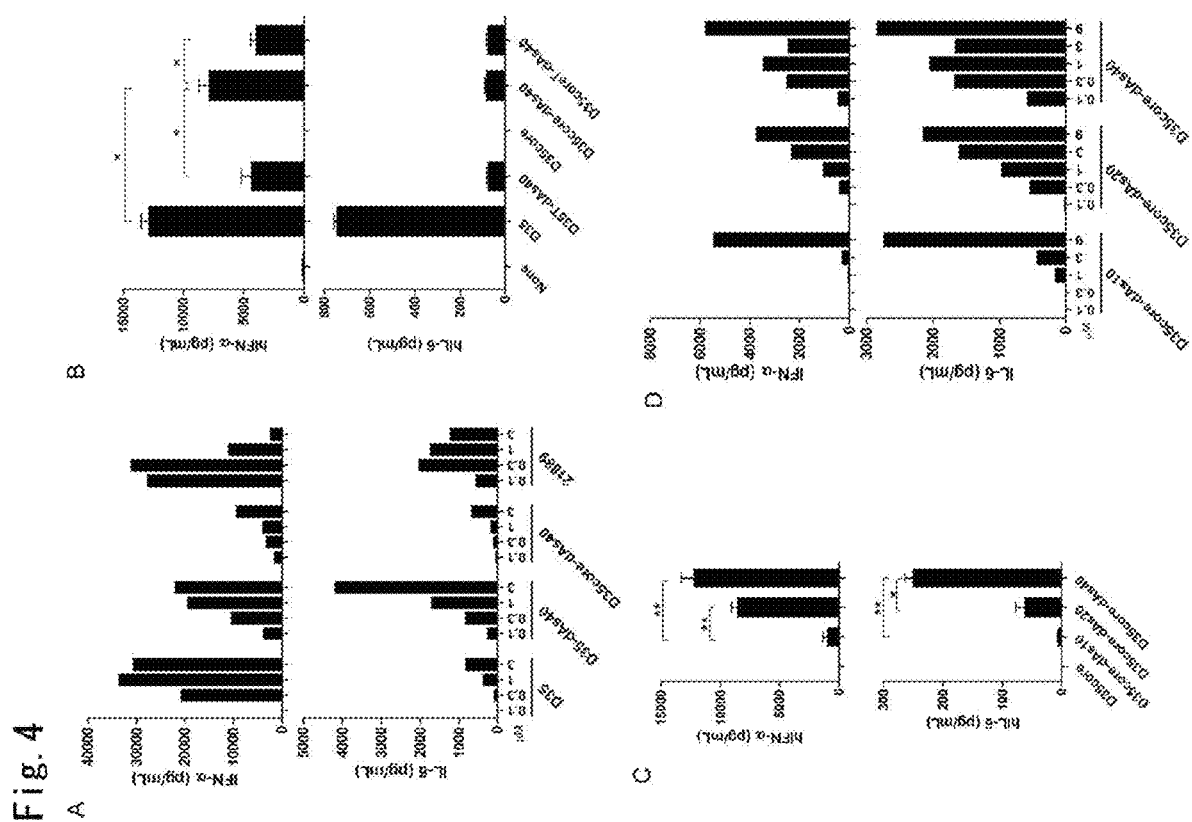
FIG. 4 shows biological activity of D35-dAs40 and D35core-dAs40. (A) shows dosage-dependent IFN-α production from human PMBCs by the shown ODNs. (B) shows the effect of an adjacent sequence on cytokine induction activity. D35core+dAs40 is sufficient for inducing IFN-α secretion from human PBMCs. The bars indicate the mean±SEM of three experiments. (C) shows that the length of a dAs tail affects the biological activity of D35core-dAs type ODNs. Human PBMCs were stimulated with the shown ODNs (final concentration of 1 μM), and the cytokine concentration was measured by ELISA after 24 hours. The bars indicate the mean±SEM of three experiments. (D) shows the relationship between the tail length and ODN dosage for the shown ODNs. The bar graphs indicate dosage dependent IFN-α and IL-6 production from a single well for each stimulation. *p<0.05, **p<0.01.
Figure 9:
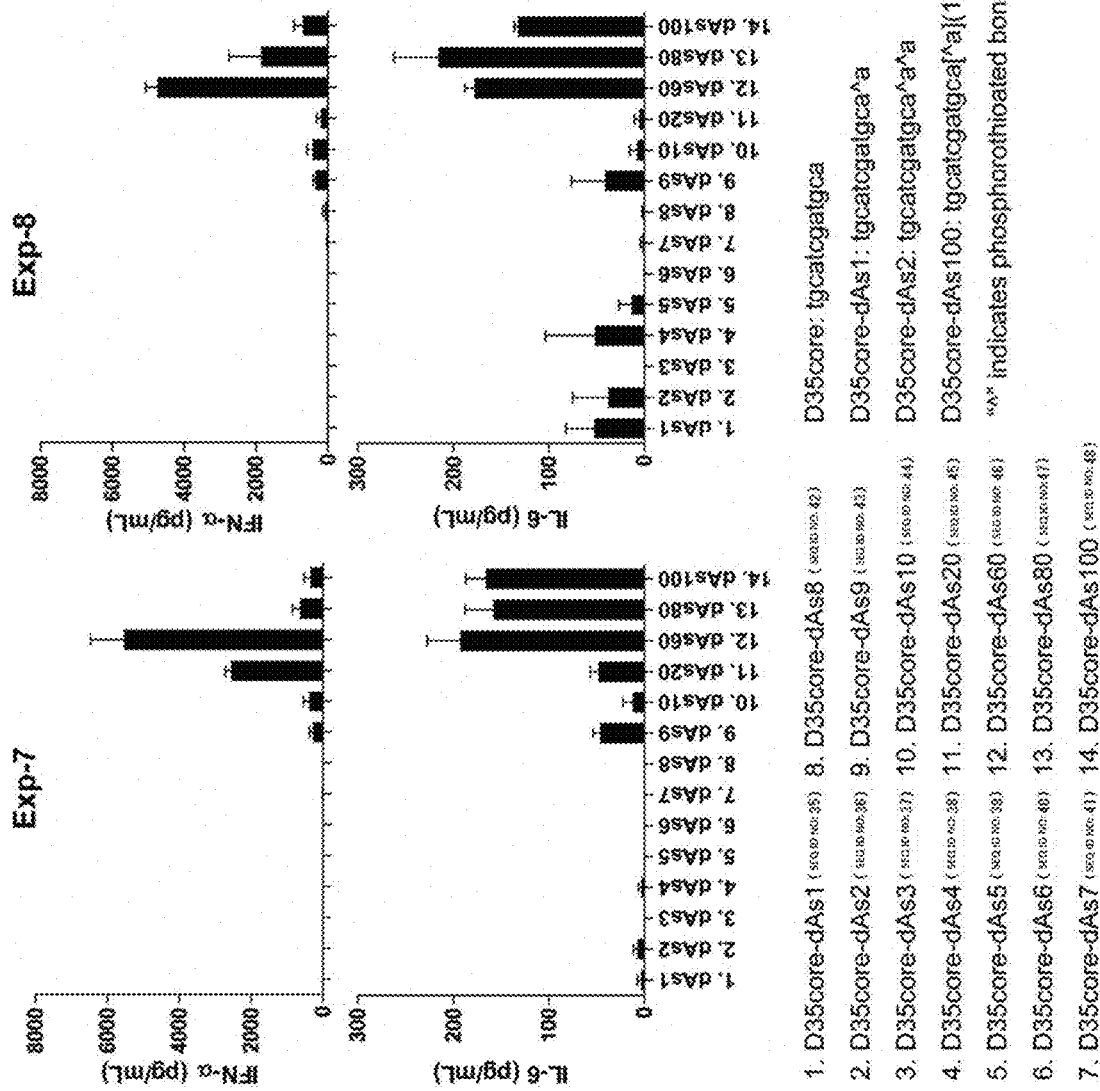
FIG. 9 studied the effect of the tail length on immunostimulatory activity. Human PBMCs were stimulated over 24 hours with synthetic ODNs (1 μM) shown in the Figure. IFN-α and IL-6 production in the supernatant was tested by ELISA. Each of the symbols in the Figure is the following: 1. D35core-dAs1 (SEQ ID NO: 35); 2. D35core-dAs2 (SEQ ID NO: 36); 3. D35core-dAs3 (SEQ ID NO: 37); 4. D35core-dAs4 (SEQ ID NO: 38); 5. D35core-dAs5 (SEQ ID NO: 39); 6. D35core-dAs6 (SEQ ID NO: 40); 7. D35core-dAs7 (SEQ ID NO: 41); 8. D35core-dAs8 (SEQ ID NO: 42); 9. D35core-dAs9 (SEQ ID NO: 43); 10. D35core-dAs10 (SEQ ID NO: 44); 11. D35core-dAs20 (SEQ ID NO: 45); 12. D35core-dAs60 (SEQ ID NO: 46); 13. D35core-dAs80 (SEQ ID NO: 47); and 14. D35core-dAs100 (SEQ ID NO: 48). D35core has the sequence tgcatcgatgca (SEQ ID NO: 22), D35core-dAs1 has the sequence tgcatcgatgcaˆa (SEQ ID NO: 35), and D35core-dAs2 has the sequence tgcatcgatgcaˆaˆa (SEQ ID NO: 36). In this manner, D35core-dAsN (N is a number) indicates the number of adenines bound to the sequence of D35core by a phosphorothioate bond in order. Thus, D35core-dAs100 is tgcatcgatgca[ˆa](100) (SEQ ID NO: 48) (i.e., this means that 100 adenines with a phosphorothioate bond are bound to D35core). ˆ indicates a phosphorothioate bond.
Figure 10:
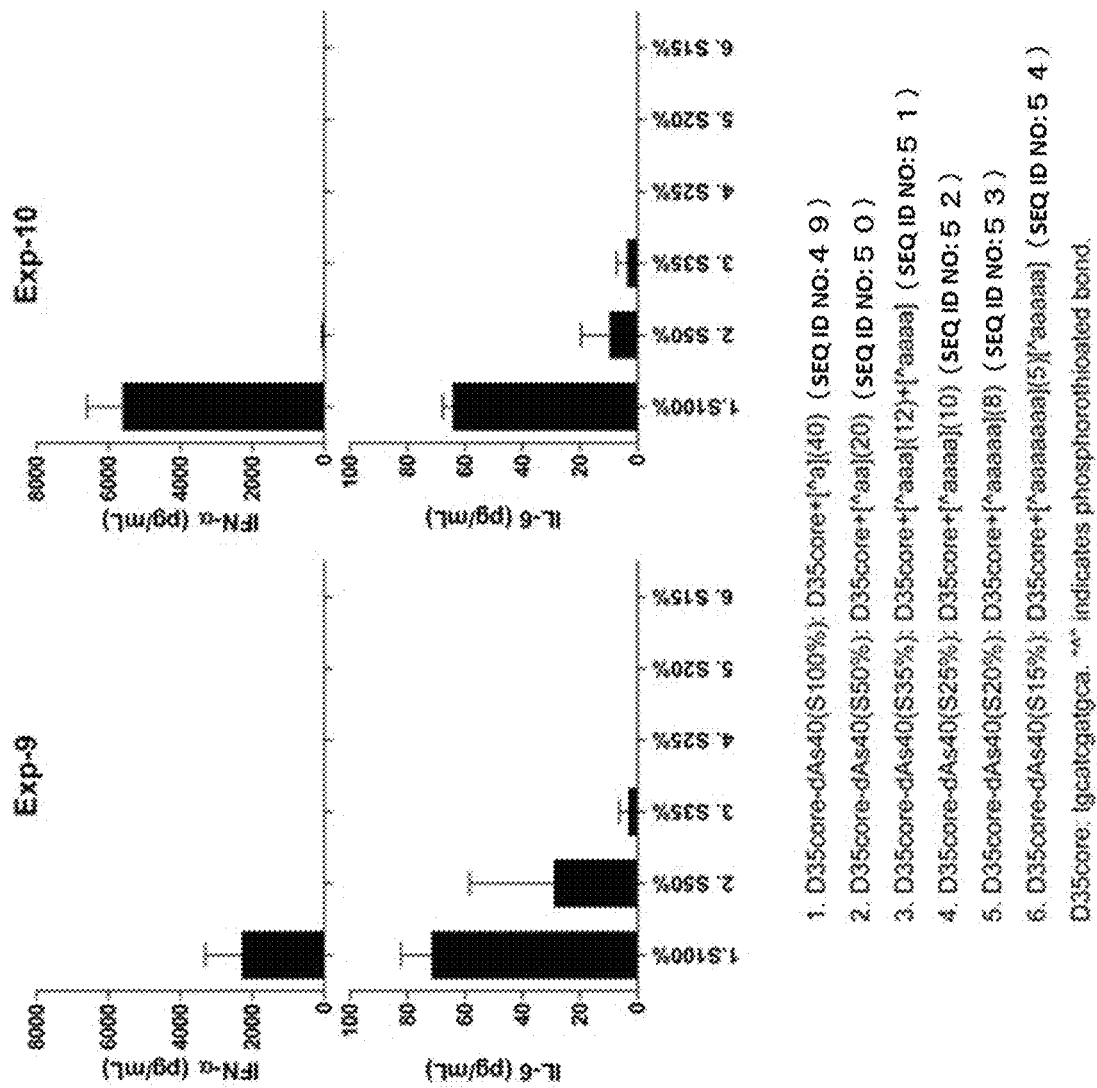
FIG. 10 studied the effect of the amount of phosphorothioate in the tail on immunostimulatory activity. Human PBMCs were stimulated over 24 hours with the synthetic ODNs shown in the Figure (1 μM). IFN-α and IL-6 production in the supernatant was tested by ELISA. The symbols in the Figure are the following: 1. D35core-dAs40 (S100%): D35core+[ˆa](40) (SEQ ID NO: 49) (i.e., 40 adenines with a phosphorothioate bond are bound to a D35core); 2. D35core-dAs40(S50%) (i.e., 20 dimers of adenines with a phosphorothioate bond and adenines with a normal bond are bound to a D35core): D35core+[ˆaa](20) (SEQ ID NO: 50); 3. D35core-dAs40(S35%): D35core+[ˆaaa](12)+[ˆaaaa] (SEQ ID NO: 51) (12 trimers of one adenine with a phosphorothioate bond and two adenines with a normal bond are bound to D35core, and a tetramer of one adenine with a phosphorothioate bond and three adenines with a normal bond are further bound thereto); 4. D35core-dAs40(S25%): D35core+[ˆaaaa](10) (SEQ ID NO: 52) (i.e., 10 tetramers of an adenine with a phosphorothioate bond and three adenines with a normal bond are bound to a D35core); 5. D35core-dAs40(S20%): D35core+[ˆaaaaa](8) (SEQ ID NO: 53) (i.e., 8 pentamers of an adenine with a phosphorothioate bond and four adenines with a normal bond are bound to a D35core); 6. D35core-dAs40(S15%): D35core+[ˆaaaaaaa](5)[ˆaaaaa](1) (SEQ ID NO: 54) (i.e., five heptamers of an adenine with a phosphorothioate bond and six adenines with a normal bond are bound to a D35core, and a pentamer of one adenine with a phosphorothioate bond and four adenines with a normal bond is further bound thereto); the D35core has tgcatcgatgca; and ˆ indicates a phosphorothioate bond.
Figure 11:
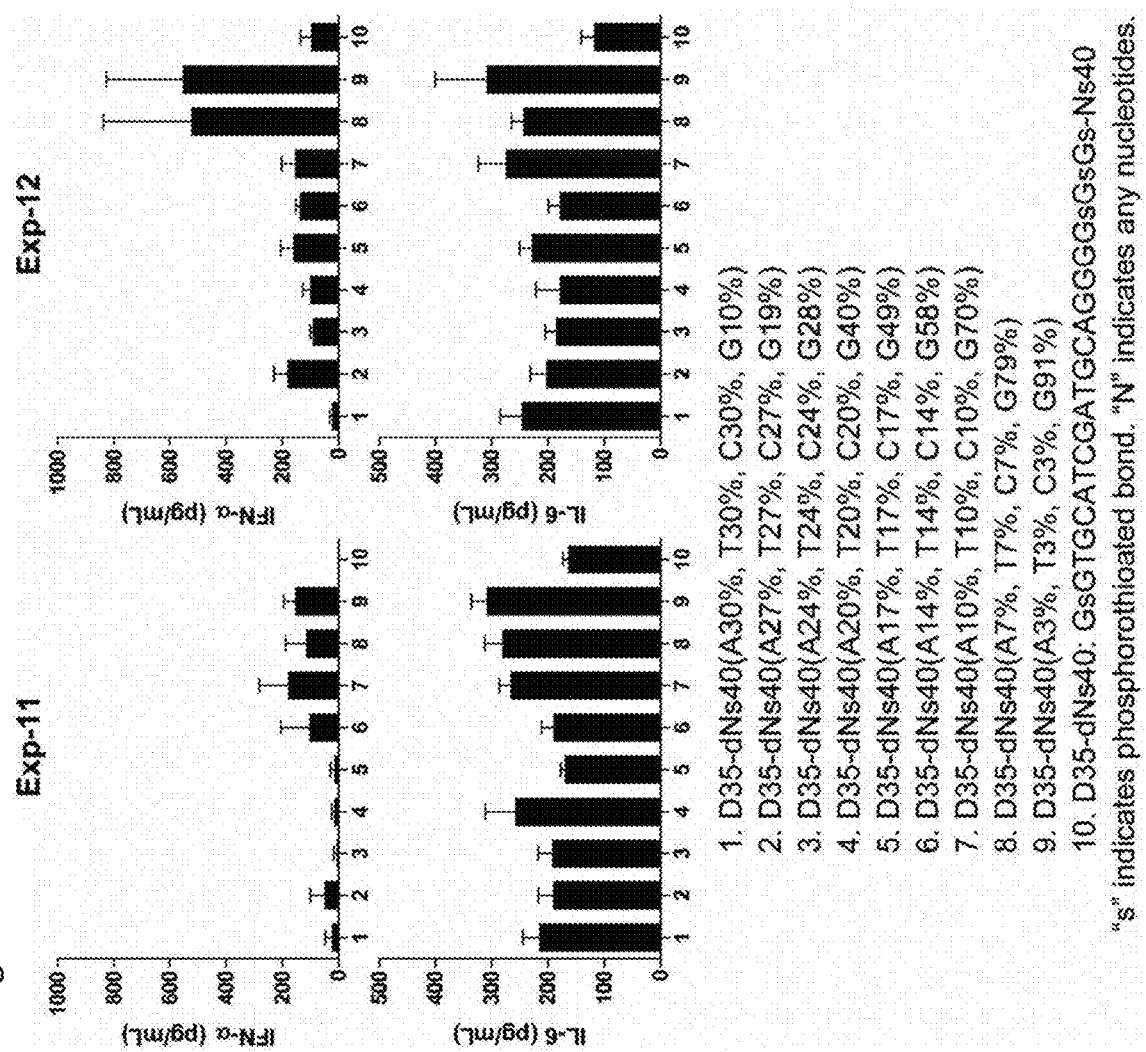
FIG. 11 shows results of studying the effect of nucleoside composition in a tail on immunostimulatory activity. Human PBMCs were stimulated over 24 hours with the synthetic ODNs (1 µM) shown in the Figure. IFN-α and IL-6 production in the supernatant was tested by ELISA. It is particularly of note that D35-dNs40 (No. 10) substantially did not induce IFN-α production. The Figure shows the following: 1. D35-dNs40 (A30%, T30%, C30%, G10%); 2. D35-dNs40 (A27%, T27%, C27%, G19%); 3. D35-dNs40 (A24%, T24%, C24%, G28%); 4. D35-dNs40 (A20%, T20%, C20%, G40%); 5. D35-dNs40 (A17%, T17%, C17%, G49%); 6. D35-dNs40 (A14%, T14%, C14%, G58%); 7. D35-dNs40 (A10%, T10%, C10%, G70%); 8. D35-dNs40 (A7%, T7%, C7%, G79%); 9. D35-dNs40 (A3%, T3%, C3%, G91%); 10. D35-dNs40: GsGTGCATC-GATGCAGGGGsGsGs-Ns40 (SEQ ID NO: 72). "s" indicates a phosphorothioated bond. N indicates any nucleotide. It should be noted that the specific sequence is not defined for 1-9 because the individual sequences were randomly made by defining only the % of constitution of bases.

The inventors further conducted a series of experiments for the understanding of the requirements for phosphorothioate polynucleotides of D35 CpG ODNs (e.g., tail length (FIG. 9), degree of phosphorothioation of a tail (FIG. 10), and the nucleotide composition of a tail (FIG. 11)). First, D35core was tested for various numbers (length) of dAs with respect to IFN-α and IL-6 induction (FIG. 9). IFN-α induction was not observed for D35core and was slightly observed for dAs6. The amount of IFN-α increases as the length of dA approached dAs60. Interestingly, improvement was no observed with further extension of a dAs tail to 100, but rather the IFN-α induction decreased. In contrast, IL-6 production increased, and the increase was maintained up to dAs100. Phosphorothioation was then reduced from 100% to 15% by using D35core-dAs50 (FIG. 10). Even a 50% decrease in phosphorothioation in dA40 resulted in a dramatic decrease in IFN-α induction activity. Sensitivity of IL-6 production was not very high, but this also decreased quickly with the decrease in phosphorothioation. IL-6 production was not observed with phosphorothioation of 25% or lower. Thirdly, the requirements for the nucleotide composition were tested using D35-dNs40. Substantial IFN-α production was not induced for completely random dNs40 tailed ODNs (FIG. 11, nucleic acid number 10 (DS35-dNs40)). Increase in Hoogsteen base pair formation in the dNs40 tail is expected when the amount of guanosine in the dNs40 tail is increased from 10% to 90%. As the amount of guanosine increased, IFN-α production increased, but IFN-α induction remained relatively low even for D35-dNs40 (91% G) (FIGS. 4 and 9). Summarizing all the results, it is understood that each of 1) full length, 2) phosphorothioation, and 3) nucleotide composition (A-polymer is better than G-rich randomer) can be an important factor for the activity of an agent for immunostimulation of phosphorothioate polynucleotide tailed ODNs. In view of these results, the inventors selected D35-dAs40 and D35core-dAs40 as prototypes for clinical applications.

(Lyophilized D35-dAs40 and D35core-dAs40 in Vials can be Directly Formulated with Saline)

Direct solubility of an immunostimulatory ODN in salt-containing solution such as saline is an important requirement for facilitating the clinical application thereof. Thus, the inventors studied the direct solubility of lyophilized D35-dAs40 and D35core-dAs40 in saline. 1 mL of aqueous aseptic saline solution was directly poured into a vial containing 10 mg of lyophilized ODN (FIG. 5A). K3 and D35core-dAs40 readily dissolved in saline (FIG. 5B). D35-dAs40 (comprising a guanine hexamer sequence), albeit slowly, dissolved completely within 5 minutes (FIG. 5B). When such ODN solutions were stored for a month at 4° C., visible precipitation or aggregates were not observed. In contrast, the original D35 did not readily dissolve into saline, forming heterogeneous gelatinous aggregates (FIG. 5B). These results demonstrated that D35-dAs40 and D35core-dAs40 can be handled more readily than the original D35, especially for clinical applications.

(Conversion of D35 into Schizophyllan (SPG) Does Not Improve IFN-α Secretion from PBMCs)

Figure 6:
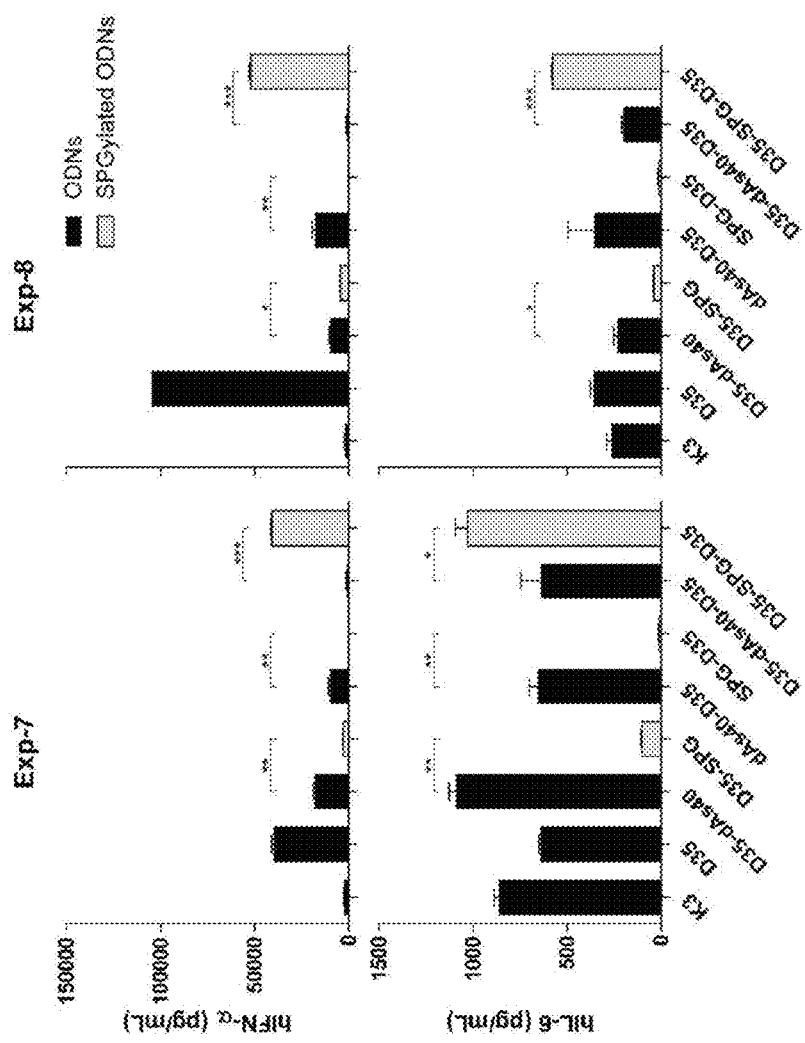
FIG. 6 shows the effects of modification by dAs40 of the 5' end and/or the 3' end of D35 or the SPGylation thereof on cytokine production from human PBMCs. Human PBMCs were stimulated with an ODN (D35-dAs40 (SEQ ID NO: 1), dAs40-D35 (SEQ ID NO: 74), D35-dAs40-D35 (SEQ ID NO: 75); 1 μM each) or SPGylated ODN thereof (D35-SPG, SPG-D35, or D35-SPG-D35; each in the amount of 1 μM of ODN), K3 (SEQ ID NO: 30), or D35 (SEQ ID NO: 31), and IFN-α and IL-6 secretion of the supernatant was measured by ELISA after 24 hours. The bars indicate the mean±SEM of three experiments. *p<0.05,  p<0.01, * p<0.001.
Figure 12:
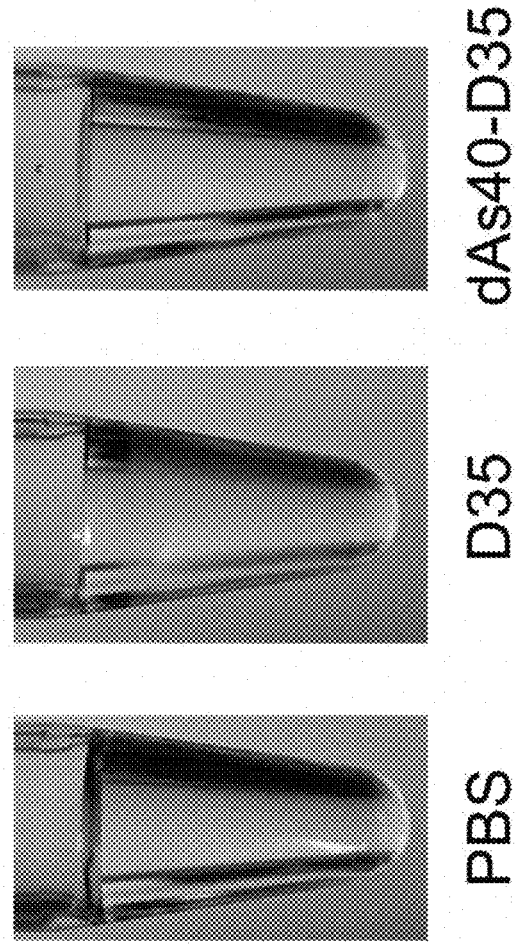
FIG. 12 shows that a large visible aggregate formation in PBS is also prevented with the addition of a dAs40 sequence to the 5' end of D35. When the shown ODNs were first dissolved into distill water at 10 mg/mL, all ODNs completely dissolved into water and the solutions were lucid. The ODNs were further diluted with PBS to a final concentration of 1.0 mg/mL. The solutions were stored for at least 18 hours at 4° C., and then pictures were taken. D35 was visibly cloudy after the incubation. In contrast, dAs40-D35 was not visibly cloudy.

Next, the inventors attempted to improve the immunostimulatory profile of ODNs derived from D35 by complex formulation (SPGylation) with schizophyllan (SPG). D35-SPG, SPG-D35, and D35-SPG-D35 were each prepared by complex formulation with SPG. Evaluation of the efficiency of complex formulation with a MultiNA Microchip Electrophoresis System resulted in the following: D35-SPG (99.4%), SPG-D35 (96.7%), and D35-SPG-D35 (49.8%). This indicates that ODNs in the solution of either D35-SPG or SPG-D35 were almost completely formulated, while only 50% of ODNs were formulated in the D35-SPG-D35 solution. Human PBMCs were stimulated with SPGylated ODNs to determine IFN-α and IL-6 secretion by ELISA (FIG. 6). In contrast to K3-SPG [Kobiyama K et al., (2014) Proceedings of the National Academy of Sciences, vol. 111 no. 8 3086-3091, doi: 10.1073/pnas.1319268111.], SPGylation of the 5' or 3' of D35 did not improve cytokine production, but reduced IFN-α and IL-6 secretion compared to ODNs without SPGylation (FIG. 6). In particular, D35-SPG had a greater immunostimulatory effect than SPG-D35 (FIG. 6). Particularly of note is that non-SPGylated ODNs with dAs40 added to the 5' or 3' end as in D35-dAs40 and dAs40-D35 exhibited comparable immunostimulatory activity (FIG. 6). However, the inventors observed slightly better cytokine production with D35-dAs40 than with dAs40-D35 in another experiment. Interestingly, visible large aggregate formation in PBS was not observed for dAs40-D35 (FIG. 12). D35-SPG-D35 significantly enhanced IFN-α and IL-6 secretion from PBMCs, but the efficiency of complex formulation was only about 50%. D35-SPG-D35 exhibited improvement in the cytokine profile similar to K3-SPG [Kobiyama K et al., (2014), supra].

(D35-dAs40, D35core-dAs40, and D35-SPG are Better Vaccine Adjuvants for Influenza Split Vaccines than K3 and Original D35 in Cynomolgus Monkeys)

Figure 7:
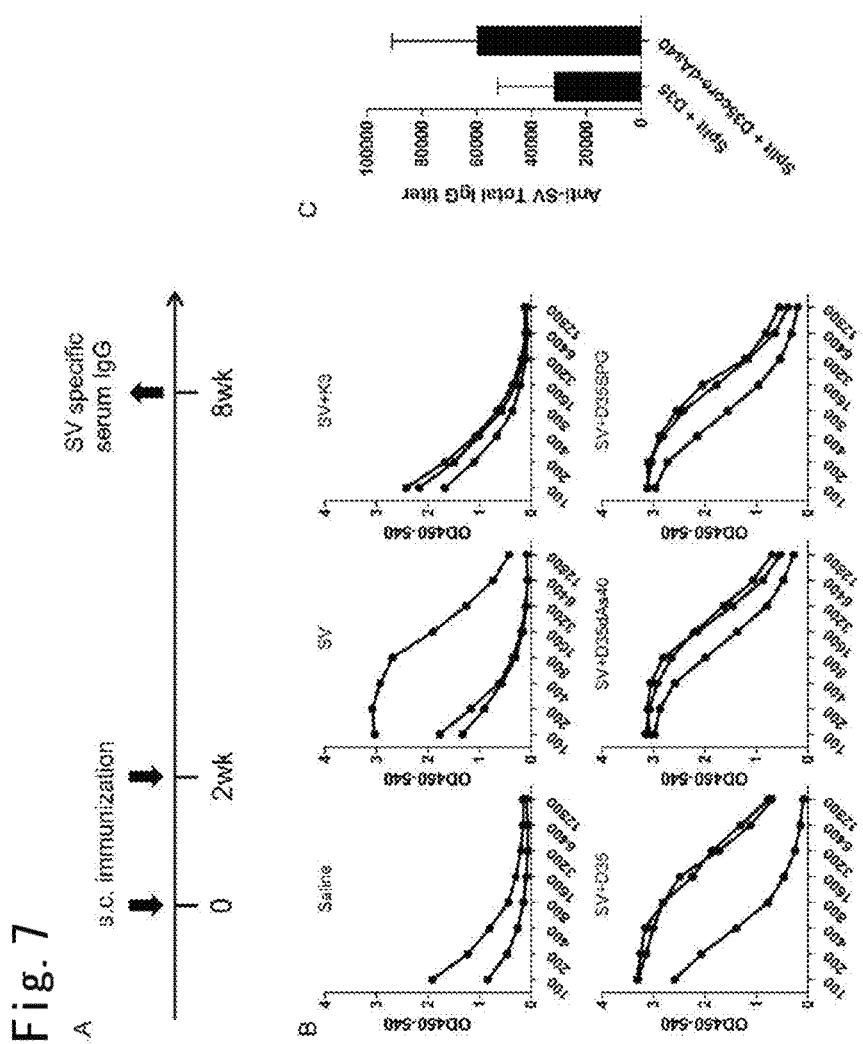
FIG. 7 shows that D35-dAs40, D35core-dAs40, and D35-SPG have excellent adjuvanticity when used with an influenza SV vaccine in cynomolgus monkeys. (A) shows the schedule of immunization and assays. Six groups of monkeys (n=2 or 3) were subcutaneously immunized twice at a two-week interval with a total volume of 500 μL of SV vaccine (A/New Caledonia/20/99, 5 μg/monkey), with or without the shown adjuvants (4.7 nmol each: K3, 30 μg; D35, 30 μg; D35-dAs40, 92 μg; and D35-SPG, 92 μg as the amount of D35-dAs40). (B) Anti-SV total IgG in the serum was measured by ELISA. The horizontal axis indicates the serum dilution ratio. Each line indicates individual monkeys (C) In another experiment, two groups of monkeys (n=3) were immunized with D35 (4.7 nmol=30 μg) or D35core-dAs40 (4.7 nmol=80 μg) as in (A). 4 weeks after priming, the anti-SV total IgG titer was measured by ELISA. The bars indicate the mean±SEM.
Figure 8:
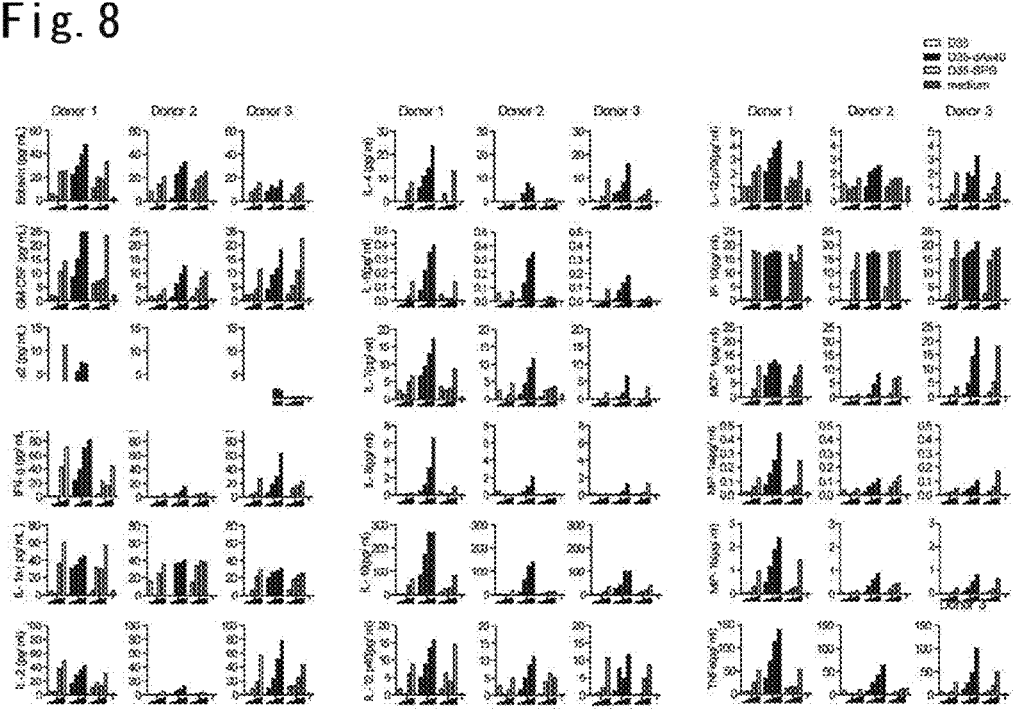
FIG. 8 shows cytokine profiles of D type CpG ODNs in human PBMCs. PBMCs from three Japanese adult volunteers were stimulated with D35, D35-dAs40, D35-SPG, or the medium. Each group in each graph indicates, from the left, D35, D35-dAs40, D35-SPG, and medium. Each ODN was subjected to serial dilution (0.74, 2.2, 6.6, or 20 μg/mL). After 24 hours, the cytokine concentration in the supernatant was measured by a Milliplex cytokine assay kit.

Lastly, the inventors examined the in vivo adjuvant efficacy of D35-dAs40, D35core-dAs40, and D35-SPG in monkey vaccine models and compared the efficacy with that of K3 and the original D35 (FIG. 7). Six groups of monkeys (n=2 or 3) were subcutaneously immunized twice (at a two-week interval) with the shown influenza split vaccine (SV)+adjuvant. 8 weeks from priming, SV specific IgG reactions in the serum were studied by ELISA (FIG. 7A). D35-dAs40 and D35-SPG exhibited better and more consistent adjuvanticity than K3 and the original D35 (FIG. 7B). The inventors also compared the original D35 and D35core-dAs40 by conducting an experiment with another set of monkeys to discover that D35core-dAs40 also exhibits better adjuvanticity than the original D35 (FIG. 7C). These results suggested that D35-dAs40, D35core-dAs40, and D35-SPG function the same as or better than K3 and the original D35 in vivo in monkeys as adjuvants, at least with respect to vaccination of influenza split vaccines. Particularly of note is that in vitro IFN-α and IL-6 profiles were not sufficiently correlated with in vivo adjuvanticity. Thus, the inventors conducted a 26 multiplex cytokine assay using human PBMCs (instead of monkey PBMCs due to the limitation that sufficient amount of monkey PBMCs were unavailable for the assay) that were stimulated with D35, D35-dAs40, or D35-SPG (FIG. 8). Among the 18 types of detected cytokines, correlation was not found between in vitro cytokines and in vivo adjuvanticity (FIG. 8).

(Discussions)

In this Example, the inventors have developed an agent for delivery represented by two types of novel prototypical non-aggregated immunostimulatory A/D type ODNs, D35-dAs40 and D35core-dAs40, for clinical application in humans. These ODNs exhibited a profile of cytokine induction from human PBMCs similar to that of the original D35, which has high IFN-α and low IL-6 induction profile. However, the overall balance between these cytokines slightly shifted toward those of B/K type ODNs (compared to the original D35, IFN-α slightly decreased, and IL-6 increased; FIG. 1). The most important feature of D35-dAs40 and D35core-dAs40 was their excellent solubility in saline. Lyophilized D35-dAs40 and D35core-dAs40 that are stored in a vial can directly dissolved by injection of saline solution (FIG. 5). This is a feature that is required for clinical administration, significantly expanding the application thereof. In addition, D35-dAs40 and D35core-dAs40 both exhibited better adjuvanticity than the original D35 in cynomolgus monkeys when used as an influenza SV adjuvant (FIG. 6). D35-dAs40 and D35core-dAs40 generally exhibited relatively reduced IFN-α and greater IL-6 than the original D35 in vitro (FIG. 4). This result was unexpected. In comparison to K3 that is considered to induce excellent antibody reactions due to direct activation of B cells and potent IL-6 cytokine induction, D35-dAs40 exhibited better and more certain anti-influenza antibody reactions in monkeys (FIG. 7). This suggests that D35-dAs40 and D35core-dAs40 are both excellent vaccine adjuvants in vivo. The inventors also examined D35-SPG consisting of D35-dAs40 and SPG in monkeys. D35-SPG exhibited reduced levels of IFN-α and IL-6 in vitro, but D35-SPG had adjuvanticity that was comparable to D35-dAs40 in vivo (FIG. 7). These data show that the amount and quality of cytokines induced by ODNs in vitro do not correlate with adjuvanticity thereof in vivo. The difference in in vivo distribution may be another important factor that affects the adjuvanticity of modified ODNs. Further investigation on in vivo distribution of ODNs is required.

D35-dAs40 and D35core-dAs40 exhibited IFN-α and IL-6 reactions that were proportional to the dosage similar to the original D35 in dose response analysis (FIG. 4). This is one reason for considering D35-dAs40 and D35core-dAs40 as "D type", not C type or P type CpG ODNs. While C type and P type ODNs also induce IFN-α production, the "ODN dose-cytokine reaction" thereof generally differs from the patterns for D type ODNs. C type and P type ODNs exhibited reduced IFN-α secretion when using a larger amount of ODNs for stimulation. This type of IFN-α reaction was also observed in K3-SPG derived from K3 CpG ODNs, but K3 CpG ODNs are still capable of inducing strong IFN-α production [Kobiyama K et al., (2014) Proceedings of the National Academy of Sciences, vol. 111 no. 83086-3091, doi:10.1073/pnas.1319268111.] The backbones of C, P, and K3-SPG are all phosphorothioate, such that is possible the inverse IFN-α reaction is induced by the phosphorothioate backbone structure; however, the underlying mechanism is currently unknown such that future investigation is needed in the future. In summary, this Example demonstrated that D35-dAs40 and D35core-dAs40 are promising prototypical D type CpG ODNs with high solubility in saline and high adjuvanticity in vivo.

The present invention demonstrated that guanine hexamer sequences and resulting ODN aggregation, which have been considered essential elements up to this point, are not essential for inducing IFN-α production from human PBMCs for A/D type ODNs. Previous studies concluded that aggregation was essential for high IFN-α production by A/D type CpG ODNs [Kerkmann M et al., (2005) J Biol Chem 280: 8086-8093; Wu C C et al., (2004) J Biol Chem 279: 33071-33078; Puig M et al., (2006) Nucleic Acids Res 34: 6488-6495.] However, the data of the inventors demonstrate that aggregation is not an essential requirement for high IFN-α production by A/D type CpG ODNs (FIG. 1), and it is understood that a guanine hexamer sequence in and of itself is not directly involved with TLR9 mediated CpG ODN recognition. The hypothesis that D35 ODNs without a guanine hexamer (e.g., D35A, D35T, D35C) induce potent IFN-α production when DOTAP is added, and the DOTAP complements the aggregation dependent uptake process of D type ODNs, was further supported. In this regard, IFN-α production was completely dependent on the presence of a CpG motif (FIG. 1). These data suggest that the overall immunostimulatory activity of A/D type ODNs can be regulated by two non-overlapping mechanisms: 1) cellular ODN uptake, and 2) CpG motif recognition by TLR9 in endosomes. In summary, the inventors concluded that a palindromic sequence of a 12-mer comprising CpG and a phosphorothioated poly-A tail are the two necessary and sufficient components of the newly developed non-aggregated D type ODNs, D35-dAs40 and D35core-dAs40.

The presence of a guanine hexamer is reportedly a likely contributor to efficient uptake of phosphodiester backboned ODNs by cells via scavenger receptors [Bartz H et al., (2004) Vaccine 23: 148-155; Lee S W et al., (2000) The Journal of Immunology 165: 3631-3639; Jozefowski S et al., (2006) J Leukoc Biol 80: 870-879.] It has been demonstrated that phosphodiester backboned ODNs require an aggregate forming guanine hexamer or a related sequence for cellular ODN uptake and subsequent immunostimulatory function. However, phosphorothioated single stranded CpG ODNs (e.g., B/K type ODNs) have been reported as using DEC-205 for cellular uptake [Lahoud M H et al., (2012) Proceedings of the National Academy of Sciences 109: 16270-16275.] In addition, many molecules such as HMGB1, granulin, and LL37 mediate and enhance ODN or DNA uptake and delivery to TLR9 [Lee C C et al. (2012) Nat Rev Immunol 12: 168-179.] Although not wishing to be bound by any theory, it can be understood that D35-dAs40 and D35core-dAs40 does not form aggregates, but maintain their immunostimulatory activity while depending on the presence of phosphorothioate instead of a phosphodiester poly-A tail, and uptake of D35-dAs40 and D35core-dAs40 is mediated by a phosphorothioate ODN uptake mechanism such as DEC-205 and/or another latent undiscovered accessory molecule.

Guanine hexamer-mediated aggregation or high order structure formation also can affect the localization in cells and promote preferential initial endosome localization of ODNs with a multimer form [Guiducci C et al., (2006) The Journal of Experimental Medicine 203: 1999-2008.] However, the exact regulating mechanism of the preferential early endosome sorting has not been determined. It has been suggested that signaling of IFN-α production starts in CpG/TLR9 interaction that is present in the early endosome [Honda K et al., (2005) Nature 434: 1035-1040; Guiducci C et al., (2006), supra]. It has also been suggested that forced targeting of B/K type ODNs (not a good inducing agent of IFN-α) to early endosome by DOTAP induces IFN-α [Honda K et al., (2005, supra], and the requirements of high order structure and chemical properties of a backbone are not strict when CpG ODNs are targeted to a suitable compartment for IFN-α production. Similarly, a recent report has examined CpG ODNs with two different high order structures bound to a nanoparticle surface to find that multimerized ODNs/nanoparticles induce IFN-α reactions, while monomer ODNs/nanoparticles induce IL-6 reactions [Chinnathambi S et al., (2012) Sci Rep 2: 534.]. These reports suggest that both the ODN structure and targeted cell compartment are important for determining whether the final preferential cytokine reaction is IFN-α or IL-6. Recently reported AP-3 adds another layer to regulation of IFN-α reactions of pDCs [Sasai M et al., (2010) Science 329: 1530-1534.] Localization of TLR9 to lysosome related cell organelle that can be derived from late endosome is reported to be required for IFN-α production from pDCs [Sasai M et al., (2010), supra]. In addition, IFN-α production by TLR9 signaling has been suggested to be regulated by a more complex intracellular sorting mechanism than previously thought [Lee B L, Barton G M (2014) Trends in Cell Biology 24: 360-369.] D35-dAs40 and D35core-dAs40 are comprised of a non-aggregated D type sequence and a phosphorothioate poly-A tail, can induce both IFN-α and IL-6, and can have similar intracellular distribution to C type ODNs, but the dose-reaction thereof exhibited that of D type ODNs. To clarify the exact cell compartment and molecular requirements for inducing IFN-α production by D35-dAs40 and D35core-dAs40, they can be determined by setting additional conditions.

(Difference in Reactions Among Individuals)

Heterogeneity of cytokine reactions for B/K type CpG ODNs in human PBMCs has been reported [Leifer C A et al., (2003) J Immunother 26: 313-319.] Although the overall reaction was largely consistent among various human PBMC samples, the inventors also found variable reactions to A/D type ODN non-aggregated derivatives examined in this Example. Further investigation of the cause of such differences among individuals can be examined for clinical applications of ODNs of this type. In view of the above, non-aggregated form of A/D type ODNs including D35-dAs40 and D35core-dAs40 is recognized as a promising starting material for further development of clinically applicable A/D type ODNs.

Example 2

Confirmation with Other CpG ODNs

This Example confirmed whether a similar effect as D35 is exhibited with other CpG ODNs.

Experiments similar to those conducted for D35 shown in Example 1 were conducted using the following sequences instead of D35 (or D35core) (see above in the specification). The sequence used and their names are shown below (^ indicates a phosphorothioate bond).

```
A2216:
                                        (SEQ ID NO: 55)
g^g^gggacgatcgtc^g^g^g^g^g^g A2216core:
                                        (SEQ ID NO: 56)
gacgatcgtc A2336:
                                        (SEQ ID NO: 57)
g^g^g^gacgacgtcgtg^g^g^g^g^g^g A2336core:
                                        (SEQ ID NO: 58)
acgacgtcgt B2006(PS):
                                        (SEQ ID NO: 59)
t^t^c^g^t^t^t^t^g^t^c^g^t^t^t^t^g^t^c^g^t^t B2006(PO):
                                        (SEQ ID NO: 60)
tcgtcgttttgtcgttttgtcgtt C2395(PS):
                                        (SEQ ID NO: 61)
t^c^g^t^c^g^t^t^t^t^c^g^g^c^g^c^g^c^g^c^c^g C2395(PO):
                                        (SEQ ID NO: 62)
tcgtcgttttcggcgcgcgccg P21889(PS):
                                        (SEQ ID NO: 63)
t^c^g^t^c^g^a^c^g^a^t^c^g^g^c^g^c^g^c^g^
c^c^g P21889(PO):
                                        (SEQ ID NO: 64)
tcgtcgacgatcggcgcgcgccg
```

(Results)

Figure 13:
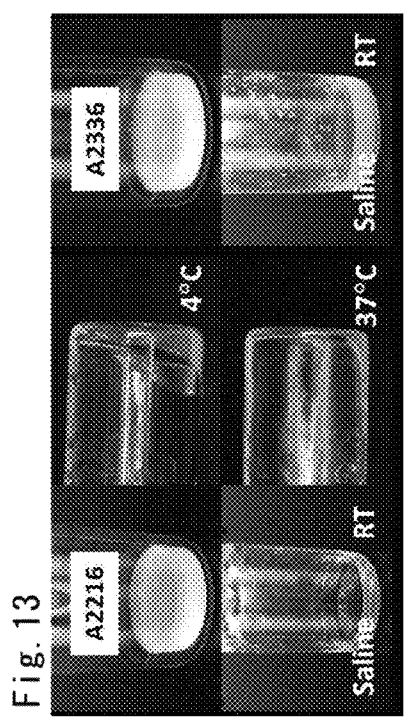
FIG. 13 shows the state of aggregation. The left panel shows A2216, and the right panel shows A2336. The top left picture of the left panel is A2216 itself, and the top right, bottom left, and bottom right pictures show the dissolved state thereof in saline. The top right picture shows the state at 4° C., the bottom left shows the state at room temperature, and the bottom right picture shows the state at 37° C. The right panel shows A2336 on top and that dissolved into saline at room temperature. A2216 can be directly dissolved (10 mg/mL) into saline, but results in a highly viscous solution that is gelated at 4° C. It becomes sol-like at 37° C. (viscosity is high, but fluidity is maintained). It is shown that A2336 cannot be directly dissolved into saline.
Figure 14:
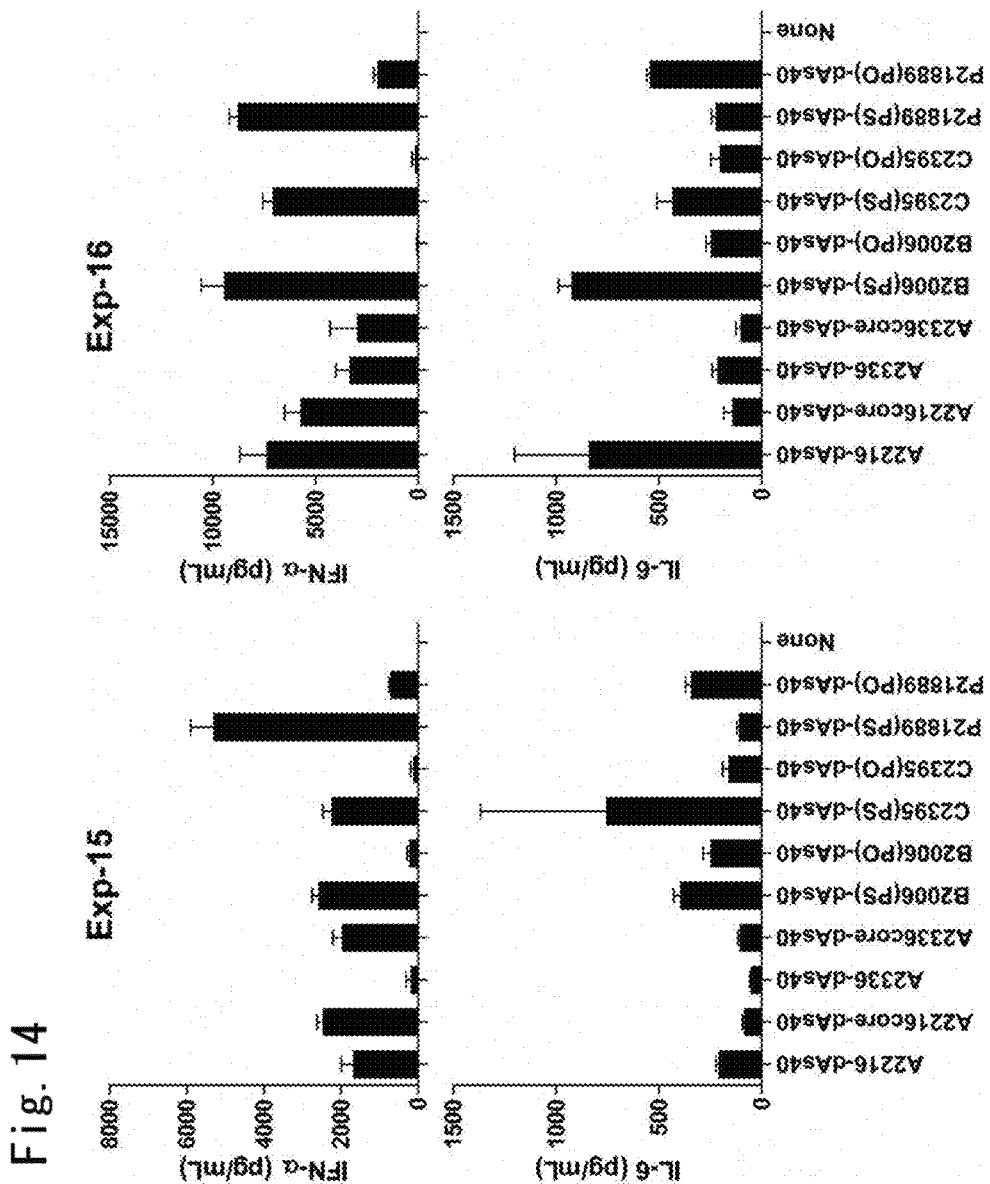
FIG. 14 shows results of studying the effect of other types of CpG ODNs by adding dAs40 on immunostimulatory activity. It can be understood that addition of dAs40 to other types of CpG ODNs (A, B, and P type ODNs) also affect immunostimulatory activity similarly to D35. Each graph in the top row shows results of IFN-α release experiments, and each graph in the bottom row shows an IL-6 release experiment. The left column (Exp-15) and the right column (Exp-16) each show different experiments. Each graph is a result of testing dAs40 bound to, from the left, A2216, A2216core, A2336, A2336core, B2006(PS), B2006(PO), C2395(PS), C2395(PO), P21889(PS), and P21889(PO) (which are SEQ ID NOs: 76-85, respectively). The right end shows an example with nothing placed therein as a control.

Results are shown in FIGS. 13-14. FIG. 13 shows the state of aggregation. A2216 can be directly dissolved (10 mg/mL) into saline, but becomes a highly viscous solution and is gelated at 4° C. At 37° C., the solution becomes sol-like (viscosity is high, but fluidity is maintained). The Figure shows that A2336 cannot be directly dissolved into saline.

FIG. 14 shows results of using A2216, B2006, C2395, and P21889 as other types of CpG ODNs to study the effect of an addition of dAs40 on immunostimulatory activity. It can be understood that addition of dAs40 to other types of CpG ODNs (A, B, and P type ODNs) also affect the immunostimulatory activity similarly to D35.

In view of the above, it is understood that the action of maintaining IFNα induction capability while suppressing endogenous aggregation by adding dAs40 observed for D35 is also effective in other A/D type ODNs (A2216 or A2336), but differences dependent on individual sequence or structure are also observed.

Example 3

Confirmation of Aggregation Suppressing Effect for A/D Type CpG Nucleic Acids Other than D35

Next, this Example tested the aggregation suppressing effect by the addition of dAs40 for A/D type CpG nucleic acids other than D35 by dissolving a lyophilized vial directly into saline, and measured INFα and IL-6 as biological activity on human PBMCs to confirm that the IFNα and IL-6 production was maintained or enhanced as was recognized when dAs40 was added to D35.

(Materials and Methods)

For materials and methods, experiments were conducted according to the same experiment conducted for D35 described in Example 1 (see above) using the following sequences, some of which overlapping with the sequences shown in Examples 1-2.

A2216:
(SEQ ID NO: 55)
g^g^gggacgatcgtc^g^g^g^g^g^g

A2216core:
(SEQ ID NO: 56)
gacgatcgtc

A2216-dAs40:
(SEQ ID NO: 76)

A2336:
(SEQ ID NO: 57)
g^g^g^gacgacgtcgtg^g^g^g^g^g^g

A2336core:
(SEQ ID NO: 58)
acgacgtcgt

A2336-dAs40:
(SEQ ID NO: 78)

D35
(SEQ ID NO: 31)

D35-dAs40:
(SEQ ID NO: 1)

D35core-dAs40:
(SEQ ID NO: 23)

Control (no stimulation)
K3:
(SEQ ID NO: 30)

(Results)

Figure 15:
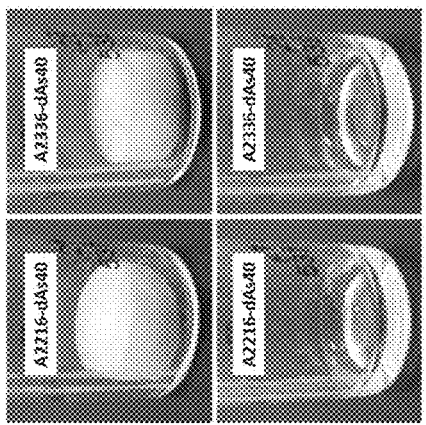
FIG. 15 shows the state of aggregation as in FIG. 13 in the top row. Each picture shows that A2216-dAs40 (left) and A2336-dAs40 (right) (each at 0.5 mg/vial) readily and completely dissolve into 50 µL of saline at room temperature (top row shows results after lyophilization and the next row shows results upon dissolution). The bottom row shows an experiment for studying the effect of each type of CpG ODN by adding dAs40 on immunostimulatory activity (showing results of studying IFN-α and IL-6 production in the supernatant by ELISA with results in stimulating human PBMCs for 24 hours with each oligonucleotide (1 µM)). Comparison of A2216, A2336, D35, dAs40 complexes thereof, K3, and the like is also shown. The bars indicate the mean±SEM. The top row of each column shows results of an IFN-α release experiment, and the bottom row of each column shows results of an IL-6 release experiment. The left column (Exp-15A) and the right column (Exp-16A) each show different experiments. Results are shown for, from the left, A2216, A2216-dAs40, A2216core-dAs40, A2336, A2336-dAs40, A2336core-dAs40, D35, D35-dAs40, and D35core-dAs40. The right end shows results for K3 and the second from the right shows results for the control (no addition).
Figure 15:
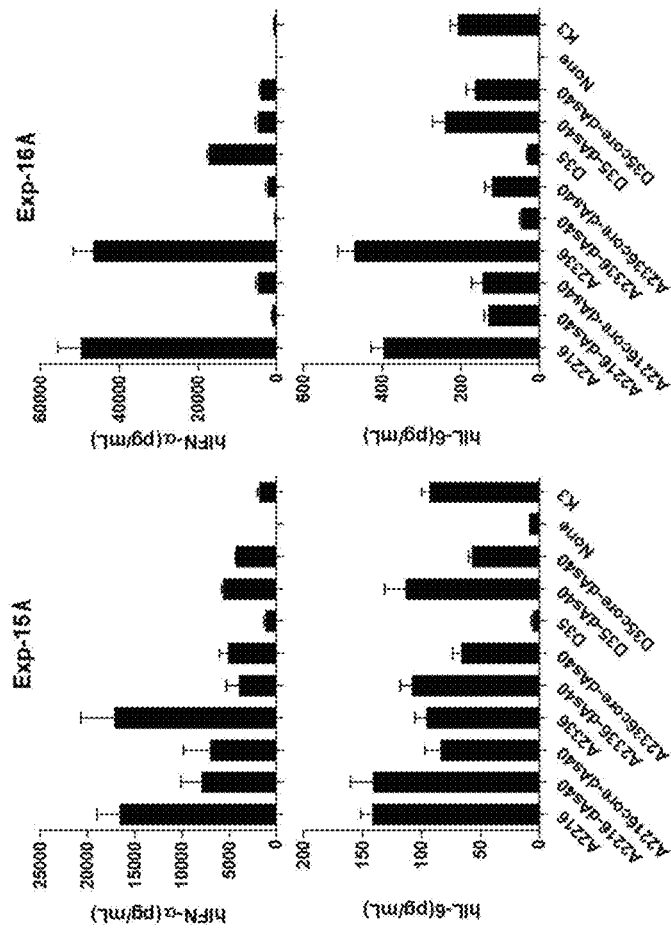

The results are shown in FIG. 15. As shown in FIG. 15, A2216-dAs40 (left) and A2336-dAs40 (right) (both 0.5 mg/vial) were demonstrated to readily and completely dissolve at room temperature into 50 μL of saline. As shown in the bottom row of FIG. 15, investigation of IFN-α and IL-6 production in the supernatant by ELISA from the results of stimulating (1 μM) human PBMCs for 24 hours with each oligonucleotide demonstrates that solubility into saline can be enhanced by adding dAs40 to D type nucleic acids other than D35 (A2216 and A2336) and this has the same effect in the IFN-α and IL-6 production. The results also demonstrate that aggregation suppressing effect due to the addition of dAs40 is observed in not only D35, but also in D type nucleic acids.

In this Example, direct solubility in saline of other A/D type ODNs such as A2216 and A2336 was studied with respect to the presence/absence of an addition of a dAs40 tail. Unexpectedly, A2216 completely dissolved at room temperature into saline, albeit gradually. However, as shown in FIG. 13, the solution changed to a gel at 4° C. The gel liquefied again when the temperature was changed to 37° C. A2336 did not dissolve into saline and formed a gelatinous aggregate. This was the same for D35 (see FIG. 13). When dAs40 was added to A2216 and A2336, the solubility in saline significantly improved. A2216-dAs40 and A2336-dAs40 readily dissolved into saline (FIG. 15). In addition, gelation was not observed at 4° C. A2216-dAs40 and A2336-dAs40 also retained interferon-α inducing capability (FIGS. 14 and 15D). These results demonstrate that an addition of a dAs40 tail is also a useful modification for improving the management of other A/D type ODNs.

Example 4

Effect of the Number of Phosphorothioate Bonds

Next, this Example demonstrated that the property of aggregating when dissolved into saline and INFα and IL-6 production from human PBMCs are almost the same for cases where the number of phosphorothioation(s) at the 5' end is 1 and cases where the number is 2. The details thereof are shown hereinafter.

Specifically, for cases where phosphorothioation (s) at the 5' end is 1 (D35: GsGT . . . (SEQ ID NO: 31) and cases where phosphorothioation (s) at the 5' end is two (D35beta: GsGsT . . . ) (SEQ ID NO: 73), it was confirmed that the property of aggregating when dissolved into saline and IFNα and IL-6 production from human PBMCs are almost the same for D35 and D35beta by the same method described above.

Figure 16:
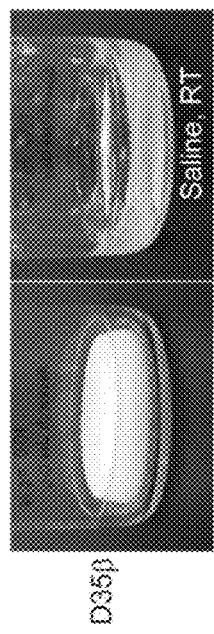
FIG. 16 shows results of an experiment confirming that D35 (one s is bound to the 5' end) and D35β with a similar structure but a different number of s (two s's are bound to the 5' end) exhibit similar behavior in terms of aggregation and IFN-α and IL-6 stimulation. A shows a lyophilized state (left) and a dissolved state, in saline at room temperature, of D35β. B shows results of a stimulation experiment for human IFN-α (top row; pg/mL) and human IL-6 (bottom row; pg/mL) conducted with donor A (left column) and donor B (right column). Each graph shows D35 on the left half (6 cases) and D35β on the right half (6 cases) for each concentration. Results are shown for, from the left, 0 µM, 0.1 µM, 0.3 µM, 1 µM, 3 µM, and 9 µM.
Figure 16:
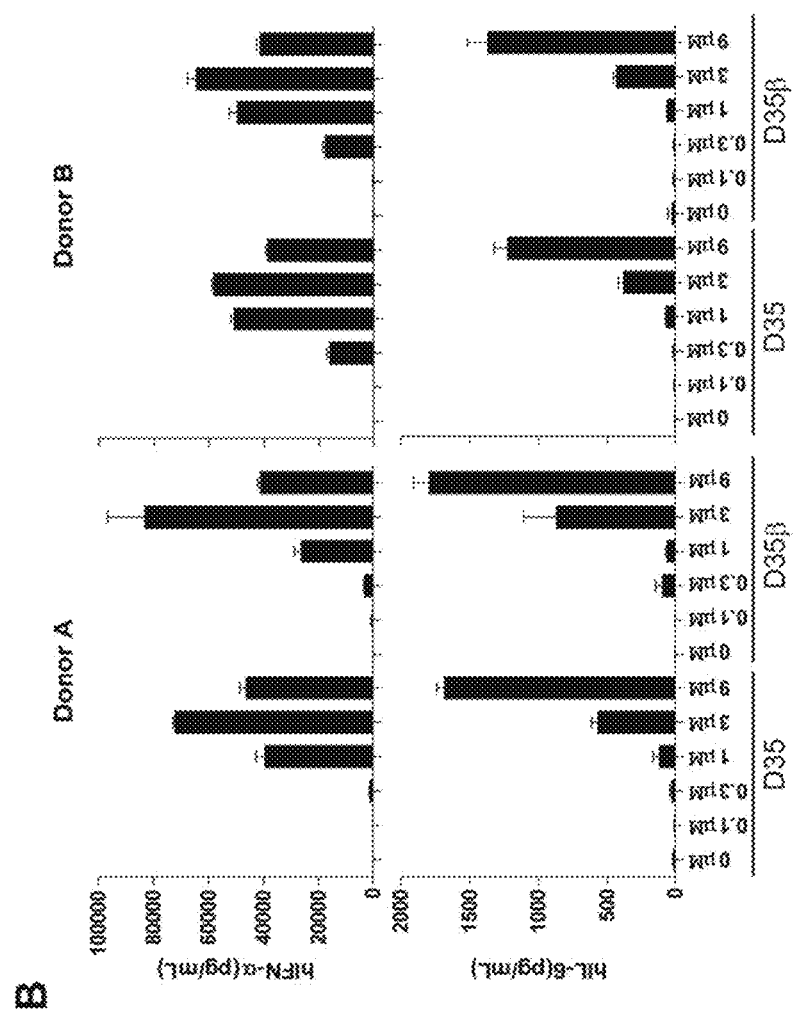

The results are shown in FIG. 16. As shown in FIG. 16, D35 (one s is bound to the 5' end) and D35β (two s are bound to the 5' end) with a similar structure to D35 but different number of s were confirmed to exhibit the same behavior in terms of IFN-α and IL-6 stimulation and aggregation.

Example 5

Formulation Example

Formulations can be manufactured by methods such as those described below.

(Example 1) A suitable volume of saline can be directly added to a suitable amount of lyophilized D35-dAs40 to prepare an injection solution formulation.

(Example 2) A suitable volume of an isotonic solution, 5% glucose solution, can be added to a suitable amount of lyophilized D35-dAs40 to prepare an injection solution formulation.

(Example 3) A suitable volume of electrolyte correction solution, Otsuka sodium chloride injection 10% or the like, can be added to a suitable volume of D35-dAs40 dissolved into water and adjusted to a NaCl concentration of 0.9% to prepare an injection solution formulation.

(Example 4) A suitable amount of D35-dAs40 dissolved into water can be lyophilized to prepare a lyophilized formulation of D35-dAs40 sodium salt.

The agents used in the formulations are available from Otsuka Pharmaceutical Factory (Tokushima, Japan) or GeneDesign, Inc. (Osaka, Japan).

As described above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application No. 2014-263017 filed on Dec. 25, 2014 and Japanese Patent Application No. 2015-118731 filed on Jun. 11, 2015. The entire content of these applications is incorporated herein by reference.

INDUSTRIAL APPLICABILITY

The present invention can be utilized in any industry related to CpG, such as the reagent industry, pharmaceutical industry, or the like.

[Sequence Listing Free Text]

SEQ ID NOs: 1-28 represent the sequences listed in Table 1.
SEQ ID NO: 29: represents a D-poly dAs40 tail.
SEQ ID NO: 30: represents K3 (atcgactctc gagcgttctc).
SEQ ID NO: 31: represents D35.
SEQ ID NO: 32: represents D35A.
SEQ ID NO: 33: represents D35T.
SEQ ID NO: 34: represents D35C.
SEQ ID NOs: 35-48: represent the sequences in FIG. 9.
SEQ ID NOs: 49-54: represent the sequences in FIG. 10.
SEQ ID NO: 55: represents the phosphorothioated sequence of A2216.
SEQ ID NO: 56: represents the core moiety of A2216.
SEQ ID NO: 57: represents the phosphorothioated sequence of A2336.
SEQ ID NO: 58: represents the core moiety of A2336.
SEQ ID NO: 59: represents the phosphorothioated sequence of B2006.
SEQ ID NO: 60: represents the full length of B2006.
SEQ ID NO: 61: represents the phosphorothioated sequence of C2395.
SEQ ID NO: 62: represents full length of C2395.
SEQ ID NO: 63: represents the phosphorothioated sequence of P21889.
SEQ ID NO: 64: represents full length of P21889.
SEQ ID NO: 65: represents full length of A2216.
SEQ ID NO: 66: represents full length of A2336.
SEQ ID NO: 67: represents CPG 7909.
SEQ ID NO: 68: represents PF-3512676.
SEQ ID NO: 69: represents CYT003-QBG10.
SEQ ID NO: 70: represents 1018 ISS.
SEQ ID NO: 71: represents Kappaproct (DIMS 0150).
SEQ ID NO: 72: represents D35-dNs40. (GsGsTGCATC-GATGCAGGGGsGsGs-Ns40).
SEQ ID NO: 73: represents the sequence of D35β (starts with GsGs).
SEQ ID NO: 74: represents the sequence of dAs40-D35.
SEQ ID NO: 75: represents the sequence of D35-dAs40-D35.
SEQ ID NO: 76: represents A2216+dAs40.
SEQ ID NO: 77: represents A2216core+dAs40.
SEQ ID NO: 78: represents A2336+dAs40.
SEQ ID NO: 79: represents A2336core+dAs40.
SEQ ID NO: 80: represents B2006(PS)+dAs40.
SEQ ID NO: 81: represents B2006(PO)+dAs40.
SEQ ID NO: 82: represents C2395(PS)+dAs40.
SEQ ID NO: 83: represents C2395(PO)+dAs40.
SEQ ID NO: 84: represents P21889(PS)+dAs40.
SEQ ID NO: 85: represents P21889(PO)+dAs40.

The invention claimed is:

1. An agent for delivery of an immunostimulatory oligonucleotide nucleic acid medicament, wherein the agent comprises a nucleic acid which comprises one or more phosphorothioated nucleotide, wherein the nucleic acid which comprises one or more phosphorothioated nucleotide has a length of 10 bases to 100 bases, wherein the nucleic acid consists of adenines or cytosines, wherein the agent does not comprise schizophyllan (SPG) and is bound to a moiety having biological activity of an immunostimulatory oligonucleotide, wherein the moiety having biological activity of said immunostimulatory oligonucleotide does not comprise schizophyllan (SPG) and comprises a core moiety with biological activity of an A/D type immunostimulatory oligonucleotide or a full length A/D type immunostimulatory oligonucleotide, wherein the moiety having biological activity of said immunostimulatory oligonucleotide consists of a core moiety selected from the group consisting of a core moiety TGCATCGATGCA (SEQ ID NO: 22) of a D35 oligonucleotide, a core moiety GACGATCGTC (SEQ ID NO: 56) of A2216 oligonucleotide, a core moiety ACGACGTCGT (SEQ ID NO: 58) of A2336 oligonucleotide, and SEQ ID NOs: 5-21, and wherein the biological activity of said immunostimulatory oligonucleotide is one or both of interferon-alpha (IFNα) production inducing activity and interleukin-6 (IL6) production inducing activity.

2. The agent for delivery of claim 1, wherein the nucleic acid which comprises one or more phosphorothioated nucleotide is bound to a 3' end of the immunostimulatory oligonucleotide to prevent formation of a high order aggregate in saline due to consecutive guanines in the immunostimulatory oligonucleotide.

3. The agent for delivery of claim 1, wherein the phosphorothioated nucleotide content in the nucleic acid is 25% or greater.

4. The agent for delivery of claim 1, wherein the phosphorothioated nucleotide content in the nucleic acid is 33% or greater.

5. The agent for delivery of claim 1, wherein the phosphorothioated nucleotide content in the nucleic acid is 50% or greater.

6. A composition comprising an oligonucleotide, comprising (a) (i) a full length oligonucleotide having biological activity of an immunostimulatory oligonucleotide, or (ii) a core moiety of an oligonucleotide having biological activity of an immunostimulatory oligonucleotide, wherein the biological activity of said immunostimulatory oligonucleotide is one or both of interferon-alpha (IFNα) production inducing activity and interleukin-6 (IL6) production inducing activity; wherein the full length oligonucleotide having biological activity of an immunostimulatory oligonucleotide comprises a full length A/D type immunostimulatory oligonucleotide or wherein the core moiety of the oligonucleotide having biological activity of said immunostimulatory oligonucleotide comprises an A/D type immunostimulatory oligonucleotide core moiety, wherein the full length oligonucleotide having biological activity of an immunostimulatory oligonucleotide or the core moiety of the oligonucleotide having biological activity of said immunostimulatory oligonucleotide consists of a core moiety selected from the group consisting of a core moiety TGCATCGATGCA (SEQ ID NO: 22) of a D35 oligonucleotide, a core moiety GACGATCGTC (SEQ ID NO: 56) of A2216 oligonucleotide, and a core moiety ACGACGTCGT (SEQ ID NO: 58) of A2336 oligonucleotide, and SEQ ID NOs: 5-21; and (b) a nucleic acid which comprises one or more phosphorothioated nucleotide, wherein the nucleic acid which comprises one or more phosphorothioated nucleotide has a length of 10 bases to 100 bases, wherein the nucleic acid consists of adenines or cytosines, wherein the composition does not comprise schizophyllan (SPG).

7. The composition of claim 6, wherein the nucleic acid which comprises one or more phosphorothioated nucleotide is bound to a 3' end of the full length oligonucleotide or to a 3' end of the core moiety of the oligonucleotide having immunostimulatory, to prevent formation of a multimeric immunostimulatory oligonucleotide in saline due to consecutive guanines in the immunostimulatory oligonucleotide.

8. The oligonucleotide of claim 6, wherein the phosphorothioated nucleotide content in the nucleic acid is 25% or greater.

9. The oligonucleotide of claim 6, wherein the phosphorothioated nucleotide content in the nucleic acid is 33% or greater.

10. The composition of claim 6, wherein the phosphorothioated nucleotide content in the nucleic acid is 50% or greater.

11. The composition of claim 6, wherein the phosphorothioated nucleotide content in the nucleic acid is greater than 50%.

12. The agent for delivery of claim 1, wherein the nucleic acid which comprises one or more phosphorothioated nucleotide is bound to a 5' end of the immunostimulatory oligonucleotide, to prevent formation of a high order aggregate in saline due to consecutive guanines in the immunostimulatory oligonucleotide.

13. The composition of claim 6, wherein the nucleic acid which comprises one or more phosphorothioated nucleotide is bound to a 5' end of the full length oligonucleotide or to a 5' end of the core moiety of the oligonucleotide having biological activity of the immunostimulatory oligonucleotide, to prevent formation of a multimeric immunostimulatory oligonucleotide in saline due to consecutive guanines in the immunostimulatory oligonucleotide.

* * * * *